United States Patent
Wu et al.

(10) Patent No.: US 8,207,390 B2
(45) Date of Patent: Jun. 26, 2012

(54) PROCESS TO PRODUCE LOW VISCOSITY POLY-ALPHA-OLEFINS

(75) Inventors: Margaret May-Som Wu, Skillman, NJ (US); Catalina L. Coker, Baytown, TX (US); John F. Walzer, Jr., Seabrook, TX (US); Peijun Jiang, League City, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 1342 days.

(21) Appl. No.: 11/489,313

(22) Filed: Jul. 19, 2006

(65) Prior Publication Data

US 2007/0043248 A1 Feb. 22, 2007

Related U.S. Application Data

(60) Provisional application No. 60/700,600, filed on Jul. 19, 2005.

(51) Int. Cl.
C07C 2/22 (2006.01)

(52) U.S. Cl. ........ 585/523; 585/502; 585/520; 585/521; 585/522; 585/525

(58) Field of Classification Search .................. 585/523, 585/502, 520, 521, 522, 525
See application file for complete search history.

(56) References Cited

U.S. PATENT DOCUMENTS

| | | |
|---|---|---|
| 2,978,442 A | 4/1961 | Brightbill et al. |
| 3,149,178 A | 9/1964 | Hamilton et al. |
| 3,164,578 A | 1/1965 | Baker et al. |
| 3,382,291 A | 5/1968 | Brennan |
| 3,742,082 A | 6/1973 | Brennan |
| 3,769,363 A | 10/1973 | Brennan |
| 3,780,128 A | 12/1973 | Shubkin |
| 3,876,720 A | 4/1975 | Heilman et al. |
| 3,883,417 A | 5/1975 | Woo et al. |
| 4,016,349 A | 4/1977 | McKenna |
| 4,132,663 A | 1/1979 | Heilman et al. |
| 4,149,178 A | 4/1979 | Estes |
| 4,172,855 A | 10/1979 | Shubkin et al. |
| 4,180,575 A | 12/1979 | Rochling et al. |
| 4,239,930 A | 12/1980 | Allphin et al. |
| 4,263,465 A | 4/1981 | Sheng et al. |
| 4,263,712 A | 4/1981 | Schroder |
| 4,367,352 A | 1/1983 | Watts, Jr. et al. |
| 4,413,156 A | 11/1983 | Watts, Jr. et al. |
| 4,434,408 A | 2/1984 | Baba et al. |
| 4,451,684 A | 5/1984 | Pasky |
| 4,469,912 A | 9/1984 | Blewett et al. |
| 4,587,368 A | 5/1986 | Pratt |
| 4,701,489 A | 10/1987 | Hughes et al. |
| 4,704,491 A | 11/1987 | Tsutsui et al. |
| 4,827,064 A | 5/1989 | Wu |
| 4,827,073 A | 5/1989 | Wu |
| 4,892,851 A | 1/1990 | Ewen et al. |
| 4,910,355 A | 3/1990 | Shubkin et al. |
| 4,912,272 A | 3/1990 | Wu |
| 4,914,254 A | 4/1990 | Pelrine |
| 4,926,004 A | 5/1990 | Pelrine et al. |
| 4,950,822 A | 8/1990 | Dileo et al. |
| 4,956,122 A | 9/1990 | Watts et al. |
| 4,962,262 A | 10/1990 | Winter et al. |
| 4,967,032 A | 10/1990 | Ho et al. |
| 4,990,709 A | 2/1991 | Wu |
| 4,990,771 A | 2/1991 | Minoura et al. |
| 5,012,020 A | 4/1991 | Jackson et al. |
| 5,017,299 A | 5/1991 | Gutierrez et al. |
| 5,017,714 A | 5/1991 | Welborn, Jr. |
| 5,068,487 A | 11/1991 | Theriot |
| 5,087,788 A | 2/1992 | Wu |
| 5,177,276 A | 1/1993 | Beach et al. |
| 5,186,851 A | 2/1993 | Gutierrez et al. |
| 5,188,724 A | 2/1993 | Heilman et al. |
| 5,220,100 A | 6/1993 | Massie et al. |
| 5,264,642 A | 11/1993 | Wu |
| 5,369,196 A | 11/1994 | Matsumoto et al. |

(Continued)

FOREIGN PATENT DOCUMENTS

EP 0 277 004 8/1988

(Continued)

OTHER PUBLICATIONS

Wills, J. G., "Synthetic Lubricants," Lubrication Fundamentals, Marcel Dekker, Inc., New York, 1980, pp. 75-80. J. Brennan, "Wide-Temperature Range Synthetic Hydrocarbon Fluids", Ind. Eng. Chem. Prod. Res. Dev., 1980, vol. 19, pp. 2-6.
K. Denbigh, "The Kinetics of Continuous Reaction Processes: Application to Polymerization", J. Applied Chem, 1951, vol. 1, pp. 227-236.
K. Denbigh, "Continuous Reactions: Part II. The Kinetics of Steady State Polymerisation", Trans Faraday Soc., 1947, vol. 43, pp. 648-660.
A. Munoz-Escalona et al., "Single-Site Supported Catalysts for Ethylene Polymerization", Metallocene Tech., 1999, pp. 2242-2246.
Z. Fan et al., "Effect of Ethoxy- and Methoxysilane Donors in Propene/1-Hexene Copolymerization With High-Yield Supported Ziegler-Natta Catalysts", Macromolecular Chemistry and Physics, 1994, vol. 195, pp. 3889-3899.
G. Gokel ed, Dean's Handbook of Organic Chemistry, 2nd Edition, McGraw-Hill, 2004, available online at hhtp://knovel.com.
M. LeVan et al. "Adsorption and Ion Exchange" Perry's Chemical Engineer's Handbook, 7th ed. 1997 pp. 16-1-16-66.
O. Levenspiel, "Ch. 7 Design for Multiple Reactions", Chemical Reaction Engineering, 2nd ed., 1972, pp. 196-209.

(Continued)

Primary Examiner — In Suk Bullock
Assistant Examiner — Bradley Etherton
(74) Attorney, Agent, or Firm — Kristina M. Leavitt; Nancy T. Krawczyk; Catherine L. Bell

(57) ABSTRACT

A low viscosity poly(alpha-olefin) (PAO) is produced by contacting one or more C3 to C24 alpha-olefins with an unbridged, substituted bis-cyclopentadienyl transition metal compound, a non-coordinating anion activator, and an alkyl-aluminum compound. The molar ratio of transition metal compound to activator is 10:1 to 0.1:1 and the molar ratio of alkyl aluminum compound to transition metal compound is 1:4 to 4000:1. The transition metal compound has either (a) at least one non-isoolefin substitution on both cyclopentadienyl rings, or (b) at least two substitutions on at least one cyclopentadienyl ring. The PAO is comprised of at least 50 mole % of C3 to C24 alpha-olefins, has a Mw/Mn between 1 and 1.4, and a kinematic viscosity at 100° C. of 20 cSt or less.

67 Claims, No Drawings

U.S. PATENT DOCUMENTS

| | | | |
|---|---|---|---|
| 5,382,739 A | 1/1995 | Atkins et al. | |
| 5,462,995 A | 10/1995 | Hosaka et al. | |
| 5,498,815 A | 3/1996 | Schaerfl, Jr. et al. | |
| 5,552,504 A | 9/1996 | Bennett et al. | |
| 5,637,400 A | 6/1997 | Brekner et al. | |
| 5,679,812 A | 10/1997 | Winter et al. | |
| 5,688,887 A | 11/1997 | Bagheri et al. | |
| 5,690,832 A | 11/1997 | Tavlarides et al. | |
| 5,731,254 A | 3/1998 | Winter et al. | |
| 5,811,379 A | 9/1998 | Rossi et al. | |
| 5,846,896 A | 12/1998 | Ewen | |
| 5,852,143 A | 12/1998 | Sishta et al. | |
| 5,859,159 A * | 1/1999 | Rossi et al. | 526/170 |
| 6,043,401 A | 3/2000 | Bagheri et al. | |
| 6,087,307 A | 7/2000 | Kaminski et al. | |
| 6,133,209 A | 10/2000 | Rath et al. | |
| 6,147,271 A | 11/2000 | Strebel et al. | |
| 6,180,575 B1 | 1/2001 | Nipe | |
| 6,388,032 B1 | 5/2002 | Yamaura et al. | |
| 6,414,090 B2 | 7/2002 | Minami et al. | |
| 6,414,091 B2 | 7/2002 | Moritomi et al. | |
| 6,479,722 B1 | 11/2002 | De Wet et al. | |
| 6,548,723 B2 * | 4/2003 | Bagheri et al. | 585/517 |
| 6,548,724 B2 | 4/2003 | Bagheri et al. | |
| 6,642,169 B2 * | 11/2003 | Weatherhead | 502/118 |
| 6,646,174 B2 | 11/2003 | Clarembeau | |
| 6,706,828 B2 * | 3/2004 | DiMaio | 526/160 |
| 6,713,438 B1 | 3/2004 | Baillargeon et al. | |
| 6,824,671 B2 | 11/2004 | Goze et al. | |
| 6,858,767 B1 | 2/2005 | DiMaio et al. | |
| 6,960,700 B1 | 11/2005 | Sethna et al. | |
| 7,060,768 B2 | 6/2006 | Brookhart et al. | |
| 7,129,197 B2 | 10/2006 | Song et al. | |
| 7,473,815 B2 | 1/2009 | Lambert et al. | |
| 7,544,850 B2 | 6/2009 | Goze et al. | |
| 7,547,811 B2 | 6/2009 | Kramer et al. | |
| 7,592,497 B2 | 9/2009 | Yang et al. | |
| 7,601,256 B2 | 10/2009 | Beall | |
| 2001/0041817 A1* | 11/2001 | Bagheri et al. | 585/517 |
| 2001/0041818 A1 | 11/2001 | Bagheri et al. | |
| 2003/0055184 A1 | 3/2003 | Song et al. | |
| 2004/0022508 A1 | 2/2004 | Belardi et al. | |
| 2004/0033908 A1 | 2/2004 | Deckman et al. | |
| 2004/0087746 A1 | 5/2004 | Razavi | |
| 2004/0097772 A1 | 5/2004 | Deckers et al. | |
| 2004/0147693 A1 | 7/2004 | DiMaio | |
| 2004/0220359 A1 | 11/2004 | Abhari et al. | |
| 2004/0230016 A1 | 11/2004 | Blackborow et al. | |
| 2005/0059563 A1 | 3/2005 | Sullivan et al. | |
| 2005/0101761 A1 | 5/2005 | Lambert et al. | |
| 2005/0183988 A1 | 8/2005 | Freerks et al. | |
| 2007/0000807 A1 | 1/2007 | Wu et al. | |
| 2007/0011832 A1 | 1/2007 | Keidel et al. | |
| 2007/0043248 A1 | 2/2007 | Wu et al. | |
| 2007/0208151 A1 | 9/2007 | Okada et al. | |
| 2009/0005279 A1 | 1/2009 | Wu et al. | |
| 2009/0156874 A1 | 6/2009 | Patil et al. | |
| 2009/0281360 A1 | 11/2009 | Knowles et al. | |
| 2010/0069687 A1 | 3/2010 | Kosover et al. | |

FOREIGN PATENT DOCUMENTS

| | | |
|---|---|---|
| EP | 0 277 007 | 8/1988 |
| EP | 0 284 708 | 10/1988 |
| EP | 0 321 852 | 6/1989 |
| EP | 0 349 276 | 1/1990 |
| EP | 0 377 306 | 7/1990 |
| EP | 0 403 866 | 12/1990 |
| EP | 0 513 380 | 11/1992 |
| EP | 0 613 873 | 9/1994 |
| EP | 0 680 942 | 11/1995 |
| EP | 0 930 320 | 7/1999 |
| EP | 0 992 517 | 4/2000 |
| EP | 1 028 128 | 8/2000 |
| EP | 1 309 633 | 5/2003 |
| EP | 1 342 707 | 9/2003 |
| EP | 1 607 415 | 12/2005 |
| EP | 1607415 A1 * | 12/2005 |
| GB | 938069 | 9/1963 |
| IN | 191553 | 12/2003 |
| JP | 6336590 | 12/1994 |
| JP | 2005-200446 | 7/2005 |
| WO | WO 96/23751 | 8/1996 |
| WO | WO 99/67347 | 12/1999 |
| WO | 00/58423 | 10/2000 |
| WO | WO 02/14384 | 2/2002 |
| WO | 03/009136 | 1/2003 |
| WO | WO 03/020856 | 3/2003 |
| WO | 03/051943 | 6/2003 |
| WO | 03/071369 | 8/2003 |
| WO | 03/104292 | 12/2003 |
| WO | 2004/046214 | 6/2004 |
| WO | 2007/011459 | 1/2007 |
| WO | 2007/011462 | 1/2007 |
| WO | 2007/011832 | 1/2007 |
| WO | 2007/011973 | 1/2007 |
| WO | 2007/145924 | 12/2007 |
| WO | 2007/146081 | 12/2007 |
| WO | 2008/010862 | 1/2008 |
| WO | 2008/010865 | 1/2008 |
| WO | 2009/017953 | 2/2009 |
| WO | 2009/137264 | 11/2009 |

OTHER PUBLICATIONS

N. Naga et al., "Effect of Co-Catalyst System On a-Olefin Polymerization With Rac- and Meso- [Dimethylsilylenebis(2,3,5-Trimethyl-Cyclopentadienyl]Zirconium Dichloride", Macromol. Rapid Commun., 1997, vol. 18, pp. 581-589.

N. Naga et al, "*Polymerization Behavior of a-Olefins With Rac- And Meso-Type Ansa-Metallocene Catalysts: Effects of Cocatalyst and Metallocene Ligand*", Macromolecular Chemistry Physics, 1999, vol. 200, pp. 1587-1594.

F. Rodriguez, "*The Molecular Weight of Polymers*", Principles of Polymer Systems, 1970, Chapter 6, pp. 115-144.

M. Sacchi et al., "*Use of Different Alkoxysilanes As External Donors in MgCl$_2$-Supported Ziegler-Natta Catalysts to Obtain Propene/1-Butene Copolymers With Different Microstructure*", Macromolecular Chemistry and Physics, 1994, vol. 195, pp. 2805-2816.

T. Seraidaris et al., "*High-Molar-Mass Polypropene with Tunable Elastic Properties by Hafnocene/Borate Catalysts*", Journal of Polymer Science: Part A: Polymer Chemistry, 2006, vol. 44, pp. 4743-4751.

"*Mobil Releases SuperSyn PAOs*", Lubrication Engineers, 1999, vol. 55, Part 8, pp. 45.

Tiba data, "*TIBA datasheet*" available on-line at www.albermarle.com on Aug. 26, 2010.

* cited by examiner

PROCESS TO PRODUCE LOW VISCOSITY POLY-ALPHA-OLEFINS

PRIORITY CLAIM

This invention claims the benefit of U.S. Ser. No. 60/700,600, filed Jul. 19, 2005.

FIELD OF THE INVENTION

This invention relates to a process to produce poly-alpha-olefins (PAOs) in the presence of a metallocene catalyst with a non-coordinating anion activator and hydrogen.

DESCRIPTION OF RELATED ART

Efforts to improve upon the performance of natural mineral oil-based lubricants by the synthesis of oligomeric hydrocarbon fluids have been the subject of important research and development in the petroleum industry for at least fifty years. These efforts have led to the relatively recent market introduction of a number of synthetic lubricants. In terms of lubricant property improvement, the thrust of the industrial research efforts involving synthetic lubricants have been towards fluids exhibiting useful viscosities over a wide temperature range, i.e., improved viscosity index (VI), while also showing lubricities, thermal and oxidative stabilities and pour points equal to or better than those for mineral oil.

The viscosity-temperature relationship of a lubricating oil is one of the critical criteria which must be considered when selecting a lubricant for a particular application. The mineral oils commonly used as a base for single and multigrade lubricants exhibit a relatively large change in viscosity with a change in temperature. Fluids exhibiting such a relatively large change in viscosity with temperature are said to have a low viscosity index. Viscosity index is an empirical number which indicates the rate of change in the viscosity of an oil within a given temperature range. A high VI oil, for example, will thin out at elevated temperatures more slowly than a low VI oil. Usually, a high VI oil is more desirable because it has higher viscosity at higher temperature, which translates into better lubrication and better protection of the contacting machine elements, preferably at high temperatures and or at temperatures over a wide range. VI is calculated according to ASTM method D 2270.

PAOs comprise a class of hydrocarbons manufactured by the catalytic oligomerization (polymerization to low-molecular-weight products) of linear α-olefin (LAO) monomers. These typically range from 1-octene to 1-dodecene, with 1-decene being a preferred material, although oligomeric copolymers of lower olefins such as ethylene and propylene may also be used, including copolymers of ethylene with higher olefins as described in U.S. Pat. No. 4,956,122 and the patents referred to therein. PAO products have achieved importance in the lubricating oil market. Typically there are two classes of synthetic hydrocarbon fluids (SHF) produced from linear alpha-olefins, the two classes of SHF being denoted as PAO and HVI-PAO (high viscosity index PAO's). PAO's and HVI-PAO's of different viscosity grades are typically produced using promoted $BF_3$ or $AlCl_3$ catalysts.

Specifically, PAOs may be produced by the polymerization of olefin feed in the presence of a catalyst such as $AlCl_3$, $BF_3$, or $BF_3$ complexes. Processes for the production of PAOs are disclosed, for example, in the following U.S. Pat. Nos. 3,149,178; 3,382,291; 3,742,082; 3,769,363; 3,780,128; 4,172,855 and 4,956,122, which are fully incorporated by reference. PAOs are also discussed in: Will, J. G. *Lubrication Fundamentals*, Marcel Dekker: New York, 1980. Subsequent to polymerization, the PAO lubricant range products are typically hydrogenated in order to reduce the residual unsaturation, generally to a level of greater than 90%. HVI-PAO's may also be conveniently made by the polymerization of an alpha-olefin in the presence of a polymerization catalyst such as Friedel-Crafts catalysts. These include, for example, aluminum trichloride, boron trifluoride, aluminum trichloride or boron trifluoride promoted with water, with alcohols such as ethanol, propanol, or butanol, with carboxylic acids, or with esters such as ethyl acetate or ethyl propionate or ether such as diethyl ether, diisopropyl ether, etc. (See for example, the methods disclosed by U.S. Pat. No. 4,149,178 or 3,382,291.) Other descriptions of PAO synthesis are found in the following U.S. Pat. Nos. 3,742,082 (Brennan); 3,769,363 (Brennan); 3,876,720 (Heilman); 4,239,930 (Allphin); 4,367,352 (Watts); 4,413,156 (Watts); 4,434,408 (Larkin); 4,910,355 (Shubkin); 4,956,122 (Watts); and 5,068,487 (Theriot).

Another class of HVI-PAOs may be prepared by the action of a supported, reduced chromium catalyst with an alpha-olefin monomer. Such PAOs are described in U.S. Pat. No. 4,827,073 (Wu); U.S. Pat. No. 4,827,064 (Wu); U.S. Pat. No. 4,967,032 (Ho et al.); U.S. Pat. No. 4,926,004 (Pelrine et al.); and U.S. Pat. No. 4,914,254 (Pelrine). Commercially available PAOs include SpectraSyn™ 2, 4, 5, 6, 8, 10, 40, 100 and SpectraSyn Ultra™ 150, SpectraSyn Ultra™ 300, SpectraSyn Ultra™ 1000, etc. (ExxonMobil Chemical Company, Houston Tex.).

Synthetic PAOs have found wide acceptability and commercial success in the lubricant field for their superiority to mineral based lubricants. In terms of lubricant property improvement, industrial research efforts on synthetic lubricants have led to PAO fluids exhibiting useful viscosities over a wide range of temperature, i.e., improved viscosity index, while also showing lubricity, thermal and oxidative stability and pour point equal to or better than mineral oil. These relatively new synthetic lubricants lower mechanical friction, enhancing mechanical efficiency over the full spectrum of mechanical loads and do so over a wider range of operating conditions than mineral oil lubricants.

Performance requirements of lubricants are becoming increasingly stringent. New PAOs with improved properties, such as high viscosity index (VI), low pour point, reduced volatility, high shear stability, improved wear performance, increased thermal and oxidative stability, and or wider viscosity range, are needed to meet new performance requirements for lubricants. New methods to provide such new PAOs with improved properties are also needed.

Efforts have been made to prepare various PAOs using metallocene catalyst systems. Examples include U.S. Pat. No. 6,706,828 (equivalent to US 2004/0147693), where PAOs are produced from meso-forms of certain metallocene catalysts under high hydrogen pressure with methyl alumoxane as a activator. Comparative example D of U.S. Pat. No. 6,706,828, however, uses rac-dimethylsilylbis(2-methyl-indenyl)zirconium dichloride in combination with methylalumoxane (MAO) at 100° C. in the presence of hydrogen to produce polydecene. Likewise, WO 02/14384 discloses, among other things, in examples J and K the use of rac-ethyl-bis(indenyl) zirconium dichloride or rac-dimethylsilyl-bis(2-methyl-indenyl) zirconium dichloride in combination with MAO at 40° C. (at 200 psi hydrogen or 1 mole of hydrogen) to produce isotactic polydecene reportedly having a Tg of −73.8° C., a $KV_{100}$ of 702 cSt, and a VI of 296; or to produce polydecene reportedly having a Tg of −66° C., a $KV_{100}$ of 1624, and a VI of 341, respectively. Further WO 99/67347 discloses in example 1 the use of ethylidene bis(tetrahydroindenyl)zirconium dichloride in combination with MAO at 50° C. to produce a polydecene having an Mn of 11,400 and 94% vinylidene double bond content.

Others have made various PAOs, such as polydecene, using various metallocene catalysts not typically known to produce polymers or oligomers with any specific tacticity. Examples include WO 96/23751, EP 0 613 873, U.S. Pat. No. 5,688,887, U.S. Pat. No. 6,043,401, WO 03/020856 (equivalent to US 2003/0055184), U.S. Pat. No. 5,087,788, U.S. Pat. No. 6,414,090, U.S. Pat. No. 6,414,091, U.S. Pat. No. 4,704,491, U.S. Pat. No. 6,133,209, and U.S. Pat. No. 6,713,438.

To date however, PAO's made with metallocenes have not found wide applicability in the marketplace, particularly the lubricant marketplace, due to inefficient process, cost and property deficits. The instant invention address such and other needs by providing new PAO's having excellent property combinations and an improved process to produce them.

U.S. Pat. No. 6,548,724 (equivalent to US 2001/0041817 and U.S. Pat. No. 6,548,723) disclose production of oligomer oils using certain metallocene catalysts, typically in combination with methyl alumoxane. Column, 20, line 40 to 44 of U.S. Pat. No. 6,548,724 indicates that Examples, 10-11 indicate that di, tri or tetra substitutions on the cyclopentadienyl rings of the metallocenes are useful for production of high viscosity polyalphaolefins, (viscosities it he range of 20 to 5000 cSt at 100° C.) with improved yields whereas penta alkyl substituted cyclopentadienyl rings are poor."

PCT/US06/21231 filed Jun. 2, 2006 claiming the benefit of U.S. Ser. No. 60/700,600, filed Jul. 19, 2005 describes the production of liquids from monomers having 5 to 24 carbon atoms using racemic metallocenes and non-coordinating anion activators.

Other references of interest include: EP0284708, U.S. Pat. No. 5,846,896, U.S. Pat. No. 5,679,812, EP0321852, U.S. Pat. No. 4,962,262 EP0513380, US2004/0230016, and U.S. Pat. No. 6,642,169.

SUMMARY OF INVENTION

This invention relates to a process to produce a polyalpha-olefin comprising:

1) contacting one or more alpha-olefin monomers having 3 to 24 carbon atoms with an unbridged substituted bis cyclopentadienyl transition metal compound having: 1) at least one non-isoolefin substitution on each cyclopentadienyl ring, or 2) at least two substitutions on at least one cyclopentadienyl ring, preferably having at least two substitutions on each cyclopentadienyl ring, a non-coordinating anion activator, and optionally an alkyl-aluminum compound, where the molar ratio of transition metal compound to activator is 10:1 to 0.1:1, and if the alkyl aluminum compound is present then the molar ratio of alkyl aluminum compound to transition metal compound is 1:4 to 4000:1, under polymerization conditions wherein:

i) hydrogen is present at a partial pressure of 1 to 50 psi or a hydrogen concentration of 10 to 10,000 ppm, based upon the total pressure of the reactor;

ii) wherein the alpha-olefin monomer(s) having 3 to 24 carbon atoms are present at 10 volume % or more based upon the total volume of the catalyst/activator/alkylaluminum compound solutions, monomers, and any diluents or solvents present in the reaction;

iii) the residence time of the reaction is at least 5 minutes;

iv) the productivity of the process is at least 43,000 g of total product per gram of transition metal compound;

v) the process is continuous or semi-continuous, vi) the temperature in the reaction zone does not rise by more than 10° C. during the reaction; and vii) ethylene is not present at more than 30 volume % of the monomers entering the reaction zone; and 2) obtaining a polyalpha-olefin (PAO), optionally hydrogenating the PAO, wherein the PAO comprises at least 50 mole % of a C3 to C24 alpha-olefin monomer, and wherein the PAO has a kinematic viscosity at 100° C. of 20 cSt or less.

DETAILED DESCRIPTION OF THE INVENTION

As used herein, the new numbering scheme for the Periodic Table of the Elements is used as set out in CHEMICAL AND ENGINEERING NEWS, 63(5), 27 (1985).

Unless otherwise stated all pressures in psi are psig.

For purposes of this invention and the claims thereto, when a polymer or oligomer is referred to as comprising an olefin, the olefin present in the polymer or oligomer is the polymerized or oligomerized form of the olefin, respectively. Likewise the use of the term polymer is meant to encompass homopolymers and copolymers, where copolymers include any polymer having two or more chemically distinct monomers. Likewise the use of the term oligomer is meant to encompass homooligomers and cooligomers, where cooligomers include any oligomer or having two or more chemically distinct monomers.

For purposes of this disclosure, the term oligomer refers to compositions having 2-75 mer units and the term polymer refers to compositions having 76 or more mer units. A mer is defined as a unit of an oligomer or polymer that originally corresponded to the olefin(s) used in the oligomerization or polymerization reaction. For example, the mer of polydecene would be decene.

For the purposes of this invention and the claims thereto the term "Polyalpha-olefin," "polyalphaolefin," or "PAO" includes homooligomers, cooligomers, homopolymers and copolymers of C3 or greater alpha-olefin monomers.

For the purposes of this invention and the claims thereto the active species in a catalytic cycle may comprise the neutral or ionic forms of the catalyst.

The term "catalyst system" is defined to mean a catalyst precursor/activator pair, such as a metallocene/activator pair. When "catalyst system" is used to describe such a pair before activation, it means the unactivated catalyst (precatalyst) together with an activator and, optionally, a co-activator (such as a trialkylaluminum compound). When it is used to describe such a pair after activation, it means the activated catalyst and the activator or other charge-balancing moiety. Additionally, the catalyst system may optionally comprise a co-activator and/or other charge-balancing moiety.

"Catalyst precursor" is also often referred to as precatalyst, catalyst, precursor, metallocene, transition metal compound, unactivated catalyst, or transition metal complex. These words are used interchangeably. Activator and cocatalyst are also used interchangeably. A scavenger is a compound that is typically added to facilitate oligomerization or polymerization by scavenging impurities. Some scavengers may also act as activators and may be referred to as co-activators. A co-activator which is not a scavenger may also be used in conjunction with an activator in order to form an active catalyst with a transition metal compound. In some embodiments, a co-activator can be pre-mixed with the transition metal compound to form an alkylated transition metal compound, also referred to as an alkylated catalyst compound or alkylated metallocene.

For purposes of this invention and the claims thereto non-coordinating anion (NCA) is defined to mean an anion which either does not coordinate to the catalyst metal cation or that coordinates only weakly to the metal cation. An NCA coordinates weakly enough that a neutral Lewis base, such as an olefinically or acetylenically unsaturated monomer, can displace it from the catalyst center. Any metal or metalloid that can form a compatible, weakly coordinating complex with the catalyst metal cation may be used or contained in the noncoordinating anion. Suitable metals include, but are not limited to, aluminum, gold, and platinum. Suitable metalloids include, but are not limited to, boron, aluminum, phosphorus, and silicon. A subclass of non-coordinating anions comprises stoichiometric activators, which can be either neutral or ionic. The terms ionic activator, and stoichiometric ionic activator can be used interchangeably. Likewise, the terms neutral stoichiometric activator and Lewis acid activator can be used interchangeably.

In addition, a reactor is any container(s) in which a chemical reaction occurs.

"Isoolefin" is a branched alkene having at least one tertiary or quaternary carbon atom and which possess at least one $C_1$ to $C_{18}$ alkyl branch along at least a portion of each chain. Preferably the alkyl branch is $C_1$ to $C_{12}$.

Polyalpha-Olefins

In a preferred embodiment, this invention relates to liquid polyalpha-olefins (PAO's) comprising more than 50 mole % of one or more C3 to C24 alpha-olefin monomers, preferably 55 mole % or more, preferably 60 mole % or more, preferably 65 mole % or more, preferably 70 mole % or more, preferably 75 mole % or more, preferably 80 mole % or more, preferably 85 mole % or more, preferably 90 mole % or more, preferably 95 mole % or more, preferably 100 mole % based on the total moles of monomers present in the polyalpha-olefin, as measured by Carbon-13 NMR.

For purposes of this invention and the claims thereto, a liquid is defined to be a material that flows at room temperature, having a pour point of less than 25° C., and with no melting point above 0° C. and a kinematic viscosity at 25° C. of 30,000 cSt or less.

In another embodiment, any of the polyalpha-olefins described herein preferably have less than 300 ppm of Group 4 metals (preferably Ti, Hf or Zr), preferably less than 200 ppm, preferably less than 100 ppm, preferably less than 50 ppm, preferably less than 10 ppm, as measured by ASTM 5185.

In another embodiment, any of the polyalpha-olefins described herein preferably have less than 300 ppm of Ti, preferably less than 200 ppm, preferably less than 100 ppm, preferably less than 50 ppm, preferably less than 10 ppm, as measured by ASTM 5185.

In another embodiment, any of the polyalpha-olefins described herein preferably have less than 300 ppm of Hf, preferably less than 200 ppm, preferably less than 100 ppm, preferably less than 50 ppm, preferably less than 10 ppm, as measured by ASTM 5185.

In another embodiment, any of the polyalpha-olefins described herein preferably have less than 300 ppm of Zr, preferably less than 200 ppm, preferably less than 100 ppm, preferably less than 50 ppm, preferably less than 10 ppm, as measured by ASTM 5185.

In another embodiment, any of the polyalpha-olefins described herein preferably have less than 100 ppm of Group 13 metals (preferably B or Al), preferably less than 50 ppm, preferably less than 10 ppm, as measured by ASTM 5185.

In another embodiment, any of the polyalpha-olefins described herein preferably have less than 100 ppm of boron, preferably less than 50 ppm, preferably less than 10 ppm, as measured by ASTM 5185.

In another embodiment, any of the polyalpha-olefins described herein preferably have less than 600 ppm of aluminum, preferably less than 500 ppm, preferably less than 600 ppm, preferably less than 300 ppm, preferably less than 300 ppm, preferably less than 10 ppm, preferably less than 50 ppm, preferably less than 10 ppm, as measured by ASTM 5185.

In another embodiment, any of the polyalpha-olefins described herein preferably have an Mw (weight average molecular weight) of 100,000 or less, preferably between 100 and 80,000, preferably between 250 and 60,000, preferably between 280 and 50,000, preferably between 336 and 40,000 g/mol. (Preferred Mw's include those from 224 to 55,100, preferably from 392 to 30,000, preferably 800 to 24,000, preferably 2,000 to 37,5000 g/mol. Alternately preferred Mw's include 224 to about 6790 and 224 to about 2720).

In another embodiment, any of the polyalpha-olefins described herein preferably have an Mn (number average molecular weight) of 50,000 or less, preferably between 200 and 40,000, preferably between 250 and 30,000, preferably between 500 and 20,000 g/mol. (Preferred Mn's include those from 280 to 10,000, preferably form 280 to 4000. Alternately preferred Mn's include those from 200 to 20,900, preferably 280, to 10,000, preferably 200 to 7000, preferably 200 to 2000, preferably 280 to 2900, preferably 280 to 1700, preferably 200 to 500.)

In another embodiment, any of the polyalpha-olefins described herein preferably have an Mw/Mn of greater than 1 and less than 5, preferably less than 4, preferably less than 3, preferably less than 2.5, preferably less than 2. Alternately any of the polyalpha-olefins described herein preferably have an Mw/Mn of between 1 and 2.5, alternately between 1 and 3.5.

The Mw, Mn and Mz are measured by GPC method using a column for medium to low molecular weight polymers, tetrahydrofuran as solvent and polystyrene as calibration standard, correlated with the fluid viscosity according to a power equation. Unless otherwise indicated Mw values reported herein are GPC values and not calculated from kinematic viscosity at 100° C.

In a preferred embodiment of this invention, any PAO described herein may have a pour point of less than 0° C. (as measured by ASTM D 97), preferably less than −10° C., preferably less than −20° C., preferably less than −25° C., preferably less than −30° C., preferably less than −35° C., preferably less than −40° C., preferably less than −55° C., preferably between −10 and −80° C., preferably between −15° C. and −70° C.

In a preferred embodiment of this invention, any PAO described herein may have a kinematic viscosity (at 40° C. as measured by ASTM D 445) from about 3 to about 1,000 cSt, preferably from about 4 cSt to about 500 cSt at 40° C., alternately from about 4 to about 4 cSt, preferably from about 5 cSt to about 400 cSt, preferably from about 5 cSt to about 300 cSt at 40° C.

In another embodiment according to the present invention, any polyalpha olefin described herein may have a kinematic viscosity at 100° C. from about 1.5 to about 20 cSt, preferably from about 1.7 to about 15 cSt, preferably from about 1.8 cSt to about 12 cSt.

In another embodiment according to the present invention any polyalpha olefin described herein may have a kinematic viscosity at 100° C. from 1.8 to 12 cSt and a flash point of 150° C. or more, preferably 200° C. or more (as measured by ASTM D 56).

In another embodiment according to the present invention any polyalpha olefin described herein may have a dielectric constant of 2.5 or less (1 kHz at 23° C. as determined by ASTM D 924).

In another embodiment according to the present invention any polyalpha olefin described herein may have a specific gravity of 0.75 to 0.96 g/cm$^3$, preferably 0.80 to 0.94 g/cm$^3$.

The PAO's prepared herein, particularly those of low viscosity (such as those with a $KV_{100}$ of 20 cSt or less), are especially suitable for high performance automotive engine oil formulations either by themselves or by blending with other fluids, such as Group II, Group II+, Group III, Group III+ or lube base stocks derived from hydroisomerization of wax fractions from Fisher-Tropsch hydrocarbon synthesis from CO/H2 syn gas, or other Group IV or Group V base stocks. PAOs having $KV_{100}$'s from 3 cSt to 8 cSt are also preferred grades for high performance automotive engine oil or industrial oil formulations.

In another embodiment according to the present invention, any polyalpha olefin described herein may have a viscosity index (VI) of 90 or more, preferably 100 or more, alternately from 100 to 300; alternately from 120 to 280, alternately from 100 to 300, alternately from 140 to 300. For many lower viscosity fluids made from 1-decene or 1-decene equivalent feeds ($KV_{100}$ of 3 to 10 cSt), the preferred VI range is from 90 to 200. Viscosity index is determined according to ASTM Method D 2270-93 [1998].

All kinematic viscosity values reported for fluids herein are measured at 100° C. unless otherwise noted. Dynamic viscosity can then be obtained by multiplying the measured kinematic viscosity by the density of the liquid. The units for kinematic viscosity are in m$^2$/s, commonly converted to cSt or centistokes (1 cSt=10$^{-6}$ m$^2$/s or 1 cSt=1 mm$^2$/sec).

The PAO's produced according to this invention are typically dimers, trimers, tetramers, or higher oligomers of one or more C3 to C24 olefin monomers, preferably one or more C4 to C20 alpha-olefin monomers, preferably one or more C5 to C20 linear alpha-olefin monomers. Alternatively, an alpha-olefin with alkyl substituent at least 2 carbons away from the olefinic double bond can also be used. Typically, the PAO's produced herein are usually a mixture of many different oligomers. The smallest oligomers from these alpha-olefins have carbon number ranging from C10 to C20. These small oligomers are usually separated from the higher oligomers with carbon number of greater than C20, for example C24 and higher which are typically used as high performance fluids. These separated C10 to C20 oligomer olefins or the corresponding paraffins after hydrogenation can be used in specialty applications, such as drilling fluids, solvents, paint thinner, etc with excellent biodegradability, toxicity, viscosities, etc. The high performance fluid fraction in the C20, or C30 and higher fractions typically have lower viscosities making them beneficial for some applications, such as better fuel economy, better biodegradability, better low temperature flow properties, or lower volatility. Because of their usually narrow molecular weight distribution, they have superior shear stability. the PAOs described herein can be further blended with proper additives, including antioxidants, anti-wear additives, friction modifiers, dispersants, detergents, corrosion inhibitors, defoamants, extreme pressure additives, seal swell additives, and optionally viscosity modifiers, etc. Description of typical additives can be found in the book "Lubricant Additives" Chemistry and Applications, ed. L. R. Rudnick, Marcel Dekker, Inc., New York, 2003.

In another embodiment, any of the PAO's described herein may have pour points of less than 0° C., alternately less than −45° C., alternately less than −75° C.

In a preferred embodiment, the PAO's of this invention have a $KV_{100}$ of 1.5-20 cSt and a pour point of less than 0° C., preferably less than −45° C., preferably less than −75° C. Alternately preferred PAO's have $KV_{100}$ of 1.5-15 cSt and a pour point of less than 0° C., preferably less than −45° C., preferably less than −75° C. In another preferred embodiment, the PAO's of this invention have a $KV_{100}$ of 1.5 to 10 cSt and a pour point of less than 0° C., preferably less than −45° C., preferably less than −75° C.

In another embodiment, the PAO's produced herein have a volatility as measured by Noack Volatility test (ASTM D5800) of 25 wt % or less, preferably 20 wt % or less, preferably 14 wt % or less.

In another embodiment, the PAO's produced herein have a Bromine number of 1.8 or more.

The PAOs produced herein are liquids. For purposes of this invention and the claims thereto, a liquid is defined to be a material that flows at room temperature, having a pour point of less than 25° C., and with no melting point above 0° C. and a kinematic viscosity at 25° C. of 30,000 cSt or less.

In a preferred embodiment, the product produced herein has a selectivity of 80% or more for C20 and greater hydrocarbons, preferably 85% or more, preferably 90% or more, more preferably 95% or more, preferably 98% or more, preferably 99% or more for C20 and greater hydrocarbons.

In a preferred embodiment, the productivity of the process is at least 43,000 g of total product per gram of transition metal compound, preferably at least 45,000 g of total product per gram of transition metal compound, preferably at least 50,000 g of total product per gram of transition metal compound, preferably at least 55,000 g of total product per gram of transition metal compound, preferably at least 60,000 g of total product per gram of transition metal compound, preferably at least 75,000 g of total product per gram of transition metal compound, preferably at least 100,000 g of total product per gram of transition metal compound.

In a preferred embodiment, the product produced herein has a selectivity of 60% or less for C20 or less hydrocarbons, preferably 50% or less, preferably 40% or less, more preferably 20% or less, preferably 10% or less, preferably 5% or less for C20 or less hydrocarbons (% by weight unless otherwise noted).

In a preferred embodiment, the product produced herein has a selectivity of 60% or less for C10 dimer, preferably 50% or less, preferably 40% or less, more preferably 30% or less for C10 dimer (% by weight unless otherwise noted).

Process

This invention relates to an improved process to produce poly-alpha-olefins. This improved process employs metallocene catalysts together with one or more non-coordinating anion activators. The metallocene catalysts are unbridged, substituted bis cyclopentadienyl transition metal compounds. One preferred class of catalysts are highly substituted metallocenes that give high catalyst productivity and with low product viscosity. Another preferred class of metallocenes are unbridged and substituted cyclopentadienes, including unbridged and substituted or unsubstituted indenes and or flourenes. One aspect of the processes described herein also includes treatment of the feed olefins to remove catalyst poisons, such as peroxides, oxygen, sulfur, nitrogen-containing organic compounds, and or acetylenic compounds. This treatment is believed to increase catalyst productivity, typically more than 5 fold, preferably more than 10 fold.

In a preferred embodiment, this invention relates to a continuous or semi-continuous process to produce a polyalphaolefin comprising:

1) contacting at least one alpha-olefin monomer, (whether a single monomer type or a mixture of two or more monomers), having 3 to 24 carbon atoms with an unbridged substituted bis cyclopentadienyl transition metal compound having: 1) at least one non-isoolefin substitution on each cyclopentadienyl ring, or 2) at least two substitutions on at least one cyclopentadienyl ring, preferably having at least two substitutions on each cyclopentadienyl ring, a non-coordinating anion activator, and optionally an alkyl-aluminum compound, where the molar ratio of transition metal compound to activator is 10:1 to 0.1:1, and if the alkyl aluminum compound is present then the molar ratio of alkyl aluminum compound to transition metal compound is 1:4 to 4000:1, under polymerization conditions wherein hydrogen is present at a partial pressure of 50 psi (345 kPa) or less, based upon the total pressure of the reactor (preferably between 1 psi (7 kPa) and 50 psi, preferably between 3 psi (20 kPa) and 40 psi (276 kPa), preferably between 5 psi (35 kPa) and 30 psi (207 kPa), preferably 25 psi (173 kPa) or less, preferably 10 psi (69 kPa) or less, or hydrogen is present at a concentration of 10 to 10,000 ppm by weight, preferably 25 to 7,500 ppm, preferably 25 to 5,000 ppm, and wherein the alpha-olefin monomer(s) having 3 to 24 carbon atoms are present at 10 volume % or more based upon the total volume of the catalyst/activator/co-activator solutions, monomers, and any diluents or solvents present in the reaction and ethylene is not present at more than 30 volume % of the monomers entering the reaction zone, wherein the residence time of the reaction is at least 5 minutes, and the temperature in the reaction zone does not rise by more than 10° C. during the reaction; and 2) obtaining a polyalpha-olefin (PAO), optionally hydrogenating the PAO, and obtaining a PAO, comprising at least 50 mole % of a C3 to C24 alpha-olefin monomer, wherein the polyalpha-olefin has a kinematic viscosity at 100° C. of 20 cSt or less (preferably 15 cSt or less), and preferably a pour point of 0° C. or less;

wherein the productivity of the process is at least 43,000 g of total product per grams of transition metal compound.

In a preferred embodiment, this invention relates to a process to produce a liquid poly-alpha-olefin having a $KV_{100}$ of 20 cSt or less comprising:

a) contacting in a reaction zone, in the presence of hydrogen (preferably from 10 to 10,000 ppm by weight of hydrogen), one or more C3 to C20 alpha-olefin monomers with a non-coordinating anion activator and a transition metal compound represented by the formula:

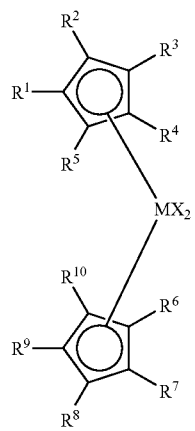

where M is a Group 4 metal preferably titanium, zirconium or hafnium, preferably zirconium or hafnium, each X is a hydrogen, halogen, hydride radicals, hydrocarbyl radicals, substituted hydrocarbyl radicals, halocarbyl radicals, substituted halocarbyl radicals, silylcarbyl radicals, substituted silylcarbyl radicals, germylcarbyl radicals, or substituted germylcarbyl radicals; or both X are joined and bound to the metal atom to form a metallacycle ring containing from about 3 to about 20 carbon atoms; or both together can be an olefin, diolefin or aryne ligand;

and $R^1$ to $R^{10}$ are independently, a radical group which is a hydrocarbyl, substituted hydrocarbyl, halocarbyl, substituted halocarbyl, silylcarbyl or germylcarbyl, (preferably hydrogen, or a $C_1$ to $C_{20}$ hydrocarbyl, a substituted $C_1$ to $C_{20}$ hydrocarbyl, or a heteroatom), provided that: 1) at least one of $R^1$ to $R^5$ is not hydrogen or an isoolefin and at least one of $R^6$ to $R^{10}$ is not hydrogen or an isoolefin, or 2) at least two of $R^1$ to $R^5$ are not hydrogen, (and preferably at least two of $R^6$ to $R^{10}$ are not hydrogen) where any two adjacent $R^1$ to $R^5$ groups may form a C4 to C20 cyclic or polycyclic moiety (such as substituted or unsubstituted indene or substituted or unsubstituted flourene), and where any two adjacent $R^6$ to $R^{10}$ groups may form a C4 to C20 cyclic or poly cyclic moiety (such as substituted or unsubstituted indene or substituted or unsubstituted flourene), and provided that ethylene is not present at more than 30 volume % of the monomers entering the reaction zone, where:

i) the productivity of the process is at least 43,000 g of total product per grams of transition metal compound, and
ii) the process is continuous or semi-continuous, and
iii) the temperature in the reaction zone does not rise by more than 10° C. during the reaction (preferably not more than 7° C., preferably not more than 5° C., preferably not more than 3° C.); and b) obtaining a liquid poly-alpha-olefin having a $KV_{100}$ of 20 cSt or less.

By continuous is meant a system that operates (or is intended to operate) without interruption or cessation. For example a continuous process to produce a polymer would be one where the reactants (such as monomers and catalyst components) are continually introduced into one or more reactors and polymer product is continually withdrawn. By semi-continuous is meant a system that operates (or is intended to operate) with periodic interruption. For example a semi-continuous process to produce a polymer would be one where the reactants (such as monomers and catalyst components) are continually introduced into one or more reactors and polymer product is intermittently withdrawn.

A batch process is not continuous or semi-continuous.

In a preferred embodiment of this invention the oligomerization reaction temperature is controlled by several means, such as continuous or semi-continuous operation, by heat removal, rate of catalyst or feed addition or solvent addition. Since catalyst solution, feed olefins and/or solvents are usually at room or ambient temperature, their addition to the reactor can mitigate the heat of reaction and can help maintain constant reaction temperature. This mode of operation can control the temperature to within 110° C. of desired reaction temperature, usually preferred to be within 7° C. of desired temperature, preferred to be within 5° C. of desired temperature or preferred to be within 3° C. of desired temperature over a 30 minute period, preferably for the entire reaction. Usually, a reactor, containing a small amount of starting liquid is pre-heated to within 10° C. of the desired reaction temperature in a semi-continuous run. This starting liquid can be feed olefins, catalyst components, solvents or polyalpha-olefins heels from previous runs, or polyalpha-olefin products from previous runs or any other appropriate liquids. Usually, part of the feed olefins, solvent or PAO heels from previous runs or PAO products from previous runs are more preferred starting liquid. When the reactor is at desired temperature, feed olefins, catalyst components, hydrogen of proper amount, solvents and other components were added continuously at proper rates. Usually in a semi-continuously run, the range of addition for the catalyst solution and the feed olefins are controlled so that addition of both streams are completed at the same time. As the polymerization reaction starts at the reaction temperature, heat is released. In order to control the reaction temperature to be as constant as possible, heat removal by several methods as mentioned above is employed. Or if the reaction rate is not high enough to maintain the reaction temperature, external heating is supplied to the reactor to maintain a desired temperature. After addition is completed, the reaction is allowed to proceed for the desired amount of time to obtain highest feed olefin conversion.

In a continuous mode of operation, the operation is similar to the semi-continuous run, except when the reactor is filled up to a pre-determined level, a pre-determined amount of reaction product is withdrawn from the reactor while the addition of all components is continued. The rate of feed addition and the amount of reaction product withdrawn from the reactor determine the reaction time or residence time. This can be pre-determined to obtain high feed olefin conversion and high reactor throughput for economical operation.

In this process, several factors are critical for optimum results. First is the proper choice of catalyst components. An unabridged, substituted metallocene activated by a non-coordinating anion (NCA) with small amount of trialkylaluminum is an effective catalyst. The metallocene components can be dihalide (preferably dichloride) or dialkyls. But, usually, the di-alkyl form of the metallocene is the more preferred catalyst for use in combination with an NCA. When the metallocene di-halide is used, it typically requires addition of tri-alkylaluminum to promote the reaction. In this case the molar ratio of tri-alkylaluminum to metallocene is anywhere from 4 to 4000, preferably 8 to 500. When the metallocene dialkyls are used, (such as bis(tetrahydroindentyl) zirconium dimethyl, bis(1,2-dimethylcyclopentadienyl) zirconium dimethyl, bis(1,3-dimethylcyclopentadienyl) zirconium dimethyl, bis(1,2,4-trimethylcyclopentadienyl) zirconium dimethyl, bis(tetramethylcyclopentadienyl)zirconium dimethyl or bis(methyl-3-n-butycyclopentadienyl)zirconium dimethyl, or many other dialkyl metallocenes, etc.), a small amount of tri-alkylaluminums is needed to give the optimum catalyst productivity. In this case the molar ratio of trialkylaluminum to metallocene is typically 2 to 500, preferably 3 to 200, more preferably 3 to 100 or 3 to 10. The amount of NCA used is also critical. The molar ratio of metallocene to NCA can ranged from 10 to 0.1. The more preferred molar ratio of metallocene to NCA is close to 1 to 1 or 0.5 to 2.

In addition, the amount of metallocene concentration is critical. In order to achieve the highest catalyst productivity, highest selectivity to lube range product and best temperature control and operability, the preferred amount of metallocene per gram of olefin feeds ranges from 1 microgram (or 0.001 milligram)/gram to 1 milligram/gram of olefins. When amounts of catalyst components used are too high, the temperature control becomes difficult, product selectivity suffers and catalyst cost becomes un-economical.

The amount of hydrogen present in the reactor is also important. Usually smaller amount of hydrogen is preferred. The hydrogen head pressure is usually maintained at below 100 psi, preferably below 50 psi, preferably below 30 psi, preferably below 20 psi, preferably below 10 psi. Usually, lower hydrogen pressure while maintaining an activity boost is preferred. Too high a hydrogen pressure will hydrogenate the starting alpha-olefin feeds into corresponding alkane. When this hydrogenation of raw material occurs, the product yield and selectivity will suffer significantly. Therefore, it is preferred to maintain reactor hydrogen pressure below 100 psi, more preferably below 50 psi to minimize the hydrogenation of feed stock into low value alkanes. Likewise a minimum amount of hydrogen is also desired, preferably the hydrogen is present at least 1 psi, preferably at least 5 psi.

The reaction time or residence time is also important for high conversion of the feed olefins. Usually longer reaction time or residence time favors higher feed olefin conversion. However, to balance high conversion and the high reactor throughput, the reaction time or residence time is usually between 5 minutes to 30 hours, more preferred 10 minutes to 16 hours, more preferred 20 minutes to 10 hours.

By proper choice of metallocenes, activated with NCA, and by proper choice of reaction operation conditions, including the amount of catalyst used, and with right amount of trialkylaluminum as scavenger, residence time or reaction time, and amount of hydrogen, we produce polyalpha-olefins with high catalyst productivity of more than 43,000 gram total product per gram of metallocene used. This high productivity makes the process economically and commercially attractive.

In an alternate embodiment, the feed alpha-olefin, diluent or solvent stream comprises less than 300 ppm of heteroatom containing compounds.

After the reaction is completed in the semi-continuous run or the product withdrawn from the continuous run, the crude product can be worked up by deactivating the catalyst by addition of small amount of oxygen, $CO_2$ gas, air, water, alcohol, acids or any other catalyst poison agents; washing the product with dilute aqueous sodium hydroxide or hydrochloric acid solution and water; and separating the organic layer. The organic layer typically contains un-reacted olefins, olefin oligomers and solvent. The product fractions can be separated from solvent and un-reacted starting olefins by distillation. The product fractions can be further fractionated into light fractions and residual fractions. These fractions typically have unsaturated double bond per each molecule. The double bonds are mostly vinylidene with some 1,2-disubstituted olefins or tri-substituted olefins. These double bonds are suitable for further functionalization into other functional fluids or performance additives according to well-known olefin functionalization reaction, such as alkylation with aromatic containing compounds, with maleic anhydrides, with $CO/H_2$ via hydroformulation reactions, etc. The residual fractions, usually have low or no light hydrocarbons with less than 24 carbons can be used as high performance fluids if their bromine number is below 2. If the bromine number is above 2, it can be readily hydrogenated by conventional lube hydrofinishing process and converted into fully saturated paraffin fluids with bromine number less than 2, usually significantly less than 2. Usually, lower bromine number is more preferred, as it indicate better oxidative stability. These hydrogenated, saturated hydrocarbon paraffins are used as high performance lubricant base stocks or used as high performance functional fluids after proper formulation. Description of the typical lubricant or functional fluids formulation can be found in the book and the references in "Synthetic Lubricants and High-Performance Functional Fluids", $2^{nd}$ edition, ed. by L. R. Rudnick and R. L. Shubkin, Marcel Dekker, Inc., N.Y. 1999.

Alternatively, the crude product from the polymerization reactor can be worked up by absorbing the catalyst components and scavenger components and any other heteroatom containing components using a solid sorbant. This is a preferred method and is used in the examples below. In this method, a catalyst de-activator as described above is added to the crude reaction product or a solid absorbent, such as alumina, acid clay, Celite, or a cheap filter aid, is added to the crude product and stirred for a pre-determined amount of time, usually greater than 5 minutes. Then the solid is filtered and the filtrate is ready for further distillation or fractionation. This method is described more fully in concurrently filed patent application U.S. Ser. No. 60/831,995, filed Jul. 19, 2006.

In another embodiment, the process further comprises contacting PAO produced herein with hydrogen under typical hydrogenation conditions with hydrogenation catalyst.

Metallocene Catalyst Compounds

For purposes of this invention and the claims thereto, the terms "hydrocarbyl radical," "hydrocarbyl," and hydrocarbyl group" are used interchangeably throughout this document. Likewise the terms "group," "radical," and "substituent" are also used interchangeably throughout this document. For purposes of this disclosure, "hydrocarbyl radical" is defined to be a $C_1$-$C_{100}$ radical and may be linear, branched, or cyclic. When cyclic, the hydrocarbon radical may be aromatic or non-aromatic. "Hydrocarbon radical" is defined to include substituted hydrocarbyl radicals, halocarbyl radicals, substituted halocarbyl radicals, silylcarbyl radicals, and germylcarbyl radicals as these terms are defined below. Substituted hydrocarbyl radicals are radicals in which at least one hydrogen atom has been substituted with at least one functional group such as $NR^*_2$, $OR^*$, $SeR^*$, $TeR^*$, $PR^*_2$, $AsR^*_2$, $SbR^*_2$, $SR^*$, $BR^*_2$, $SiR^*_3$, $GeR^*_3$, $SnR^*_3$, $PbR^*_3$ and the like or where at least one non-hydrocarbon atom or group has been inserted within the hydrocarbyl radical, such as —O—, —S—, —Se—, —Te—, —N(R*)—, =N—, —P(R*)—, =P—, —As(R*)—, =As—, —Sb(R*)—, =Sb—, —B(R*)—, =B—, —Si(R*)$_2$—, —Ge(R*)$_2$—, —Sn(R*)$_2$—, —Pb(R*)$_2$— and the like, where R* is independently a hydrocarbyl or halocarbyl radical, and two or more R* may join together to form a substituted or unsubstituted saturated, partially unsaturated or aromatic cyclic or polycyclic ring structure.

Halocarbyl radicals are radicals in which one or more hydrocarbyl hydrogen atoms have been substituted with at least one halogen (e.g. F, Cl, Br, I) or halogen-containing group (e.g. $CF_3$).

Substituted halocarbyl radicals are radicals in which at least one halocarbyl hydrogen or halogen atom has been substituted with at least one functional group such as $NR^*_2$, $OR^*$, $SeR^*$, $TeR^*$, $PR^*_2$, $AsR^*_2$, $SbR^*_2$, $SR^*$, $BR^*_2$, $SiR^*_3$, $GeR^*_3$, $SnR^*_3$, $PbR^*_3$ and the like or where at least one non-carbon atom or group has been inserted within the halocarbyl radical such as —O—, —S—, —Se—, —Te—, —N(R*)—, =N—, —P(R*)—, =P—, —As(R*)—, =As—, —Sb(R*)—, =Sb—, —B(R*)—, =B—, —Si(R*)$_2$—, —Ge(R*)$_2$—, —Sn(R*)$_2$—, —Pb(R*)$_2$— and the like, where R* is independently a hydrocarbyl or halocarbyl radical provided that at least one halogen atom remains on the original halocarbyl radical. Additionally, two or more R* may join together to form a substituted or unsubstituted saturated, partially unsaturated or aromatic cyclic or polycyclic ring structure.

Silylcarbyl radicals (also called silylcarbyls) are groups in which the silyl functionality is bonded directly to the indicated atom or atoms. Examples include $SiH_3$, $SiH_2R^*$, $SiHR^*_2$, $SiR^*_3$, $SiH_2(OR^*)$, $SiH(OR^*)_2$, $Si(OR^*)_3$, $SiH_2(NR^*_2)$, $SiH(NR^*_2)_2$, $Si(NR^*_2)_3$, and the like where R* is independently a hydrocarbyl or halocarbyl radical and two or more R* may join together to form a substituted or unsubstituted saturated, partially unsaturated or aromatic cyclic or polycyclic ring structure.

Germylcarbyl radicals (also called germylcarbyls) are groups in which the germyl functionality is bonded directly to the indicated atom or atoms. Examples include $GeH_3$, $GeH_2R^*$, $GeHR^*_2$, $GeR^5_3$, $GeH_2(OR^*)$, $GeH(OR^*)_2$, $Ge(OR^*)_3$, $GeH_2(NR^*_2)$, $GeH(NR^*_2)_2$, $Ge(NR^*_2)_3$, and the like where R* is independently a hydrocarbyl or halocarbyl radical and two or more R* may join together to form a substituted or unsubstituted saturated, partially unsaturated or aromatic cyclic or polycyclic ring structure.

Polar radicals or polar groups are groups in which a heteroatom functionality is bonded directly to the indicated atom or atoms. They include heteroatoms of groups 1-17 of the periodic table (except carbon and hydrogen) either alone or connected to other elements by covalent bonds or other interactions such as ionic bonds, van der Waals forces, or hydrogen bonding. Examples of functional heteroatom containing groups include carboxylic acids, acid halides, carboxylic esters, carboxylic salts, carboxylic anhydrides, aldehydes and their chalcogen (Group 14) analogues, alcohols and phenols, ethers, peroxides and hydroperoxides, carboxylic amides, hydrazides and imides, amidines and other nitrogen analogues of amides, nitriles, amines and imines, azos, nitros, other nitrogen compounds, sulfur acids, selenium acids, thiols, sulfides, sulfoxides, sulfones, phosphines, phosphates, other phosphorus compounds, silanes, boranes, borates, alanes, aluminates. Functional groups may also be taken broadly to include organic polymer supports or inorganic support material such as alumina, and silica. Preferred examples of polar groups include $NR^*_2$, $OR^*$, $SeR^*$, $TeR^*$, $PR^*_2$, $AsR^*_2$, $SbR^*_2$, $SR^*$, $BR^*_2$, $SnR^*_3$, $PbR^*_3$ and the like where R* is independently a hydrocarbyl, substituted hydrocarbyl, halocarbyl or substituted halocarbyl radical as defined above and two R* may join together to form a substituted or unsubstituted saturated, partially unsaturated or aromatic cyclic or polycyclic ring structure.

In using the terms "substituted or unsubstituted cyclopentadienyl ligand", "substituted or unsubstituted indenyl ligand", "substituted or unsubstituted fluorenyl ligand" and "substituted or unsubstituted tetrahydroindenyl ligand", the substitution to the aforementioned ligand may be hydrocarbyl, substituted hydrocarbyl, halocarbyl, substituted halocarbyl, silylcarbyl, or germylcarbyl. The substitution may also be within the ring giving heterocyclopentadienyl ligands, heteroindenyl ligands, heterofluorenyl ligands, or heterotetrahydoindenyl ligands, each of which can additionally be substituted or unsubstituted.

In some embodiments, the hydrocarbyl radical is independently selected from methyl, ethyl, ethenyl, and isomers of propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, heneicosyl, docosyl, tricosyl, tetracosyl, pentacosyl, hexacosyl, heptacosyl, octacosyl, nonacosyl, triacontyl, propenyl, butenyl, pentenyl, hexenyl, heptenyl, octenyl, nonenyl, decenyl, undecenyl, dodecenyl, tridecenyl, tetradecenyl, pentadecenyl, hexadecenyl, heptadecenyl, octadecenyl, nonadecenyl, eicosenyl, heneicosenyl, docosenyl, tricosenyl, tetracosenyl, pentacosenyl, hexacosenyl, heptacosenyl, octacosenyl, nonacosenyl, triacontenyl, propynyl, butynyl, pentynyl, hexynyl, heptynyl, octynyl, nonynyl, decynyl, undecynyl, dodecynyl, tridecynyl, tetradecynyl, pentadecynyl, hexadecynyl, heptadecynyl, octadecynyl, nonadecynyl, eicosynyl, heneicosynyl, docosynyl, tricosynyl, tetracosynyl, pentacosynyl, hexacosynyl, heptacosynyl, octacosynyl, nonacosynyl, triacontynyl, butadienyl, pentadienyl, hexadienyl, heptadienyl, octadienyl, nonadienyl, and decadienyl. Also included are isomers of saturated, partially unsaturated and aromatic cyclic and polycyclic structures wherein the radical may additionally be subjected to the types of substitutions described above. Examples include phenyl, methylphenyl, dimethylphenyl, ethylphenyl, diethylphenyl, propylphenyl, dipropylphenyl, benzyl, methylbenzyl, naphthyl, anthracenyl, cyclopentyl, cyclopentenyl, cyclohexyl, cyclohexenyl, methylcyclohexyl, cycloheptyl, cycloheptenyl, norbornyl, norbornenyl, adamantyl and the like. For this disclosure, when a radical is listed, it indicates that radical type and all other radicals formed when that radical type is subjected to the substitutions defined above. Alkyl, alkenyl and alkynyl radicals listed include all isomers including where appropriate cyclic isomers, for example, butyl includes n-butyl, 2-methylpropyl, 1-methylpropyl, tert-butyl, and cyclobutyl (and analogous substituted cyclopropyls); pentyl includes n-pentyl, cyclopentyl, 1-methylbutyl, 2-methylbutyl, 3-methylbutyl, 1-ethylpropyl, and neopentyl (and analogous substituted cyclobutyls and cyclopropyls); butenyl includes E and Z forms of 1-butenyl, 2-butenyl, 3-butenyl, 1-methyl-1-propenyl, 1-methyl-2-propenyl, 2-methyl-1-propenyl and 2-methyl-2-propenyl (and cyclobutenyls and cyclopropenyls). Cyclic compound having substitutions include all isomer forms, for example, methylphenyl would include ortho-methylphenyl, meta-methylphenyl and para-methylphenyl; dimethylphenyl would include 2,3-dimethylphenyl, 2,4-dimethylphenyl, 2,5-dimethylphenyl, 2,6-diphenylmethyl, 3,4-dimethylphenyl, and 3,5-dimethylphenyl. Examples of cyclopentadienyl and indenyl ligands are illustrated below as anionic ligands.

A "ring carbon atom" is a carbon atom that is part of a cyclic ring structure. By this definition, an indenyl ligand has nine ring carbon atoms; a cyclopentadienyl ligand has five ring carbon atoms and a flourenyl ligand has 13 carbon atoms. Thus an indene is equivalent to a Cp ring with two alkyl radical substituents and a flourene is equivalent to a Cp ring with four alkyl radical substituents.

The metallocene compounds (pre-catalysts), useful herein are preferably cyclopentadienyl derivatives of titanium, zirconium and hafnium. In general, useful titanocenes, zirconocenes and hafnocenes may be represented by the following formulae:

$$(CpCp^*)MX_1X_2 \quad (2)$$

wherein:
M is the metal center, and is a Group 4 metal preferably titanium, zirconium or hafnium, preferably zirconium or hafnium;
Cp and Cp* are the same or different cyclopentadienyl rings that are each bonded to M, and 1) both Cp and Cp* are substituted with at least one non-isoolefin substituent", or 2) Cp is substituted with from two to five substituents "R", preferably both Cp and Cp* are substituted with from two to five substituents "R", each substituent group R being, independently, a radical group which is a hydrocarbyl, substituted hydrocarbyl, halocarbyl, substituted halocarbyl, silylcarbyl or germylcarbyl, or Cp and Cp* are the same or different cyclopentadienyl rings in which any two adjacent R groups are optionally joined to form a substituted or unsubstituted, saturated, partially unsaturated, or aromatic cyclic or polycyclic substituent;
$X_1$ and $X_2$ are, independently, hydrogen, halogen, hydride radicals, hydrocarbyl radicals, substituted hydrocarbyl radicals, halocarbyl radicals, substituted halocarbyl radicals, silylcarbyl radicals, substituted silylcarbyl radicals, germylcarbyl radicals, or substituted germylcarbyl radicals; or both X are joined and bound to the metal atom to form a metallacycle ring containing from about 3 to about 20 carbon atoms; or both together can be an olefin, diolefin or aryne ligand.

Table A depicts representative constituent moieties for the metallocene components of formula 2. The list is for illustrative purposes only and should not be construed to be limiting in any way. A number of final components may be formed by permuting all possible combinations of the constituent moieties with each other. When hydrocarbyl radicals including alkyl, alkenyl, alkynyl, cycloalkyl, cycloalkenyl, cycloalkynyl and aromatic radicals are disclosed in this application the term includes all isomers. For example, butyl includes n-butyl, 2-methylpropyl, 1-methylpropyl, tert-butyl, and cyclobutyl; pentyl includes n-pentyl, 1-methylbutyl, 2-methylbutyl, 3-methylbutyl, 1-ethylpropyl, neopentyl, cyclopentyl and methylcyclobutyl; butenyl includes E and Z forms of 1-butenyl, 2-butenyl, 3-butenyl, 1-methyl-1-propenyl, 1-methyl-2-propenyl, 2-methyl-1-propenyl and 2-methyl-2-propenyl. This includes when a radical is bonded to another group, for example, propylcyclopentadienyl include n-propylcyclopentadienyl, isopropylcyclopentadienyl and cyclopropylcyclopentadienyl. In general, the ligands or groups illustrated in Table A include all isomeric forms. For example, dimethylcyclopentadienyl includes 1,2-dimethylcyclopentadienyl and 1,3-dimethylcyclopentadienyl; methylindenyl includes 1-methylindenyl, 2-methylindenyl, 3-methylindenyl, 4-methylindenyl, 5-methylindenyl, 6-methylindenyl and 7-methylindenyl; methylethylphenyl includes ortho-methylethylphenyl, meta-methylethylphenyl and para-methylethylphenyl. To illustrate members of the transition metal component, select any combination of the species listed in Tables A.

TABLE A

| M | Cp, Cp* |
|---|---|
| titanium | cyclopentadienyl |
| zirconium | methylcyclopentadienyl |
| hafnium | dimethylcyclopentadienyl |
| | trimethylcyclopentadienyl |
| | tetramethylcyclopentadienyl |
| | ethylcyclopentadienyl |
| | diethylcyclopentadienyl |
| | propylcyclopentadienyl |
| | dipropylcyclopentadienyl |
| | butylcyclopentadienyl |
| | dibutylcyclopentadienyl |
| | pentylcyclopentadienyl |
| | dipentylcyclopentadienyl |
| | hexylcyclopentadienyl |
| | dihexylcyclopentadienyl |
| | heptylcyclopentadienyl |
| | diheptylcyclopentadienyl |
| | octylcyclopentadienyl |
| | dioctylcyclopentadienyl |
| | nonylcyclopentadienyl |
| | dinonylcyclopentadienyl |
| | decylcyclopentadienyl |
| | didecylcyclopentadienyl |
| | undecylcyclopentadienyl |
| | dodecylcyclopentadienyl |
| | tridecylcyclopentadienyl |
| | tetradecylcyclopentadienyl |
| | pentadecylcyclopentadienyl |
| | hexadecylcyclopentadienyl |
| | heptadecylcyclopentadienyl |
| | octadecylcyclopentadienyl |
| | nonadecylcyclopentadienyl |
| | eicosylcyclopentadienyl |
| | heneicosylcyclopentadienyl |
| | docosylcyclopentadienyl |
| | tricosylcyclopentadienyl |
| | tetracosylcyclopentadienyl |

TABLE A-continued

| M | Cp, Cp* |
|---|---|
| | pentacosylcyclopentadienyl |
| | hexacosylcyclopentadienyl |
| | heptacosylcyclopentadienyl |
| | octacosylcyclopentadienyl |
| | nonacosylcyclopentadienyl |
| | triacontylcyclopentadienyl |
| | cyclohexylcyclopentadienyl |
| | phenylcyclopentadienyl |
| | diphenylcyclopentadienyl |
| | triphenylcyclopentadienyl |
| | tetraphenylcyclopentadienyl |
| | tolylcyclopentadienyl |
| | benzylcyclopentadienyl |
| | phenethylcyclopentadienyl |
| | cyclohexylmethylcyclopentadienyl |
| | napthylcyclopentadienyl |
| | methylphenylcyclopentadienyl |
| | methyltolylcyclopentadienyl |
| | methylethylcyclopentadienyl |
| | methylpropylcyclopentadienyl |
| | methylbutylcyclopentadienyl |
| | methylpentylcyclopentadienyl |
| | methylhexylcyclopentadienyl |
| | methylheptylcyclpentadienyl |
| | methyloctylcyclopentadienyl |
| | methylnonylcyclopentadienyl |
| | methyldecylcyclopentadienyl |
| | vinylcyclopentadienyl |
| | propenylcyclopentadienyl |
| | butenylcyclopentadienyl |
| | indenyl |
| | methylindenyl |
| | dimethylindenyl |
| | trimethylindenyl |
| | tetramethylindenyl |
| | pentamethylindenyl |
| | methylpropylindenyl |
| | dimethylpropylindenyl |
| | methyldipropylindenyl |
| | methylethylindenyl |
| | methylbutylindenyl |
| | ethylindenyl |
| | propylindenyl |
| | butylindenyl |
| | pentylindenyl |
| | hexylindenyl |
| | heptylindenyl |
| | octylindenyl |
| | nonylindenyl |
| | decylindenyl |
| | phenylindenyl |
| | (fluorophenyl)indenyl |
| | (methylphenyl)indenyl |
| | biphenylindenyl |
| | (bis(trifluoromethyl)phenyl)indenyl |
| | napthylindenyl |
| | phenanthrylindenyl |
| | benzylindenyl |
| | benzindenyl |
| | cyclohexylindenyl |
| | methylphenylindenyl |
| | ethylphenylindenyl |
| | propylphenylindenyl |
| | methylnapthylindenyl |
| | ethylnapthylindenyl |
| | propylnapthylindenyl |
| | (methylphenyl)indenyl |
| | (dimethylphenyl)indenyl |
| | (ethylphenyl)indenyl |
| | (diethylphenyl)indenyl |
| | (propylphenyl)indenyl |
| | (dipropylphenyl)indenyl |
| | methyltetrahydroindenyl |
| | ethyltetrahydroindenyl |
| | propyltetrahydroindenyl |
| | butyltetrahydroindenyl |
| | phenyltetrahydroindenyl |
| | (diphenylmethyl)cyclopentadienyl |
| | trimethylsilylcyclopentadienyl |
| | triethylsilylcyclopentadienyl |
| | trimethylgermylcyclopentadienyl |
| | trifluromethylcyclopentadienyl |
| | cyclopenta[b]thienyl |
| | cyclopenta[b]furanyl |
| | cyclopenta[b]selenophenyl |
| | cyclopenta[b]tellurophenyl |
| | cyclopenta[b]pyrrolyl |
| | cyclopenta[b]phospholyl |
| | cyclopenta[b]arsolyl |
| | cyclopenta[b]stibolyl |
| | methylcyclopenta[b]thienyl |
| | methylcyclopenta[b]furanyl |
| | methylcyclopenta[b]selenophenyl |
| | methylcyclopenta[b]tellurophenyl |
| | methylcyclopenta[b]pyrrolyl |
| | methylcyclopenta[b]phospholyl |
| | methylcyclopenta[b]arsolyl |
| | methylcyclopenta[b]stibolyl |
| | dimethylcyclopenta[b]thienyl |
| | dimethylcyclopenta[b]furanyl |
| | dimethylcyclopenta[b]pyrrolyl |
| | dimethylcyclopenta[b]phospholyl |
| | trimethylcyclopenta[b]thienyl |
| | trimethylcyclopenta[b]furanyl |
| | trimethylcyclopenta[b]pyrrolyl |
| | trimethylcyclopenta[b]phospholyl |
| | ethylcyclopenta[b]thienyl |
| | ethylcyclopenta[b]furanyl |
| | ethylcyclopenta[b]pyrrolyl |
| | ethylcyclopenta[b]phospholyl |
| | diethylcyclopenta[b]thienyl |
| | diethylcyclopenta[b]furanyl |
| | diethylcyclopenta[b]pyrrolyl |
| | diethylcyclopenta[b]phospholyl |
| | triethylcyclopenta[b]thienyl |
| | triethylcyclopenta[b]furanyl |
| | triethylcyclopenta[b]pyrrolyl |
| | triethylcyclopenta[b]phospholyl |
| | propylcyclopenta[b]thienyl |
| | propylcyclopenta[b]furanyl |
| | propylcyclopenta[b]pyrrolyl |
| | propylcyclopenta[b]phospholyl |
| | dipropylcyclopenta[b]thienyl |
| | dipropylcyclopenta[b]furanyl |
| | dipropylcyclopenta[b]pyrrolyl |
| | dipropylcyclopenta[b]phospholyl |
| | tripropylcyclopenta[b]thienyl |
| | tripropylcyclopenta[b]furanyl |
| | tripropylcyclopenta[b]pyrrolyl |
| | tripropylcyclopenta[b]phospholyl |
| | butylcyclopenta[b]thienyl |
| | butylcyclopenta[b]furanyl |
| | butylcyclopenta[b]pyrrolyl |
| | butylcyclopenta[b]phospholyl |
| | dibutylcyclopenta[b]thienyl |
| | dibutylcyclopenta[b]furanyl |
| | dibutylcyclopenta[b]pyrrolyl |
| | dibutylcyclopenta[b]phospholyl |
| | tributylcyclopenta[b]thienyl |
| | tributylcyclopenta[b]furanyl |
| | tributylcyclopenta[b]pyrrolyl |
| | tributylcyclopenta[b]phospholyl |
| | ethylmethylcyclopenta[b]thienyl |
| | ethylmethylcyclopenta[b]furanyl |
| | ethylmethylcyclopenta[b]pyrrolyl |
| | ethylmethylcyclopenta[b]phospholyl |
| | methylpropylcyclopenta[b]thienyl |
| | methylpropylcyclopenta[b]furanyl |
| | methylpropylcyclopenta[b]pyrrolyl |
| | methylpropylcyclopenta[b]phospholyl |
| | butylmethylcyclopenta[b]thienyl |
| | butylmethylcyclopenta[b]furanyl |
| | butylmethylcyclopenta[b]pyrrolyl |
| | butylmethylcyclopenta[b]phospholyl |
| | cyclopenta[c]thienyl |
| | cyclopenta[c]furanyl |

TABLE A-continued

| M | Cp, Cp* |
|---|---|
| | cyclopenta[c]selenophenyl |
| | cyclopenta[c]tellurophenyl |
| | cyclopenta[c]pyrrolyl |
| | cyclopenta[c]phospholyl |
| | cyclopenta[c]arsolyl |
| | cyclopenta[c]stibolyl |
| | methylcyclopenta[c]thienyl |
| | methylcyclopenta[c]furanyl |
| | methylcyclopenta[c]selenophenyl |
| | methylcyclopenta[c]tellurophenyl |
| | methylcyclopenta[c]pyrrolyl |
| | methylcyclopenta[c]phospholyl |
| | methylcyclopenta[c]arsolyl |
| | methylcyclopenta[c]stibolyl |
| | dimethylcyclopenta[c]thienyl |
| | dimethylcyclopenta[c]furanyl |
| | dimethylcyclopenta[c]pyrrolyl |
| | dimethylcyclopenta[c]phospholyl |
| | trimethylcyclopenta[c]thienyl |
| | trimethylcyclopenta[c]furanyl |
| | trimethylcyclopenta[c]pyrrolyl |
| | trimethylcyclopenta[c]phospholyl |
| | ethylcyclopenta[c]thienyl |
| | ethylcyclopenta[c]furanyl |
| | ethylcyclopenta[c]pyrrolyl |
| | ethylcyclopenta[c]phospholyl |
| | diethylcyclopenta[c]thienyl |
| | diethylcyclopenta[c]furanyl |
| | diethylcyclopenta[c]pyrrolyl |
| | diethylcyclopenta[c]phospholyl |
| | triethylcyclopenta[c]thienyl |
| | triethylcyclopenta[c]furanyl |
| | triethylcyclopenta[c]pyrrolyl |
| | triethylcyclopenta[c]phospholyl |
| | propylcyclopenta[c]thienyl |
| | propylcyclopenta[c]furanyl |
| | propylcyclopenta[c]pyrrolyl |
| | propylcyclopenta[c]phospholyl |
| | dipropylcyclopenta[c]thienyl |
| | dipropylcyclopenta[c]furanyl |
| | dipropylcyclopenta[c]pyrrolyl |
| | dipropylcyclopenta[c]phospholyl |
| | tripropylcyclopenta[c]thienyl |
| | tripropylcyclopenta[c]furanyl |
| | tripropylcyclopenta[c]pyrrolyl |
| | tripropylcyclopenta[c]phospholyl |
| | butylcyclopenta[c]thienyl |
| | butylcyclopenta[c]furanyl |
| | butylcyclopenta[c]pyrrolyl |
| | butylcyclopenta[c]phospholyl |
| | dibutylcyclopenta[c]thienyl |
| | dibutylcyclopenta[c]furanyl |
| | dibutylcyclopenta[c]pyrrolyl |
| | dibutylcyclopenta[c]phospholyl |
| | tributylcyclopenta[c]thienyl |
| | tributylcyclopenta[c]furanyl |
| | tributylcyclopenta[c]pyrrolyl |
| | tributylcyclopenta[c]phospholyl |
| | ethylmethylcyclopenta[c]thienyl |
| | ethylmethylcyclopenta[c]furanyl |
| | ethylmethylcyclopenta[c]pyrrolyl |
| | ethylmethylcyclopenta[c]phospholyl |
| | methylpropylcyclopenta[c]thienyl |
| | methylpropylcyclopenta[c]furanyl |
| | methylpropylcyclopenta[c]pyrrolyl |
| | methylpropylcyclopenta[c]phospholyl |
| | butylmethylcyclopenta[c]thienyl |
| | butylmethylcyclopenta[c]furanyl |
| | butylmethylcyclopenta[c]pyrrolyl |
| | butylmethylcyclopenta[c]phospholyl |
| | pentamethylcyclopentadienyl |
| | tetrahydroindenyl |
| | mehtyltetrahydroindenyl |
| | dimethyltetrahydroindenyl |

In a preferred embodiment of the invention, when used with an NCA, Cp is the same as Cp* and is a substituted or unsubstituted indenyl or tetrahydroindenyl ligand. Most preferred substituted and unsubstituted indenyl or tetrahydroindenyl ligands include having a substituent in the 2-position of the indenyl or tetrahydroindenyl ring, indenyl, tetrahydroindenyl, 4,7-dimethylindenyl and 5,6-dimethylindenyl.

Preferred metallocene compounds (pre-catalysts) which, according to the present invention, provide catalyst systems which are specific to the production of low viscosity poly-α-olefins include:

Bis(1,2-dimethylcyclopentadienyl)zirconium dichloride
Bis(1,3-dimethylcyclopentadienyl)zirconium dichloride
Bis(1,2,3-trimethylcyclopentadienyl)zirconium dichloride
Bis(1,2,4-trimethylcyclopentadienyl)zirconium dichloride
Bis(1,2,3,4-tetramethylcyclopentadienyl)zirconium dichloride
Bis(1,2,3,4,5-pentamethylcyclopentadienyl)zirconium dichloride
Bis(1-methyl-2-ethylcyclopentadienyl)zirconium dichloride
Bis(1-methyl-2-n-propylcyclopentadienyl)zirconium dichloride
Bis(1-methyl-2-n-butyllcyclopentadienyl)zirconium dichloride
Bis(1-methyl-3-ethylcyclopentadienyl)zirconium dichloride
Bis(1-methyl-3-n-propylcyclopentadienyl)zirconium dichloride
Bis(1-methyl-3-n-butylcyclopentadienyl)zirconium dichloride
Bis(1-methyl-3-n-pentylcyclopentadienyl)zirconium dichloride
Bis(1,2-dimethyl-4-ethylcyclopentadienyl)zirconium dichloride
Bis(1,2-dimethyl-4-n-propylcyclopentadienyl)zirconium dichloride
Bis(1,2-dimethyl-4-n-butylcyclopentadienyl)zirconium dichloride
Bis(1,2-diethylcyclopentadienyl)zirconium dichloride
Bis(1,3-diethylcyclopentadienyl)zirconium dichloride
Bis(1,2-di-n-propylcyclopentadienyl)zirconium dichloride
Bis(1,2-di-n-butylcyclopentadienyl)zirconium dichloride
Bis(1-methyl-2,4-diethylcyclopentadienyl)zirconium dichloride
Bis(1,2-diethyl-4-n-propylcyclopentadienyl)zirconium dichloride
Bis(1,2-diethyl-4-n-butylcyclopentadienyl)zirconium dichloride
Bis(1-methyl-3-i-propylcyclopentadienyl)zirconium dichloride
Bis(1-ethyl-3-i-propylcyclopentadienyl)zirconium dichloride
(1,2-dimethylcyclopentadienyl)(cyclopentadienyl)zirconium dichloride
(1,3-dimethylcyclopentadienyl)(cyclopentadienyl)zirconium dichloride
(1,2-dimethylcyclopentadienyl)(methylcyclopentadienyl)zirconium dichloride
(1,2-dimethylcyclopentadienyl)(ethylcyclopentadienyl)zirconium dichloride
(1,2-dimethylcyclopentadienyl)(1,2-di-n-butylcyclopentadienyl)zirconium dichloride
(1,3-dimethylcyclopentadienyl)(cyclopentadienyl)zirconium dichloride
(1,3-dimethylcyclopentadienyl)(1,2-dimethylcyclopentadienyl)zirconium dichloride
(1,3-dimethylcyclopentadienyl)(1,3-diethylcyclopentadienyl)zirconium dichloride
Bis(indenyl)zirconium dichloride
Bis(1-methylindenyl)zirconium dichloride
Bis(2-methylindenyl)zirconium dichloride Bis(4-methylindenyl)zirconium dichloride
Bis(4,7-dimethylindenyl)zirconium dichloride
Bis(4,5,6,7-tetrahydroindenyl)zirconium dichloride
Bis(4,5,6,7-tetrahydro-2-methylindenyl)zirconium dichloride
Bis(4,5,6,7-tetrahydro-4,7-dimethylindenyl)zirconium dichloride (Cyclopentadienyl)(4,5,6,7-tetrahydroindenyl) zirconium dichloride The preferred catalysts also include the zirconium dihalides, di-methyl, di-isobutyl, di-n-octyl or other di-alkyl analogs of the above compounds, and the hafnium dichloride, dihalides, or the hafnium di-methyl or di-alkyl analogs of the above compounds.

Particularly preferred catalyst compounds also include bis (1,2-dimethylcyclopentadienyl)zirconium dichloride, bis(1,3-dimethylcyclopentadienyl)zirconium dichloride, bis(1,2,4-trimethylcyclopentadienyl)zirconium dichloride and bis (tetramethylcyclopentadienyl)zirconium dichloride, bis(1-methyl-2-ethylcyclopentadienyl)zirconium dichloride, bis (1-methyl-3-ethylcyclopentadienyl)zirconium dichloride, bis(1-methyl-3-n-propylcyclopentadienyl)zirconium dichloride, bis(1-methyl-3-n-butylclopentadienyl)zirconium dichloride, bis(4,5,6,7-tetrahydro indenyl)zirconium dichloride, bis(indenyl)zirconium dichloride, bis(1,2-dimethylcyclopentadienyl)zirconium dimethyl, bis(1,3-dimethylcyclopentadienyl)zirconium dimethyl, bis(1,2,4-trimethylcyclopentadienyl)zirconium dimethyl and bis (tetramethylcyclopentadienyl)zirconium dimethyl, bis(1-methyl-2-ethylcyclopentadienyl)zirconium dimethyl, bis(1-methyl-3-ethylcyclopentadienyl)zirconium dimethyl, bis(1-methyl-3-n-propylcyclopentadienyl)zirconium dimethyl, bis (1-methyl-3-n-butylclopentadienyl)zirconium dimethyl, bis (4,5,6,7-tetrahydro indenyl)zirconium dichloride, bis (indenyl)zirconium dimethyl.

Activators and Catalyst Activation

The catalyst precursors, when activated by a commonly known activator such as non-coordinating anion activator, form active catalysts for the polymerization or oligomerization of olefins. Activators that may be used include Lewis acid activators such as triphenylboron, tris-perfluorophenylboron, tris-perfluorophenylaluminum and the like and or ionic activators such as dimethylanilinium tetrakisperfluorophenylborate, triphenylcarboniumtetrakis perfluorophenylborate, dimethylaniliniumtetrakisperfluorophenylaluminate, and the like.

A co-activator is a compound capable of alkylating the transition metal complex, such that when used in combination with an activator, an active catalyst is formed. Co-activators include alumoxanes such as methylalumoxane, modified alumoxanes such as modified methylalumoxane, and aluminum alkyls such trimethylaluminum, tri-isobutylaluminum, triethylaluminum, and tri-isopropylaluminum, tri-n-hexylaluminum, tri-n-octylaluminum, tri-n-decylaluminum or tri-n-dodecylaluminum. Co-activators are typically used in combination with Lewis acid activators and ionic activators when the pre-catalyst is not a dihydrocarbyl or dihydride complex. Sometimes co-activators are also used as scavengers to deactivate impurities in feed or reactors.

Particularly preferred co-activators include alkylaluminum compounds represented by the formula: $R_3Al$, where each R is, independently, a C1 to C18 alkyl group, preferably each R is, independently, selected from the group consisting of methyl, ethyle, n-propyl, iso-propyl, iso-butyl, n-butyl, t-butyl, n-pentyl, iso-pentyl, neopentyl, n-hexyl, iso-hexyl, n-heptyl, iso-heptyl, n-octyl, iso-octyl, n-nonyl, n-decyl, n-undecyl, n-dodecyl, n-tridecyl, n-tetradecyl, n-pentadecyl, n-hexadecyl, n-heptadecyl, n-octadecyl, and their iso-analogs.

Ionic activators (at times used in combination with a co-activator) may be used in the practice of this invention. Preferably, discrete ionic activators such as $[Me_2PhNH][B(C_6F_5)_4]$, $[Ph_3C][B(C_6F_5)_4]$, $[Me_2PhNH][B((C_6H_3-3,5-(CF_3)_2))_4]$, $[Ph_3C][B((C_6H_3-3,5-(CF_3)_2))_4]$, $[NH_4][B(C_6H_5)_4]$ or Lewis acidic activators such as $B(C_6F_5)_3$ or $B(C_6H_5)_3$ can be used, where Ph is phenyl and Me is methyl. Preferred co-activators, when used, are alumoxanes such as methylalumoxane, modified alumoxanes such as modified methylalumoxane, and aluminum alkyls such as tri-isobutylaluminum, and trimethylaluminum, triethylaluminum, and tri-isopropylaluminum, tri-n-hexylaluminum, tri-n-octylaluminum, tri-n-decylaluminum or tri-n-dodecylaluminum.

It is within the scope of this invention to use an ionizing or stoichiometric activator, neutral or ionic, such as tri(n-butyl) ammoniumtetrakis(pentafluorophenyl) borate, a trisperfluorophenyl boron metalloid precursor or a trisperfluoronaphthyl boron metalloid precursor, polyhalogenated heteroborane anions (WO 98/43983), boric acid (U.S. Pat. No. 5,942,459) or combination thereof.

Examples of neutral stoichiometric activators include tri-substituted boron, tellurium, aluminum, gallium and indium or mixtures thereof. The three substituent groups are each independently selected from alkyls, alkenyls, halogen, substituted alkyls, aryls, arylhalides, alkoxy and halides. Preferably, the three groups are independently selected from halogen, mono or multicyclic (including halosubstituted) aryls, alkyls, and alkenyl compounds and mixtures thereof, preferred are alkenyl groups having 1 to 20 carbon atoms, alkyl groups having 1 to 20 carbon atoms, alkoxy groups having 1 to 20 carbon atoms and aryl groups having 3 to 20 carbon atoms (including substituted aryls). More preferably, the three groups are alkyls having 1 to 4 carbon groups, phenyl, naphthyl or mixtures thereof. Even more preferably, the three groups are halogenated, preferably fluorinated, aryl groups. Most preferably, the neutral stoichiometric activator is trisperfluorophenyl boron or trisperfluoronaphthyl boron.

Ionic stoichiometric activator compounds may contain an active proton, or some other cation associated with, but not coordinated to, or only loosely coordinated to, the remaining ion of the ionizing compound. Such compounds and the like are described in European publications EP-A-0 570 982, EP-A-0 520 732, EP-A-0 495 375, EP-B1-0 500 944, EP-A-0 277 003 and EP-A-0 277 004, and U.S. Pat. Nos. 5,153,157, 5,198,401, 5,066,741, 5,206,197, 5,241,025, 5,384,299 and 5,502,124 and U.S. patent application Ser. No. 08/285,380, filed Aug. 3, 1994, all of which are herein fully incorporated by reference.

Ionic catalysts can be prepared by reacting a transition metal compound with an activator, such as $B(C_6F_6)_3$, which upon reaction with the hydrolyzable ligand (X') of the transition metal compound forms an anion, such as $([B(C_6F_5)_3(X')]^-)$, which stabilizes the cationic transition metal species generated by the reaction. The catalysts can be, and preferably are, prepared with activator components which are ionic compounds or compositions. However preparation of activators utilizing neutral compounds is also contemplated by this invention.

Compounds useful as an activator component in the preparation of the ionic catalyst systems used in the process of this invention comprise a cation, which is preferably a Bronsted acid capable of donating a proton, and a compatible non-coordinating anion which anion is relatively large (bulky), capable of stabilizing the active catalyst species which is formed when the two compounds are combined and said anion will be sufficiently labile to be displaced by olefinic diolefinic and acetylenically unsaturated substrates or other neutral Lewis bases such as ethers, nitriles and the like. Two classes of compatible non-coordinating anions have been disclosed in EPA 277,003 and EPA 277,004 published 1988: 1) anionic coordination complexes comprising a plurality of lipophilic radicals covalently coordinated to and shielding a central charge-bearing metal or metalloid core, and 2) anions comprising a plurality of boron atoms such as carboranes, metallacarboranes and boranes. In a preferred embodiment, the stoichiometric activators include a cation and an anion component, and may be represented by the following formula: $(L^{}\text{-}H)_d^+ (A^{d-})$ wherein $L^{}$ is an neutral Lewis base; H is hydrogen; $(L^{**}\text{-}H)^+$ is a Bronsted acid $A^{d-}$ is a non-coordinating anion having the charge d-d is an integer from 1 to 3.

The cation component, $(L^{**}\text{-}H)_d^+$ may include Bronsted acids such as protons or protonated Lewis bases or reducible Lewis acids capable of protonating or abstracting a moiety, such as an alkyl or aryl, from the precatalyst after alkylation.

The activating cation $(L^{}\text{-}H)_d^+$ may be a Bronsted acid, capable of donating a proton to the alkylated transition metal catalytic precursor resulting in a transition metal cation, including ammoniums, oxoniums, phosphoniums, silyliums, and mixtures thereof, preferably ammoniums of methylamine, aniline, dimethylamine, diethylamine, N-methylaniline, diphenylamine, trimethylamine, triethylamine, N,N-dimethylaniline, methyldiphenylamine, pyridine, p-bromo N,N-dimethylaniline, p-nitro-N,N-dimethylaniline, phosphoniums from triethylphosphine, triphenylphosphine, and diphenylphosphine, oxomiuns from ethers such as dimethyl ether, diethyl ether, tetrahydrofuran and dioxane, sulfoniums from thioethers, such as diethyl thioethers and tetrahydrothiophene, and mixtures thereof. The activating cation $(L^{}\text{-}H)_d^+$ may also be a moiety such as silver, tropylium, carbeniums, ferroceniums and mixtures, preferably carboniums and ferroceniums; most preferably triphenyl carbonium. The anion component $A^{d-}$ include those having the formula $[M^{k+}Q_n]^{d-}$ wherein k is an integer from 1 to 3; n is an integer from 2-6; n–k=d; M is an element selected from Group 13 of the Periodic Table of the Elements, preferably boron or aluminum, and Q is independently a hydride, bridged or unbridged dialkylamido, halide, alkoxide, aryloxide, hydrocarbyl, substituted hydrocarbyl, halocarbyl, substituted halocarbyl, and halosubstituted-hydrocarbyl radicals, said Q having up to 20 carbon atoms with the proviso that in not more than one occurrence is Q a halide. Preferably, each Q is a fluorinated hydrocarbyl group having 1 to 20 carbon atoms, more preferably each Q is a fluorinated aryl group, and most preferably each Q is a pentafluoryl aryl group. Examples of suitable $A^{d-}$ also include diboron compounds as disclosed in U.S. Pat. No. 5,447,895, which is fully incorporated herein by reference.

Illustrative, but not limiting examples of boron compounds which may be used as an activating cocatalyst in combination with a co-activator in the preparation of the improved catalysts of this invention are tri-substituted ammonium salts such as: trimethylammonium tetraphenylborate, triethylammonium tetraphenylborate, tripropylammonium tetraphenylborate, tri(n-butyl)ammonium tetraphenylborate, tri(tert-butyl)ammonium tetraphenylborate, N,N-dimethylanilinium tetraphenylborate, N,N-diethylanilinium tetraphenylborate, N,N-dimethyl-(2,4,6-trimethylanilinium) tetraphenylborate, trimethylammonium tetrakis(pentafluorophenyl)borate, triethylammonium tetrakis(pentafluorophenyl)borate, tripropylammonium tetrakis(pentafluorophenyl)borate, tri(n-butyl)ammonium tetrakis(pentafluorophenyl)borate, tri(sec-butyl)ammonium tetrakis(pentafluorophenyl)borate, N,N-dimethylanilinium tetrakis(pentafluorophenyl)borate, N,N-diethylanilinium tetrakis(pentafluorophenyl)borate, N,N-dimethyl-(2,4,6-trimethylanilinium) tetrakis(pentafluorophenyl)borate, trimethylammonium tetrakis-(2,3,4,6-tetrafluorophenyl)borate, triethylammonium tetrakis-(2,3,4,6-tetrafluorophenyl)borate, tripropylammonium tetrakis-(2,3,4,6-tetrafluorophenyl)borate, tri(n-butyl)ammonium tetrakis-(2,3,4,6-tetrafluorophenyl)borate, dimethyl (tert-butyl)ammonium tetrakis-(2,3,4,6-tetrafluorophenyl)borate, N,N-dimethylanilinium tetrakis-(2,3,4,6-tetrafluorophenyl)borate, N,N-diethylanilinium tetrakis-(2,3,4,6-tetrafluorophenyl)borate, N,N-dimethyl-(2,4,6-trimethylanilinium)tetrakis-(2,3,4,6-tetrafluorophenyl) borate, trimethylammonium tetrakis(perfluoronaphthyl)borate, triethylammonium tetrakis(perfluoronaphthyl)borate, tripropylammonium tetrakis(perfluoronaphthyl)borate, tri(n-butyl)ammonium tetrakis(perfluoronaphthyl)borate, tri(tert-butyl)ammonium tetrakis(perfluoronaphthyl)borate, N,N-dimethylanilinium tetrakis(perfluoronaphthyl)borate, N,N-diethylanilinium tetrakis(perfluoronaphthyl)borate, N,N-dimethyl-(2,4,6-trimethylanilinium) tetrakis(perfluoronaphthyl)borate, trimethylammonium tetrakis(perfluorobiphenyl)borate, triethylammonium tetrakis(perfluorobiphenyl)borate, tripropylammonium tetrakis(perfluorobiphenyl)borate, tri(n-butyl)ammonium tetrakis(perfluorobiphenyl)borate, tri(tert-butyl)ammonium tetrakis(perfluorobiphenyl)borate, N,N-dimethylanilinium tetrakis(perfluorobiphenyl)borate, N,N-diethylanilinium tetrakis(perfluorobiphenyl)borate, N,N-dimethyl-(2,4,6-trimethylanilinium) tetrakis(perfluorobiphenyl)borate, trimethylammonium tetrakis(3,5-bis(trifluoromethyl)phenyl)borate, triethylammonium tetrakis(3,5-bis(trifluoromethyl)phenyl)borate, tripropylammonium tetrakis(3,5-bis(trifluoromethyl)phenyl)borate, tri(n-butyl)ammonium tetrakis(3,5-bis(trifluoromethyl)phenyl)borate, tri(tert-butyl)ammonium tetrakis(3,5-bis(trifluoromethyl)phenyl)borate, N,N-dimethylanilinium tetrakis(3,5-bis(trifluoromethyl)phenyl)borate, N,N-diethylanilinium tetrakis(3,5-bis(trifluoromethyl)phenyl)borate, N,N-dimethyl-(2,4,6-trimethylanilinium) tetrakis(3,5-bis(trifluoromethyl)phenyl)borate, and dialkyl ammonium salts such as: di-(iso-propyl)ammonium tetrakis(pentafluorophenyl)borate, and dicyclohexylammonium tetrakis(pentafluorophenyl)borate; and other salts such as tri(o-tolyl)phosphonium tetrakis(pentafluorophenyl)borate, tri(2,6-dimethylphenyl)phosphonium tetrakis(pentafluorophenyl)borate, tropillium tetraphenylborate, triphenylcarbenium tetraphenylborate, triphenylphosphonium tetraphenylborate, triethylsilylium tetraphenylborate, benzene(diazonium)tetraphenylborate, tropillium tetrakis(pentafluorophenyl)borate, triphenylcarbenium tetrakis(pentafluorophenyl)borate, triphenylphosphonium tetrakis (pentafluorophenyl)borate, triethylsilylium tetrakis (pentafluorophenyl)borate, benzene(diazonium) tetrakis (pentafluorophenyl)borate, tropillium tetrakis-(2,3,4,6-tetrafluorophenyl)borate, triphenylcarbenium tetrakis-(2,3,4,6-tetrafluorophenyl)borate, triphenylphosphonium tetrakis-(2,3,4,6-tetrafluorophenyl)borate, triethylsilylium tetrakis-(2,3,4,6-tetrafluorophenyl)borate, benzene(diazonium) tetrakis-(2,3,4,6-tetrafluorophenyl)borate, tropillium tetrakis (perfluoronaphthyl)borate, triphenylcarbenium tetrakis (perfluoronaphthyl)borate, triphenylphosphonium tetrakis (perfluoronaphthyl)borate, triethylsilylium tetrakis (perfluoronaphthyl)borate, benzene(diazonium) tetrakis (perfluoronaphthyl)borate, tropillium tetrakis (perfluorobiphenyl)borate, triphenylcarbenium tetrakis (perfluorobiphenyl)borate, triphenylphosphonium tetrakis (perfluorobiphenyl)borate, triethylsilylium tetrakis (perfluorobiphenyl)borate, benzene(diazonium) tetrakis (perfluorobiphenyl)borate, tropillium tetrakis(3,5-bis (trifluoromethyl)phenyl)borate, triphenylcarbenium tetrakis (3,5-bis(trifluoromethyl)phenyl)borate, triphenylphosphonium tetrakis(3,5-bis(trifluoromethyl)phenyl)borate, triethylsilylium tetrakis(3,5-bis(trifluoromethyl) phenyl)borate, and benzene(diazonium)tetrakis(3,5-bis(trifluoromethyl)phenyl)borate.

Most preferably, the ionic stoichiometric activator ($L^{**}$-$H)_d^+$ ($A^{d-}$) is N,N-dimethylanilinium tetrakis(perfluorophenyl)borate, N,N-dimethylanilinium tetrakis(perfluoronaphthyl)borate, N,N-dimethylanilinium tetrakis (perfluorobiphenyl)borate, N,N-dimethylanilinium tetrakis (3,5-bis(trifluoromethyl)phenyl)borate, triphenylcarbenium tetrakis(perfluoronaphthyl)borate, triphenylcarbenium tetrakis(perfluorobiphenyl)borate, triphenylcarbenium tetrakis (3,5-bis(trifluoromethyl)phenyl)borate, or triphenylcarbenium tetra(perfluorophenyl)borate.

The catalyst precursors can also be activated with cocatalysts or activators that comprise non-coordinating anions containing metalloid-free cyclopentadienide ions. These are described in U.S. Patent Publication 2002/0058765 A1, published on 16 May 2002, and for the instant invention, require the addition of a co-activator to the catalyst pre-cursor. "Compatible" non-coordinating anions are those which are not degraded to neutrality when the initially formed complex decomposes. Further, the anion will not transfer an anionic substituent or fragment to the cation so as to cause it to form a neutral transition metal compound and a neutral by-product from the anion. Preferred non-coordinating anions useful in accordance with this invention are those that are compatible, stabilize the transition metal complex cation in the sense of balancing its ionic charge at +1, yet retain sufficient lability to permit displacement by an ethylenically or acetylenically unsaturated monomer during polymerization. These types of cocatalysts are sometimes used with scavengers such as but not limited to tri-iso-butylaluminum, tri-n-octylaluminum, tri-n-hexylaluminum, triethylaluminum or trimethylaluminum.

Invention processes also can employ cocatalyst compounds or activator compounds that are initially neutral Lewis acids but form a cationic metal complex and a noncoordinating anion, or a zwitterionic complex upon reaction with the alkylated transition metal compounds. The alkylated metallocene compound is formed from the reaction of the catalyst pre-cursor and the co-activator. For example, tris (pentafluorophenyl) boron or aluminum act to abstract a hydrocarbyl ligand to yield an invention cationic transition metal complex and stabilizing noncoordinating anion, see EP-A-0 427 697 and EP-A-0 520 732 for illustrations of analogous Group-4 metallocene compounds. Also, see the methods and compounds of EP-A-0 495 375. For formation of zwitterionic complexes using analogous Group 4 compounds, see U.S. Pat. Nos. 5,624,878; 5,486,632; and 5,527,929.

Additional neutral Lewis-acids are known in the art and are suitable for abstracting formal anionic ligands. See in particular the review article by E. Y.-X. Chen and T. J. Marks, "Cocatalysts for Metal-Catalyzed Olefin Polymerization: Activators, Activation Processes, and Structure-Activity Relationships", *Chem. Rev.*, 100, 1391-1434 (2000).

When the cations of noncoordinating anion precursors are Bronsted acids such as protons or protonated Lewis bases (excluding water), or reducible Lewis acids such as ferrocenium or silver cations, or alkali or alkaline earth metal cations such as those of sodium, magnesium or lithium, the catalyst-precursor-to-activator molar ratio may be any ratio. Combinations of the described activator compounds may also be used for activation.

When an ionic or neutral stoichiometric activator (such as an NCA) is used, the catalyst-precursor-to-activator molar ratio is from 1:10 to 1:1; 1:10 to 10:1; 1:10 to 2:1; 1:10 to 3:1; 1:10 to 5:1; 1:2 to 1.2:1; 1:2 to 10:1; 1:2 to 2:1; 1:2 to 3:1; 1:2 to 5:1; 1:3 to 1.2:1; 1:3 to 10:1; 1:3 to 2:1; 1:3 to 3:1; 1:3 to 5:1; 1:5 to 1:1; 1:5 to 10:1; 1:5 to 2:1; 1:5 to 3:1; 1:5 to 5:1; 1:1 to 1:1.2. The catalyst-precursor-to-co-activator molar ratio is from 1:500 to 1:1, 1:100 to 100:1; 1:75 to 75:1; 1:50 to 50:1; 1:25 to 25:1; 1:15 to 15:1; 1:10 to 10:1; 1:5 to 5:1, 1:2 to 2:1; 1:100 to 1:1; 1:75 to 1:1; 1:50 to 1:1; 1:25 to 1:1; 1:15 to 1:1; 1:10 to 1:1; 1:5 to 1:1; 1:2 to 1:1; 1:10 to 2:1. Preferred activators and activator/co-activator combinations include methylalumoxane, modified methylalumoxane, mixtures of methylalumoxane with dimethylanilinium tetrakis(pentafluorophenyl)borate or tris(pentafluorophenyl)boron, and mixtures of trimethyl aluminum with dimethylanilinium tetrakis(pentafluorophenyl)borate or tris(pentafluorophenyl) boron In some embodiments, scavenging compounds are used with stoichiometric activators. Typical aluminum or boron alkyl components useful as scavengers are represented by the general formula $R^xJZ_2$ where J is aluminum or boron, $R^x$ is as previously defined above, and each Z is independently $R^x$ or a different univalent anionic ligand such as halogen (Cl, Br, I), alkoxide ($OR^x$) and the like. Most preferred aluminum alkyls include triethylaluminum, diethylaluminum chloride, tri-iso-butylaluminum, tri-n-octylaluminum. tri-n-hexylaluminum, trimethylaluminum and the like. Preferred boron alkyls include triethylboron. Scavenging compounds may also be alumoxanes and modified alumoxanes including methylalumoxane and modified methylalumoxane.

In an alternate embodiment, alkylalumoxane compounds (such as methyl alumoxane, and modified methylalumoxane) are present in the reaction zone at less than 3 mg of alumoxane/gram of olefin feed, preferably less than 1 mg of alumoxane/gram of olefin feed, preferably less than 0.5 mg of alumoxane/g of olefin feed.

Supported Catalysts

Supported catalysts and or supported catalyst systems may be used to prepare PAO's. To prepare uniform supported catalysts, the catalyst precursor preferably dissolves in the chosen solvent. The term "uniform supported catalyst" means that the catalyst precursor, the activator, and or the activated catalyst approach uniform distribution upon the support's accessible surface area, including the interior pore surfaces of porous supports. Some embodiments of supported catalysts prefer uniform supported catalysts; other embodiments show no such preference.

Useful supported catalyst systems may be prepared by any method effective to support other coordination catalyst systems, effective meaning that the catalyst so prepared can be used for oligomerizing or polymerizing olefins in a heterogeneous process. The catalyst precursor, activator, co-activator (if needed), suitable solvent, and support may be added in any order or simultaneously.

By one method, the activator, dissolved in an appropriate solvent such as toluene, may be stirred with the support material for 1 minute to 10 hours to prepare the supported catalyst. The total solution volume (of the catalyst solution, the activator solution or both) may be greater than the pore volume of the support, but some embodiments limit the total solution volume below that needed to form a gel or slurry (about 90% to 400%, preferably about 100-200%, of the pore volume). The mixture is optionally heated from 30-200° C. during this time. The catalyst precursor may be added to this mixture as a solid, if a suitable solvent is employed in the previous step, or as a solution. Alternatively, the mixture can be filtered, and the resulting solid mixed with a catalyst precursor solution. Similarly, the mixture may be vacuum dried and mixed with a catalyst precursor solution. The resulting catalyst mixture is then stirred for 1 minute to 10 hours, and the supported catalyst is either filtered from the solution and vacuum dried or subjected to evaporation to remove the solvent.

Alternatively, the catalyst precursor and activator may be combined in solvent to form a solution. The support is then added to the solution, and the resulting mixture is stirred for 1 minute to 10 hours. The total activator/catalyst-precursor solution volume may be greater than the pore volume of the support, but some embodiments limit the total solution volume below that needed to form a gel or slurry (about 90% to 400%, preferably about 100-200% of the pore volume). After stirring, the residual solvent is removed under vacuum, typically at ambient temperature and over 10-16 hours; however, greater or lesser times and temperatures may be used.

The catalyst precursor may also be supported absent the activator; in this case, the activator (and co-activator if needed) is added to the liquid phase of a slurry process. For example, a solution of catalyst precursor may be mixed with a support material for a period of about 1 minute to 10 hours. The resulting precatalyst mixture may be filtered from the solution and dried under vacuum or treated with evaporation to remove the solvent. The total catalyst-precursor-solution volume may be greater than the support's pore volume, but some embodiments limit the total solution volume below that needed to form a gel or slurry (about 90% to 400%, preferably about 100-200% of the pore volume).

Additionally, two or more different catalyst precursors may be placed on the same support using any of the support methods disclosed above. Likewise, two or more activators or an activator and a co-activator, may be placed on the same support. Suitable solid particle supports are typically comprised of polymeric or refractory oxide materials, each being preferably porous. Any support material that has an average particle size greater than 10 µm is suitable for use in this invention. Various embodiments select a porous support material, such as for example, talc, inorganic oxides, inorganic chlorides, for example magnesium chloride and resinous support materials such as polystyrene polyolefin or polymeric compounds or any other organic support material and the like. Some embodiments select inorganic oxide materials as the support material including Group-2, -3, -4, -5, -13, or -14 metal or metalloid oxides. Some embodiments select the catalyst support materials to include silica, alumina, silica-alumina, and their mixtures. Other inorganic oxides may serve either alone or in combination with the silica, alumina, or silica-alumina. These are magnesia, titania, zirconia, and the like. Lewis acidic materials such as montmorillonite and similar clays may also serve as a support. In this case, the support can optionally double as an activator component. But additional activator may also be used. In some cases, a special family of solid support commonly known as MCM-41 can also be used. MCM-41 is a new class of unique crystalline support and can be prepared with tunable pore size and tunable acidity when modified with a second component. A detailed description of this class of materials and their modification can be found in U.S. Pat. No. 5,264,203.

The support material may be pretreated by any number of methods. For example, inorganic oxides may be calcined, chemically treated with dehydroxylating agents such as aluminum alkyls and the like, or both.

As stated above, polymeric carriers will also be suitable in accordance with the invention, see for example the descriptions in WO 95/15815 and U.S. Pat. No. 5,427,991. The methods disclosed may be used with the catalyst compounds, activators or catalyst systems of this invention to adsorb or absorb them on the polymeric supports, particularly if made up of porous particles, or may be chemically bound through functional groups bound to or in the polymer chains.

Useful catalyst carriers may have a surface area of from 10-700 $m^2/g$, and or a pore volume of 0.1-4.0 cc/g and or an average particle size of 10-500 µm. Some embodiments select a surface area of 50-500 $m^2/g$, and or a pore volume of 0.5-3.5 cc/g, and or an average particle size of 20-200 µm. Other embodiments select a surface area of 100-400 $m^2/g$, and or a pore volume of 0.8-3.0 cc/g, and or an average particle size of 30-100 µm. Invention carriers typically have a pore size of 10-1000 Angstroms, alternatively 50-500 Angstroms, or 75-350 Angstroms. The metallocenes and or the metallocene/activator combinations are generally deposited on the support at a loading level of 10-100 micromoles of catalyst precursor per gram of solid support; alternately 20-80 micromoles of catalyst precursor per gram of solid support; or 40-60 micromoles of catalyst precursor per gram of support. But greater or lesser values may be used provided that the total amount of solid catalyst precursor does not exceed the support's pore volume.

The metallocenes and or the metallocene/activator combinations can be supported for gas-phase, bulk, or slurry polymerization, or otherwise as needed. Numerous support methods are known for catalysts in the olefin polymerization art, particularly alumoxane-activated catalysts; all are suitable for use herein. See, for example, U.S. Pat. Nos. 5,057,475 and 5,227,440. An example of supported ionic catalysts appears in WO 94/03056. U.S. Pat. No. 5,643,847 and WO 96/04319A which describe a particularly effective method. Both polymers and inorganic oxides may serve as supports, see U.S. Pat. Nos. 5,422,325, 5,427,991, 5,498,582 and 5,466,649, and international publications WO 93/11172 and WO 94/07928.

In another preferred embodiment, the metallocene and or activator (with or without a support) are combined with an alkylaluminum compound, preferably a trialkylaluminum compound, prior to entering the reactor. Preferably the alkylaluminum compound is represented by the formula: $R_3Al$, where each R is independently a C1 to C20 alkyl group; preferably the R groups are independently selected from the group consisting of methyl, ethyl, propyl, isopropyl, butyl, isobutyl, n-butyl, pentyl, isopentyl, n-pentyl, hexyl, isohexyl, n-hexyl, heptyl, octyl, isooctyl, n-octyl, nonyl, isononyl, n-nonyl, decyl, isodecyl, n-decyl, undecyl, isoundecyl, n-undecyl, dodecyl, isododecyl, and n-dodecyl, preferably isobutyl, n-octyl, n-hexyl, and n-dodecyl. Preferably the alkylaluminum compound is selected from tri-isobutyl aluminum, tri n-octyl aluminum, tri-n-hexyl aluminum, and tri-n-dodecyl aluminum.

Monomers

In a preferred embodiment the catalyst compounds described herein are used to polymerize or oligomerize any unsaturated monomer or monomers. Preferred monomers include $C_3$ to $C_{24}$ olefins, preferably $C_4$ to $C_{20}$ olefins, more preferably $C_5$ to $C_{20}$ olefins, more preferably $C_6$ to $C_{14}$ olefins, more preferably $C_8$ to $C_{12}$ olefins. In some embodiments preferred monomers include linear, branched or cyclic alpha-olefins, preferably $C_3$ to $C_{20}$ alpha-olefins, preferably $C_6$ to $C_{14}$ alpha-olefins, and more preferably $C_8$ to $C_{12}$ alpha-olefins. Preferred olefin monomers may be one or more of hexene, heptene, octene, nonene, decene, dodecene, 3-methyl-1-butene, and tetradecene.

In a preferred embodiment, the process described herein may be used to produce homo-oligomers or co-oligomers (for the purposes of this invention and the claims thereto, a co-oligomer may comprise two, three, four, or more different monomer units). Preferred oligomers produced herein include homo-oligomers or co-oligomers of any of the above monomers. In a preferred embodiment the oligomer is a homo-oligomer of any $C_8$ to $C_{12}$ alpha-olefin. Preferably the oligomer is a homo-oligomer of 1-hexene, 1-heptene, 1-octene, 1-nonene, 1-decene, 1-undecene, or 1-dodecene. Preferably the oligomer is a homo-oligomer of decene. In another embodiment the oligomer is a co-oligomer comprising decene and one or more of any of the monomers listed above.

The alpha-olefins used to make PAOs include, but are not limited to, $C_5$ to $C_{24}$ alpha-olefins, with the $C_6$ to $C_{14}$ alpha-olefins, such as 1-hexene, 1-heptene, 1-octene, 1-nonene, 1-decene, 1-undecene, 1-dodecene, 1-tridecene and 1-tetradecene being preferred. A preferred group of polyalphaolefins are poly-1-hexene, poly1-heptene, poly-1-octene, poly-1-nonene, poly-1-decene, poly1-undencen, poly-1-dodecene, poly-1-tridecene, and poly-1-tetradecene, although the dimers of higher olefins in the range of $C_{12}$ to $C_{18}$ can be present in the final products. Useful PAO's are preferably dimers, trimers, tetramers, pentamers, and higher oligomers or polymers with carbon numbers starting from $C_{20}$ and higher made from $C_4$ to $C_{18}$ alpha-olefins in one embodiment, and oligomers or polymers with carbon number starting from $C_{20}$ and higher made from $C_6$ to $C_{14}$ alpha-olefins in another embodiment. Suitable olefins include 1-butene, 1-pentene, 1-hexene, 1-heptene, 1-octene, 1-nonene, 1-decene, 1-undodecene and 1-dodecene, 1-tridecene, 1-tetradecene. In one embodiment, the olefin is 1-decene, and the PAO is a mixture of dimers, trimers, tetramers and pentamers (and higher) of 1-decene. In another embodiment, the olefin is 1-decene, and the PAO is a mixture of trimers, tetramers and pentamers (and higher) of 1-decene. In another embodiment, the olefin is 1-octene, and the PAO is a mixture of trimers, tetramers and pentamers (and higher) of 1-octene. In another embodiment, the olefin is 1-hexene, and the PAO is a mixture of tetramers and pentamers (and higher) of 1-hexene.

In another embodiment, the monomers comprise propylene and or butene, or combination of propylene and/or butene with another alpha-olefin or other olefins, choosing from C5 to C20 alpha-olefins.

In a preferred embodiment, the PAO comprises two or more monomers, preferably three or more monomers, preferably four or more monomers, preferably five or more monomers. For example, a C8, C10, C12-linear alpha-olefin mixture, or a C6, C7, C8, C9, C10, C11, C12, C13, C14-linear alpha-olefin mixture, or a C4, C6, C8, C10, C12, C14, C16, C18-linear alpha-olefin mixture can be used as a feed.

In an alternate embodiment, the PAO comprises less than 50 mole % of C2, C3 and C4 monomers, preferably less than 40 mole %, preferably less than 30 mole %, preferably less than 20 mole %, preferably less than 10 mole %, preferably less than 5 mole %, preferably less than 3 mole %, preferably 0%. Specifically, in an alternate embodiment, the PAO comprises less than 50 mole % of ethylene, propylene and butene, preferably less than 40 mole %, preferably less than 30 mole %, preferably less than 20 mole %, preferably less than 10 mole %, preferably less than 5 mole %, preferably less than 3 mole %, preferably 0%. In another embodiment, the PAO comprises less than 40 mole % of ethylene. In another embodiment, the PAO comprises less than 40 mole % of propylene. In another embodiment, the PAO comprises less than 40 mole % of butene. In another embodiment, the PAO comprises less than 10 mole % of ethylene. In another embodiment, the PAO comprises less than 10 mole % of propylene. In another embodiment, the PAO comprises less than 10 mole % of butene. In another embodiment, the PAO comprises less than 1 mole % of ethylene. In another embodiment, the PAO comprises less than 1 mole % of propylene. In another embodiment, the PAO comprises less than 1 mole % of butene.

In a preferred embodiment, ethylene, propylene and butene monomers are present in the PAO at less than 1 weight %.

The alpha-olefins used herein can be produced directly from ethylene growth process as practiced by several commercial production processes, or they can be produced from Fischer-Tropsch hydrocarbon synthesis from $CO/H_2$ syngas, or from metathesis of internal olefins with ethylene, or from cracking of petroleum or Fischer-Tropsch synthetic wax at high temperature, or any other alpha-olefin synthesis routes. A preferred feed for this invention is preferably at least 80 weight % alpha-olefin (preferably linear alpha olefin), preferably at least 90 weight % alpha-olefin (preferably linear alpha olefin), more preferably 100% alpha-olefin (preferably linear alpha olefin). However, alpha-olefin mixtures can also be used as feeds in this invention, especially if the other components are internal-olefins, branched olefins, paraffins, cyclic paraffins, aromatics (such as toluene and or xylenes). These components have diluent effects and are believed to not have a substantial detrimental effect on the polymerization of alpha-olefins. In other words, the process described herein can selectively convert alpha-olefins in a mixture and leave the other components unreacted. This is particularly useful when ethylene is not present in the mixture. This technology can be used to separate out alpha-olefins from a mixture by selectively reacting them with polymerization or oligomerization catalyst systems completely eliminating the need to separate alpha-olefins from the remainder of the components in a mixed feedstream. This is economically advantageous, for example, in a process utilizing Fisher-Tropsch synthesis olefin product streams containing alpha-olefins, internal-olefins and branched olefins. Such a mixture can be fed to the oligomerization technology as described herein and to selectively react away the alpha-olefin. No separate step to isolate the alpha-olefin is needed. Another example of the utility of this process involves alpha-olefins produced by the metathesis of internal olefins with ethylene, which may contain some internal olefins. This mixed olefin base stock feed can be reacted as is in the polymerization/oligomerization process of the present invention, which selectively converts the alpha-olefins into lube products. Thus one can use the alpha-olefin for the base stock synthesis without having to separate the alpha-olefin from internal olefin. This can bring a significant improvement in process economics. The feed olefins can be the mixture of olefins produced from other linear alpha-olefin process containing C4 to C20 alpha-olefins as described in Chapter 3 "Routes to Alpha-Olefins" of the book Alpha Olefins Applications Handbook, Edited by G. R. Lappin and J. D. Sauer, published by Marcel Dekker, Inc. N.Y. 1989.

In a preferred embodiment, the PAO's produced herein may contain monomers having branches at least 2, preferably at least 3 carbons away from the alpha-unsaturation, such 4-methyl-1-decene, 4-ethyl-1-decene, or 4-methyl-1-hexene, 4-methyl-1-pentene, etc. These olefins may be present in the linear alpha-olefins from the manufacturing process or they can be added deliberately. The copolymers of slightly branched alpha-olefins with completely linear alpha-olefins have improved low temperature properties.

In a preferred embodiment, any of the PAO's described herein may comprise at least 50 mole % 5 to 24 carbon atoms and from 0.5 to 20 mole % ethylene, where at least 80% of the ethylene present in the polyalpha-olefin is present in runs of 1 to 35 carbons or less as measured by Carbon 13 NMR. Preferably any of the PAO's described herein may comprise at least 60 mole % 5 to 24 carbon atoms (preferably at least 70 mole %, preferably at least 80 mole %, preferably at least 85 mole %, preferably at least 90 mole %, preferably at least 95 mole %) and from 0.5 to 20 mole % ethylene (preferably from 1 to 15 mole %, preferably from 2 to 10 mole %, preferably form 2 to 5 mole %), where at least 80% (preferably at least 85%, preferably at least 90%, preferably at least 95%, preferably at least 98%, preferably 100%) of the ethylene present in the polyalpha-olefin is present in runs of 1 to 35 carbons (preferably 1 to 30, preferably 1 to 25, preferably 1 to 20, preferably 1 to 15, preferably 1 to 10, preferably 1 to 5) as measured by Carbon 13 NMR.

Polymerization/Oligomerization Process

Many polymerization/oligomerization processes and reactor types used for metallocene-catalyzed polymerizations or oligomerizations such as solution, slurry, and bulk polymerization or oligomerization processed can be used in this invention. In some embodiments, if a solid or supported catalyst is used, a slurry or continuous fixed bed or plug flow process is suitable. In a preferred embodiment, the monomers are contacted with the metallocene compound and the activator in the solution phase, bulk phase, or slurry phase, preferably in a continuous stirred tank reactor or a continuous tubular reactor. In a preferred embodiment, the temperature in any reactor used herein is from −10° C. to 250° C., preferably from 30° C. to 220° C., preferably from 50° C. to 180° C., preferably from 60° C. to 170° C. In a preferred embodiment, the pressure in any reactor used herein is from 0.1 to 100 atmospheres, preferably from 0.5 to 75 atmospheres, preferably from 1 to 50 atmospheres. In another embodiment, the pressure is any reactor used herein is from 1 to 50,000 atmospheres, preferably 1 to 25,000 atmospheres. In another embodiment, the monomer(s), metallocene and activator are contacted for a residence time of 1 second to 100 hours, preferably 30 seconds to 50 hours, preferably 2 minutes to 6 hours, preferably 1 minute to 4 hours. In another embodiment solvent or diluent is present in the reactor and is preferably selected from the group consisting of butanes, pentanes, hexanes, heptanes, octanes, nonanes, decanes, undecanes, dodecanes, tridecanes, tetradecanes, pentadecanes, hexadecanes, toluene, o-xylene, m-xylene, p-xylene, mixed xylenes, ethylbenzene, isopropylbenzene, and n-butylbenzene; preferably toluene and or xylenes and or ethylbenzene, normal paraffins (such as Norpar solvents available for ExxonMobil Chemical Company in Houston, Tex.), or isoparaffin solvents (such as Isopar solvents available for ExxonMobil Chemical Company in Houston, Tex.). These solvents or diluents are usually pre-treated in same manners as the feed olefins.

Typically, in the processes of this invention, one or more transition metal compounds, one or more activators, and one or more monomers are contacted to produce polymer or oligomer. These catalysts may be supported and as such will be particularly useful in the known slurry, solution, or bulk operating modes conducted in single, series, or parallel reactors. If the catalyst, activator or co-activator is a soluble compound, the reaction can be carried out in a solution mode. Even if one of the components is not completely soluble in the reaction medium or in the feed solution, either at the beginning of the reaction or during or at the later stages of the reaction, a solution or slurry type operation is still applicable. In any instance, the catalyst components, dissolved or suspended insolvents, such as toluene or other conveniently available aromatic solvents, or in aliphatic solvent, or in the feed alpha-olefin stream, are fed into the reactor under inert atmosphere (usually nitrogen or argon blanketed atmosphere) to allow the polymerization or oligomerization to take place. The polymerization or oligomerization can be run in a batch mode, where all the components are added into a reactor and allowed to react to a pre-designed degree of conversion, either to partial conversion or full conversion. Subsequently, the catalyst is deactivated by any possible means, such as exposure to air or water, or by addition of alcohols or solvents containing deactivating agents. The polymerization or oligomerization can also be carried out in a semi-continuous operation, where feeds and catalyst system components are continuously and simultaneously added to the reactor so as to maintain a constant ratio of catalyst system components to feed olefin(s). When all feeds and catalyst components are added, the reaction is allowed to proceed to a pre-determined stage. The reaction is then discontinued by catalyst deactivation in the same manner as described for batch operation. The polymerization or oligomerization can also be carried out in a continuous operation, where feeds and catalyst system components are continuously and simultaneously added to the reactor so to maintain a constant ratio of catalyst system and feed olefins. The reaction product is continuously withdrawn from the reactor, as in a typical continuous stirred tank reactor (CSTR) operation. The residence times of the reactants are controlled by a pre-determined degree of conversion. The withdrawn product is then typically quenched in the separate reactor in a similar manner as other operation. In a preferred embodiment, any of the processes to prepare PAO's described herein are continuous processes. Preferably the continuous process comprises the steps of a) continuously introducing a feed stream comprising at least 10 mole % of the one or more C5 to C24 alpha-olefins into a reactor, b) continuously introducing the metallocene compound and the activator into the reactor, and c) continuously withdrawing the polyalpha-olefin from the reactor. In another embodiment, the continuous process comprises the step of maintaining a partial pressure of hydrogen in the reactor of 200 psi (1379 kPa) or less, based upon the total pressure of the reactor, preferably 150 psi (1034 kPa) or less, preferably 100 psi (690 kPa) or less, preferably 50 psi (345 kPa) or less, preferably 25 psi (173 kPa) or less, preferably 10 psi (69 kPa) or less. Alternately the hydrogen, if present is present in the reactor at 1000 ppm or less by weight, preferably 750 ppm or less, preferably 500 ppm or less, preferably 250 ppm or less, preferably 100 ppm or less, preferably 50 ppm or less, preferably 25 ppm or less, preferably 10 ppm or less, preferably 5 ppm or less. Alternately the hydrogen, if present, is present in the feed at 1000 ppm or less by weight, preferably 750 ppm or less, preferably 500 ppm or less, preferably 250 ppm or less, preferably 100 ppm or less, preferably 50 ppm or less, preferably 25 ppm or less, preferably 10 ppm or less, preferably 5 ppm or less.

Preferred reactors range in size from 2 ml and up. Usually, it is preferable to use reactors larger than one liter in volume for commercial production. The production facility may have one single reactor or several reactors arranged in series or in parallel or in both to maximize productivity, product properties and general process efficiency. The reactors and associated equipments are usually pre-treated to ensure proper reaction rates and catalyst performance. The reaction is usually conducted under inert atmosphere, where the catalyst system and feed components will not be in contact with any catalyst deactivator or poison which is usually polar oxygen, nitrogen, sulfur or acetylenic compounds.

One or more reactors in series or in parallel may be used in the present invention. The transition metal compound, activator and when required, co-activator, may be delivered as a solution or slurry in a solvent or in the alpha-olefin feed stream, either separately to the reactor, activated in-line just prior to the reactor, or preactivated and pumped as an activated solution or slurry to the reactor. Polymerizations/oligomerizations are carried out in either single reactor operation, in which monomer, or several monomers, catalyst/activator/co-activator, optional scavenger, and optional modifiers are added continuously to a single reactor or in series reactor operation, in which the above components are added to each of two or more reactors connected in series. The catalyst components can be added to the first reactor in the series. The catalyst component may also be added to both reactors, with one component being added to first reaction and another component to other reactors. In one preferred embodiment, the precatalyst is activated in the reactor in the presence of olefin. In another embodiment, the precatalyst such as the dichloride form of the metallocenes is pre-treated with alkylaluminum reagents, especially, triisobutylaluminum, tri-n-hexylaluminum and/or tri-n-octylaluminum, followed by charging into the reactor containing other catalyst component and the feed olefins, or followed by pre-activation with the other catalyst component to give the fully activated catalyst, which is then fed into the reactor containing feed olefins. In another alternative, the pre-catalyst metallocene is mixed with the activator and/or the co-activator and this activated catalyst is then charged into reactor, together with feed olefin stream containing some scavenger or co-activator. In another alternative, the whole or part of the co-activator is pre-mixed with the feed olefins and charged into the reactor at the same time as the other catalyst solution containing metallocene and activators and/or co-activator.

In some embodiments, a small amount of poison scavenger, such as trialkylaluminum (trimethylaluminum, triethylaluminum, triisopropylaluminum, triisobutylaluminum, tri-n-hexylaluminum, tri-n-octylaluminum) or methylalumoxane is added to the feed olefin stream to further improve catalyst activity. In a preferred embodiment, the monomers are contacted with an alkylaluminum compound, preferably a trialkylaluminum compound, prior to being introduced into the reactor. In another preferred embodiment, the metallocene and or activator are combined with an alkylaluminum compound, preferably a trialkylaluminum compound, prior to entering the reactor. Preferably the alkylaluminum compound is represented by the formula: $R_3Al$, where each R is independently a C1 to C20 alkyl group, preferably the R groups are independently selected from the group consisting of methyl, ethyl, propyl, isopropyl, butyl, isobutyl, n-butyl, pentyl, isopentyl, n-pentyl, hexyl, isohexyl, n-hexyl, heptyl, octyl, isoocotyl, n-octyl, nonyl, isononyl, n-nonyl, decyl, isodecyl, n-cecyl, undecyl, isoundecyl, n-undecyl, dodecyl, isododecyl, and n-dodecyl, preferably isobutyl, n-octyl, n-hexyl, and n-dodecyl. Preferably the alkylaluminum compound is selected from tri-isobutylaluminum, tri n-octylaluminum, tri-n-hexylaluminum, and tri-n-dodecylaluminum.

In one embodiment of any of the process described herein the feed olefins and or solvents are treated to remove catalyst poisons, such as peroxides, oxygen or nitrogen-containing organic compounds or acetylenic compounds. The treatment of the linear alpha-olefin with an activated 13X molecular sieve and a de-oxygenate catalyst, i.e., a reduced copper catalyst, increased catalyst productivity more than 10-fold. Alternatively, the feed olefins and or solvents are treated with an activated molecular sieve, such as 3A, 4A, 8A or 13X molecular sieve, and/or in combination with an activated alumina or an activated de-oxygenated catalyst. Such treatment will increase catalyst productivity 2- to 10-fold or more. The improved process also includes special treatment of the feed olefins to remove catalyst poisons, such as peroxides, oxygen, sulfur or nitrogen-containing organic compounds or other trace impurities. This treatment can increase catalyst productivity substantially (typically more than 10-fold). Preferably the feed olefins are contacted with a molecular sieve, activated alumina, silica gel, oxygen removing catalyst, and or purifying clays to reduce the heteroatom-containing compounds in the feed, preferably below 50 ppm, preferably below 10 ppm.

The catalyst compositions can be used individually or can be mixed with other known polymerization catalysts to prepare polymer or oligomer blends. Monomer and catalyst selection allows polymer or oligomer blend preparation under conditions analogous to those using individual catalysts. Polymers having increased MWD are available from polymers made with mixed catalyst systems and can thus be achieved. Mixed catalyst can comprise two or more catalyst precursors and or two or more activators.

Generally, when using metallocene catalysts, after pre-treatment of feed olefins, solvents, diluents and after precautions to keep the catalyst component stream(s) and reactor free of impurities, the reaction should proceed well. In some embodiments, when using metallocene catalysts, particularly when they are immobilized on a support, the complete catalyst system will additionally comprise one or more scavenging compounds. Here, the term scavenging compound means a compound that removes polar impurities from the reaction environment. These impurities adversely affect catalyst activity and stability. Typically, purifying steps are usually used before introducing reaction components to a reaction vessel. But such steps will rarely allow polymerization or oligomerization without using some scavenging compounds. Normally, the polymerization process will still use at least small amounts of scavenging compounds.

Typically, the scavenging compound will be an organometallic compound such as the Group-13 organometallic compounds of U.S. Pat. Nos. 5,153,157, 5,241,025 and WO-A-91/09882, WO-A-94/03506, WO-A-93/14132, and that of WO 95/07941. Exemplary compounds include triethylaluminum, triethylborane, tri-iso-butylaluminum, diisobutylaluminum hydride, methylalumoxane, iso-butylalumoxane, and tri-n-octylaluminum. Those scavenging compounds having bulky or $C_6$-$C_{20}$ linear hydrocarbyl substituents connected to the metal or metalloid center usually minimize adverse interaction with the active catalyst. Examples include triethylaluminum, but more preferably, bulky compounds such as tri-iso-butyl aluminum, tri-iso-prenyl aluminum, and long-chain linear alkyl-substituted aluminum compounds, such as tri-n-hexyl aluminum, tri-n-octyl aluminum, or tri-n-dodecyl aluminum. When alumoxane is used as the activator, any excess over that needed for activation will scavenge impurities and additional scavenging compounds may be unnecessary. Alumoxanes also may be added in scavenging quantities with other activators, e.g., methylalumoxane, $[Me_2HNPh]^+[B(pfp)_4]^-$ or $B(pfP)_3$, where pfp is perfluorophenyl ($C_6F_5$), Me is methyl and Ph is phenyl.

In a preferred embodiment ethylene is present in the feed at 10 mole % or less, preferably 0.5 to 8 moles %, preferably 0.5 to 5 mole %, preferably from 1 to 3 mole %

The PAO's described herein can also be produced in homogeneous solution processes. Generally this involves polymerization or oligomerization in a continuous reactor in which the polymer formed and the starting monomer and catalyst materials supplied, are agitated to reduce or avoid concentration or temperature gradients. Temperature control in the reactor is generally obtained by balancing the heat of polymerization and with reactor cooling by reactor jackets or cooling coils or a cooled side-stream of reactant to cool the contents of the reactor, auto refrigeration, pre-chilled feeds, vaporization of liquid medium (diluent, monomers or solvent) or combinations of the above. Adiabatic reactors with pre-chilled feeds may also be used. The reactor temperature depends on the catalyst used and the product desired. Higher temperatures tend to give lower molecular weights and lower temperatures tend to give higher molecular weights, however this is not a hard and fast rule. In general, the reactor temperature preferably can vary between about 0° C. and about 300° C., more preferably from about 10° C. to about 230° C., and most preferably from about 25° C. to about 200° C. Usually, it is important to control the reaction temperature as pre-determined. In order to produce fluids with narrow molecular distribution, such as to promote the highest possible shear stability, it is useful to control the reaction temperature to obtain minimum of temperature fluctuation in the reactor or over the course of the reaction time. If multiple reactors are used in series or in parallel, it is useful to keep the temperature constant in a pre-determined value to minimize any broadening of molecular weight distribution. In order to produce fluids with broad molecular weight distribution, one can adjust the reaction temperature swing or fluctuation, or as in series operation, the second reactor temperature is preferably higher than the first reactor temperature. In parallel reactor operation, the temperatures of the two reactors are independent. Or one can use two types of metallocene catalysts.

The pressure in any reactor used herein can vary from about 0.1 atmosphere to 100 atmosphere (1.5 psi to 1500 psi), preferably from 0.5 bar to 75 atm (8 psi-1125 psi), most preferably from 1.0 to 50 atm (15 psi to 750 psi). The reaction can be carried out under the atmosphere of nitrogen or with some hydrogen. Sometimes a small amount of hydrogen is added to the reactor to improve the catalyst. The amount of hydrogen is preferred to keep at such a level to improve catalyst productivity, but not induce any hydrogenation of olefins, especially the feed alpha-olefins because the conversion of alpha-olefins into saturated paraffins is very detrimental to the efficiency of the process. The amount of hydrogen partial pressure is preferred to be kept low, less than 50 psi, preferably less than 25 psi, preferably less than 10 psi, preferably less than 5 psi. In a particularly preferred embodiment in any of the process described herein the concentration of hydrogen in the reactant phase is less than 10,000 ppm, 100 ppm, preferably less than 50 ppm, preferably less than 10 ppm. In a particularly preferred embodiment in any of the process described herein the concentration of hydrogen in the reactor is kept at a partial pressure of preferably 50 psi (345 kPa) or less, preferably 10 psi (69 kPa) or less. Alternately, in any process described herein hydrogen, if present, is present in the reactor and or feed at 10,000 ppm or less, preferably 1000 ppm or less by weight, preferably 750 ppm or less, preferably 500 ppm or less, preferably 250 ppm or less, preferably 100 ppm or less, preferably 50 ppm or less, preferably 25 ppm or less.

The reaction time or reactor residence time is usually dependent on the type of catalyst used, the amount of catalyst used, and the desired conversion level. Different metallocenes have different activities. Usually, a higher degree of alkyl substitution on the cyclopentadienyl ring, or bridging improves catalyst productivity. Catalysts such as bis(1,2,3,4-tetramethylcyclopentadienyl)zirconium dichloride or bis(1,2,4-tri methylcyclopentadienyl)zirconium dichloride, (1,2,3,4-tetramethylcyclopentadienyl)(1,3-di methylcyclopentadienyl)zirconium dichloride or (1,2,4-tri methylcyclopentadienyl)(1,3-di methylcyclopentadienyl) zirconium dichloride or their dialkyl analogs have desirable high productivity and stability than unsubstituted metallocenes. Usually the amount of catalyst components used is determinative. High amount of catalyst loading tends to gives high conversion at short reaction time. However, high amount of catalyst usage make the production process uneconomical and difficult to manage the reaction heat or to control the reaction temperature. Therefore, it is useful to choose a catalyst with maximum catalyst productivity to minimize the amount of metallocene and the amount of activators needed. When the catalyst system is metallocene plus methylalumoxane, the range of methylalumoxane used is typically in the range of 0.1 milligram (mg) to 500 mg/g of alpha-olefin feed. A more preferred range is from 0.05 mg to 10 mg/g of alpha-olefin feed. Furthermore, the molar ratios of the aluminum to metallocene (Al/M molar ration) range from 2 to 4000, preferably 10 to 2000, more preferably 50 to 1000, preferably 100 to 500. When the catalyst system is metallocene plus a Lewis Acid or an ionic promoter with NCA component, the metallocene use is typically in the range of 0.01 microgram to 500 micrograms of metallocene component/gram of alpha-olefin feed. Usually the preferred range is from 0.1 microgram to 100 microgram of metallocene component per gram of alpha-olefin feed. Furthermore, the molar ratio of the NCA activator to metallocene is in the range from 0.1 to 10, preferably 0.5 to 5, preferably 0.5 to 3. If a co-activator of alkylaluminum compound is used, the molar ratio of the Al to metallocene is in the range from 1 to 1000, preferably 2 to 500, preferably 4 to 400.

Typically one prefers to have the highest possible conversion (close to 100%) of feed alpha-olefin in shortest possible reaction time. However, in CSTR operation, sometimes it is beneficial to run the reaction at an optimum conversion, which is slightly less than 100% conversion. There are also occasions, when partial conversion is more desirable when the narrowest possible MWD of the product is desirable because partial conversion can avoid a MWD broadening effect. If the reaction is conducted to less than 100% conversion of the alpha-olefin, the unreacted starting material after separation from other product and solvents/diluents can be recycled to increase the total process efficiency.

Desirable residence times for any process described herein are in the range from 1 minutes to 20 hours, typically 5 minutes to 10 hours. Each of these processes may also be employed in single reactor, parallel or series reactor configurations. The liquid processes comprise contacting olefin monomers with the above described catalyst system in a suitable diluent or solvent and allowing said monomers to react for a sufficient time to produce the desired polymers or oligomers. Hydrocarbon solvents both aliphatic and aromatic are suitable. Aromatics such as toluene, xylenes, ethylbenzene, propylbenzene, cumene, t-butylbenzene are suitable. Alkanes, such as hexane, heptane, pentane, isopentane, and octane, Norpar or Isopar solvents from ExxonMobil Chemical Company in Houston, Tex. are also suitable. Generally, toluene is most suitable to dissolve catalyst components. Norpar, Isopar solvent or hexanes are preferred as reaction diluents. Oftentimes, a mixture of toluene and Norpar or Isopar is used as diluent or solvent.

The process can be carried out in a continuous stirred tank reactor or plug flow reactor, or more than one reactor operated in series or parallel. These reactors may have or may not have internal cooling and the monomer feed may or may not be refrigerated. See the general disclosure of U.S. Pat. No. 5,705,577 for general process conditions.

When a solid supported catalyst is used for the conversion, a slurry polymerization/oligomerization process generally operates in the similar temperature, pressure and residence time range as described previously. In a slurry polymerization or oligomerization, a suspension of solid catalyst, promoters, monomer and comonomers are added. The suspension including diluent is intermittently or continuously removed from the reactor. The catalyst is then separated from the product by filtration, centrifuge or settlement. The fluid is then distilled to remove solvent, any unreacted components and light product. A portion or all of the solvent and unreacted component or light components can be recycled for reuse.

If the catalyst used is un-supported, is a solution catalyst, when the reaction is complete or when the product is withdrawn from the reactor (such as in a CSTR), the product may still contain soluble, suspended or mixed catalyst components. These components are preferably deactivated or removed. Any of the usual catalyst deactivation methods or aqueous wash methods can be used to remove the catalyst component. Typically, the reaction is deactivated by addition of stoichiometric amount or excess of air, moisture, alcohol, isopropanol, etc. The mixture is then washed with dilute sodium hydroxide or with water to remove catalyst components. The residual organic layer is then subjected to distillation to remove solvent, which can be recycled for reuse. The distillation can further remove any light reaction product from C18 and less. These light components can be used as diluent for further reaction. Or they can be used as olefinic raw material for other chemical synthesis, as these light olefin product have vinylidene unsaturation, most suitable for further functionalization to convert in high performance fluids. Or these light olefin products can be hydrogenated to be used as high quality paraffinic solvents.

Polymerization or oligomerization in absence of hydrogen is also advantageous to provide polymers or oligomers with high degree of unsaturated double bonds. These double bonds can be easily converted into functionalized fluids with multiple performance features. Examples for converting these polymers with MW greater than 300 can be found in preparation of ashless dispersants, by reacting the polymers with maleic anhydride to give PAO-succinic anhydride which can then reacted with amines, alcohols, polyether alcohols to convert into dispersants. Examples for such conversion can be found in the book "Lubricant Additives: Chemistry and Application," ed. By Leslie R. Rudnick, p. 143-170.

In another embodiment, any of polyalphaolefins produced herein is hydrogenated. In particular the polyalpha-olefin is preferably treated to reduce heteroatom containing compounds to less than 600 ppm, and then contacted with hydrogen and a hydrogenation catalyst to produce a polyalpha-olefin having a bromine number less than 1.8. In a preferred embodiment, the treated polyalpha-olefin comprises 100 ppm of heteroatom containing compounds or less, preferably 10 ppm of heteroatom containing compounds or less. (A heteroatom containing compound is a compound containing at least one atom other than carbon and hydrogen.) Preferably the hydrogenation catalyst is selected from the group consisting of supported Group 7, 8, 9, and 10 metals, preferably the hydrogenation catalyst selected from the group consisting of one or more of Ni, Pd, Pt, Co, Rh, Fe, Ru, Os, Cr, Mo, and W, supported on silica, alumina, clay, titania, zirconia, or mixed metal oxide supports. A preferred hydrogenation catalyst is nickel supported on kieselguhr, or platinum or palladium supported on alumina, or cobalt-molydenum supported on alumina. Usually, a high nickel content catalyst, such as 60% Ni on Keiselguhr catalyst is used, or a supported catalyst with high amount of Co—Mo loading. Alternately, the hydrogenation catalyst is nickel supported on keisleghur, silica, alumina, clay or silica-alumina.

In a preferred embodiment the polyalpha-olefin is contacted with hydrogen and a hydrogenation catalyst at a temperature from 25 to 350° C., preferably 100 to 300° C. In another preferred embodiment the polyalpha-olefin is contacted with hydrogen and a hydrogenation catalyst for a time period from 5 minutes to 100 hours, preferably from 5 minutes to 24 hours. In another preferred embodiment the polyalpha-olefin is contacted with hydrogen and a hydrogenation catalyst at a hydrogen pressure of from 25 psi to 2500 psi, preferably from 100 to 2000 psi. In another preferred embodiment the hydrogenation process reduces the number of mm triad groups in a polyalpha-olefin by 1 to 80%. Preferably the PAO has 10 to 80% less mm triad groups than the polyalpha-olefin prior to contact with the hydrogen and hydrogenation catalyst. For further information on hydrogenation of PAO's please see U.S. Pat. No. 5,573,657 and "Lubricant Base Oil Hydrogen Refining Processes" (page 119 to 152 of Lubricant Base Oil and Wax Processing, by Avilino Sequeira, Jr., Marcel Dekker, Inc., NY, 1994.

This hydrogenation process can be accomplished in a slurry reactor in a batch operation or in a continuous stirred tank reactor (CSTR), where the catalyst in 0.001 wt % to 20 wt % of the PAO feed or preferably 0.01 to 10 wt %, hydrogen and the polyalpha-olefins are continuously added to the reactor to allow for certain residence time, usually 5 minutes to 10 hours to allow complete hydrogenation of the unsaturated olefins and to allow proper conversion of the mm diads. The amount of catalyst added is usually very small just to compensate for the catalyst deactivation. The catalyst and hydrogenated PAO are continuously withdrawn from the reactor. The product mixture was then filtered, centrifuged or settled to remove the solid hydrogenation catalyst. The catalyst can be regenerated and reused. The hydrogenated PAO can be used as is or further distilled or fractionated to the right component if necessary. In some cases, when the hydrogenation catalyst show no catalyst deactivation over long term operation, the stir tank hydrogenation process can be carried out in a manner where a fixed amount of catalyst is maintained in the reactor, usually 0.1 wt % to 10% of the total reactant, and only hydrogen and PAO feed are continuously added at certain feed rate and only hydrogenated PAO was withdrawn from the reactor.

The hydrogenation process can also be accomplished by a fixed bed process, in which the solid catalyst is packed inside a tubular reactor and heated to reactor temperature. Hydrogen and PAO feed can be fed through the reactor simultaneously from the top or bottom or countercurrently to maximize the contact between hydrogen, PAO and catalyst and to allow best heat management. The feed rate of the PAO and hydrogen are adjusted to give proper residence to allow complete hydrogenation of the unsaturated olefins in the feed and to allow desirable conversion of mm triads in the process. The hydrogenated PAO fluid can be used as is or further distilled or fractionated to give the right component, if necessary. Usually, the finished hydrocarbon PAO fluids have bromine number less than 2 and have reduced amount of mm triads than the unhydrogenated PAO.

The new poly-alpha-olefins when used alone or blended with other fluid has unique lubrication properties.

In another embodiment, a novel lubricant of the present invention comprises the PAO's produced in this invention, together with one or more other base stocks, including Group I to Group V base stocks with viscosity range from 1.5 to 100 cSt at 100° C. to formulate suitable viscosity grades. In addition, additives of one or more of: thickeners, VI improvers, antioxidants, anti-wear additives, detergent/dispersant/inhibitor (DDI) packages, and/or anti-rust additives may be added. In a preferred embodiment the PAO's produced herein are combined with one or more of dispersants, detergents, friction modifiers, traction improving additives, demulsifiers, defoamants, chromophores (dyes), and/or haze inhibitors. These fully formulated lubricants can be used in automotive crank case oil (engine oil), industrial oil, grease, or gas turbine engine oil. These are examples of additives used in finished lubricant formulations. Additional information on the use of PAO's in the formulations of full synthetic, semi-synthetic or part synthetic lubricant or functional fluids can be found in "Synthetic Lubricants and High-Performance Functional Fluids", 2nd Ed. L. Rudnick, etc. Marcel Dekker, Inc., N.Y. (1999). Additional information on additives used in product formulation can be found in "Lubricants and Lubrications, Ed. By T. Mang and W. Dresel, by Wiley-VCH GmbH, Weinheim 2001.

In another embodiment, this invention relates to:

1. A process to produce a polyalpha-olefin comprising:

1) contacting one or more alpha-olefin monomers having 3 to 24 carbon atoms with an unbridged substituted bis cyclopentadienyl transition metal compound having: 1) at least one non-isoolefin substitution on both cyclopentadienyl rings, or 2) at least two substitutions on at least one cyclopentadienyl ring, a non-coordinating anion activator, and optionally an alkyl-aluminum compound, where the molar ratio of transition metal compound to activator is 10:1 to 0.1:1, and if the alkyl aluminum compound is present then the molar ratio of alkyl aluminum compound to transition metal compound is 1:4 to 4000:1, under polymerization conditions wherein:

i) hydrogen is present at a partial pressure of 0.1 to 50 psi, based upon the total pressure of the reactor or the concentration of the hydrogen is from 1 to 10,000 ppm or less by weight;

ii) wherein the alpha-olefin monomer(s) having 3 to 24 carbon atoms are present at 10 volume % or more based upon the total volume of the catalyst/activator/alkylaluminum compound solutions, monomers, and any diluents or solvents present in the reaction;

iii) the residence time of the reaction is at least 5 minutes;

iv) the productivity of the process is at least 43,000 grams of total product per gram of transition metal compound;

v) the process is continuous or semi-continuous, and vi) the temperature in the reaction zone does not rise by more than 10° C. during the reaction; and vii) ethylene is not present at more than 30 volume % of the monomers entering the reaction zone; and 2) obtaining a polyalpha-olefin (PAO), optionally hydrogenating the PAO, wherein the PAO comprises at least 50 mole % of a C3 to C24 alpha-olefin monomer, and wherein the PAO has a kinematic viscosity at 100° C. of 20 cSt or less.

2. The process of paragraph 1 wherein the transition metal compound is represented by the formula:

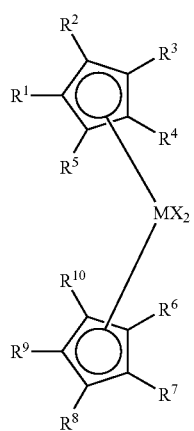

where M is a Group 4 metal;

each X is a hydrogen, halogen, hydride radicals, hydrocarbyl radicals, substituted hydrocarbyl radicals, halocarbyl radicals, substituted halocarbyl radicals, silylcarbyl radicals, substituted silylcarbyl radicals, germylcarbyl radicals, or substituted germylcarbyl radicals, or both X are joined and bound to the metal atom to form a metallacycle ring containing from about 3 to about 20 carbon atoms, or both together can be an olefin, diolefin or aryne ligand; and $R^1$ to $R^{10}$ are independently, a radical group which is a hydrogen, a heteroatom, hydrocarbyl, substituted hydrocarbyl, halocarbyl, substituted halocarbyl, silylcarbyl or germylcarbyl, provided that: 1) at least one of $R^1$ to $R^5$ is not hydrogen or an isoolefin and at least one of $R^6$ to $R^{10}$ is not hydrogen or an isoolefin or 2) at least two of $R^1$ to $R^5$ are not hydrogen, or 3) at least two of $R^1$ to $R^5$ are not hydrogen and at least two of $R^6$ to $R^{10}$ are not hydrogen, and where any two adjacent $R^1$ to $R^5$ groups may form a C4 to C20 cyclic or poly cyclic moiety, and where any two adjacent $R^6$ to $R^{10}$ groups may form a C4 to C20 cyclic or poly cyclic moiety.

3. The process of paragraph 1 or 2 wherein the PAO has a pour point of 0° C. or less.

4. The process of paragraph 1, or 3 wherein the PAO has a pour point of –40° C. or less and a kinematic viscosity at 100° C. of 15 cSt or less.

5. The process of any of paragraphs 1 to 4 wherein the PAO has a pour point of –55° C. or less and a kinematic viscosity at 100° C. of 10 cSt or less.

6. The process of any of paragraphs 1 to 5 wherein the polyalpha-olefin is polydecene having an Mw/Mn of between 1 and 3.5.

7. The process of any of paragraphs 1 to 6 wherein the polyalpha-olefin has a Bromine number of 1.8 or more.

8. The process of any of paragraphs 1 to 7 wherein the polyalpha-olefin has a Kinematic viscosity at 100° C. of from 1.5 to 15 cSt.

9. The process of any of paragraphs 1 to 8 wherein the polyalpha-olefin has a Kinematic viscosity at 100° C. of from 1.7 to 12 cSt.

10. The process of any of paragraphs 1 to 9 wherein the polyalpha-olefin has a kinematic viscosity at 40° C. of from 3 to 1,000 cSt.

11. The process of any of paragraphs 1 to 10 wherein the polyalpha-olefin has a Viscosity Index of 90 or more.

12. The process of any of paragraphs 1 to 11 wherein the polyalpha-olefin has a Viscosity Index of 90 to 200.

13. The process of any of paragraphs 1 to 12 wherein the polyalpha-olefin has a pour point of –40° C. or less.

14. The process of any of paragraphs 1 to 13 wherein the polyalpha-olefin has a weight average molecular weight of 100 to 50,000 g/mol.

15. The process of any of paragraphs 1 to 14 wherein the polyalpha-olefin has a weight average molecular weight of 336 to 40,000 g/mol.

16. The process of any of paragraphs 1 to 15 wherein the monomers having 3 to 24 carbon atoms are present at 55 mole % or more.

17. The process of any of paragraphs 1 to 16 wherein monomers having 5 to 24 carbon atoms are present at 55 mole % or more.

18. The process of any of paragraphs 1 to 17 wherein the polyalpha-olefin(s) are selected from the group consisting of 1-butene, 1-pentene, 1-hexene, 1-heptene, 1-octene, 1-nonene, 1-decene, 1-undecene, 1-dodecene, 1-tridecene, 1-tetradecene, 1-pentadecene, 1-hexadecene, 1-heptadecene, 1-octadecene, 1-nonadecene, 1-eicosene, 1-uneicosene, 1-docosene, 1-tricosene, 1-tetracosene, 1-pentacosene, 1-hexacosene, 4-methyl-1-pentene, 4-phenyl-1-butene, and 5-phenyl-1-pentene.

19. The process of any of paragraphs 1 to 18 wherein the polyalpha-olefin(s) are selected from the group consisting of 1-pentene, 1-hexene, 1-heptene, 1-octene, 1-nonene, 1-decene, 1-undecene, 1-dodecene, 1-tridecene, 1-tetradecene, 1-pentadecene and 1-hexadecene.

20. The process of any of paragraphs 1 to 19 wherein the polyalpha-olefin(s) are selected from the group consisting of 1-hexene, 1-octene, 1-decene, 1-dodecene, 1-tetradecene and 1-hexadecene.

21. The process of any of paragraphs 1 to 20 wherein the polyalpha-olefin comprises octene, decene, and dodecene.

22. The process of any of paragraphs 1 to 21 wherein the polyalpha-olefin has a dielectric constant of 2.5 or less (1 kHz at 23° C.).

23. The process of any of paragraphs 1 to 22 wherein the polyalpha-olefin has a flash point of 150° C. or more.

24. The process of any of paragraphs 1 to 23 wherein the polyalpha-olefin has a specific gravity of 0.75 to 0.96 g/cm$^3$.

25. The process of any of paragraphs 1 to 24 wherein ethylene, propylene and butene monomers are present at less than 1 weight %.

26. The process of any of paragraphs 1 to 25 wherein the monomers having 5 to 24 carbon atoms are present at 60 mole % or more.

27. The process of any of paragraphs 1 to 26 wherein the monomers having 5 to 24 carbon atoms are present at 70 mole % or more.

28. The process of any of paragraphs 1 to 27 further comprising
  1) optionally treating the polyalpha-olefin to reduce heteroatom containing compounds to less than 600 ppm,
  2) optionally separating the polyalpha-olefins from solvents or diluents;
  3) contacting the polyalpha-olefin with hydrogen and a hydrogenation catalyst; and
  4) obtaining a polyalpha-olefin having a bromine number less than 1.8.

29. The process of paragraph 28 wherein the polyalpha-olefin is treated to remove heteroatom containing compounds prior to contacting with the hydrogen and or the hydrogenation catalyst.

30. The process of paragraph 29 wherein the treated polyalpha-olefin comprises 100 ppm of heteroatom containing compounds or less.

31. The process of paragraph 29 wherein the treated polyalpha-olefin comprises 10 ppm of heteroatom containing compounds or less.

32. The process of any of paragraphs 1 to 31 where scavenger is present and comprises methylalumoxane and or modified methylalumoxane.

33. The process of any of paragraphs 1 to 32 wherein the activator comprises one or more of N,N-dimethylanilinium tetra(pentafluorophenyl)borate, N,N-dialkylphenylanilinium tetra(pentafluorophenyl)borate (where the alkyl is a C1 to C18 alkyl group), trityl tetra(pentafluorophenyl)borate, tris(pentafluorophenyl)boron, tri-alkylammonium tetra(pentafluorophenyl)borate (where the alkyl is a C1 to C18 alkyl group), tetra-alkylammonium tetra(pentafluorophenyl)borate (where the alkyl is a C1 to C18 alkyl group).

34. The process of any of paragraphs 1 to 33 wherein the transition metal compound comprises one or more of:
bis(1,2,4-trimethylcyclopentadienyl)zirconium dichloride;
bis(1,3-dimethylcyclopentadienyl)zirconium dichloride;
bis(tetramethylcyclopentadienyl)zirconium dichloride;
bis(pentamethylcyclopentadienyl)zirconium dichloride;
bis(1,2,4-trimethylcyclopentadienyl)zirconium dimethyl;
bis(1,3-dimethylcyclopentadienyl)zirconium dimethyl;
bis(tetramethylcyclopentadienyl)zirconium dimethyl; or
bis(pentamethylcyclopentadienyl)zirconium dimethyl.

35. The process of any of paragraphs 1 to 34 wherein the transition metal compound comprises one or more of:
Bis(1,2-dimethylcyclopentadienyl)zirconium dichloride,
Bis(1,3-dimethylcyclopentadienyl)zirconium dichloride,
Bis(1,2,3-trimethylcyclopentadienyl)zirconium dichloride,
Bis(1,2,4-trimethylcyclopentadienyl)zirconium dichloride,
Bis(1,2,3,4-tetramethylcyclopentadienyl)zirconium dichloride,
Bis(1,2,3,4,5-pentamethylcyclopentadienyl)zirconium dichloride,
Bis(1-methyl-2-ethylcyclopentadienyl)zirconium dichloride,
Bis(1-methyl-2-n-propylcyclopentadienyl)zirconium dichloride,
Bis(1-methyl-2-n-butyllcyclopentadienyl)zirconium dichloride,
Bis(1-methyl-3-ethylcyclopentadienyl)zirconium dichloride,
Bis(1-methyl-3-n-propylcyclopentadienyl)zirconium dichloride,
Bis(1-methyl-3-n-butylcyclopentadienyl)zirconium dichloride,
Bis(1-methyl-3-n-pentylcyclopentadienyl)zirconium dichloride,
Bis(1,2-dimethyl-4-ethylcyclopentadienyl)zirconium dichloride,
Bis(1,2-dimethyl-4-n-propylcyclopentadienyl)zirconium dichloride,
Bis(1,2-dimethyl-4-n-butylcyclopentadienyl)zirconium dichloride,
Bis(1,2-diethylcyclopentadienyl)zirconium dichloride,
Bis(1,3-diethylcyclopentadienyl)zirconium dichloride,
Bis(1,2-di-n-propylcyclopentadienyl)zirconium dichloride,
Bis(1,2-di-n-butylcyclopentadienyl)zirconium dichloride,
Bis(1-methyl-2,4-diethylcyclopentadienyl)zirconium dichloride,
Bis(1,2-diethyl-4-n-propylcyclopentadienyl)zirconium dichloride,
Bis(1,2-diethyl-4-n-butylcyclopentadienyl)zirconium dichloride,
Bis(1-methyl-3-i-propylcyclopentadienyl)zirconium dichloride,
Bis(1-ethyl-3-i-propylcyclopentadienyl)zirconium dichloride,
(1,2-dimethylcyclopentadienyl)(cyclopentadienyl)zirconium dichloride,
(1,3-dimethylcyclopentadienyl)(cyclopentadienyl)zirconium dichloride,
(1,2-dimethylcyclopentadienyl)(methylcyclopentadienyl)zirconium dichloride,
(1,2-dimethylcyclopentadienyl)(ethylcyclopentadienyl)zirconium dichloride,
(1,2-dimethylcyclopentadienyl)(1,2-di-n-butylcyclopentadienyl)zirconium dichloride,
(1,3-dimethylcyclopentadienyl)(cyclopentadienyl)zirconium dichloride,
(1,3-dimethylcyclopentadienyl)(1,2-dimethylcyclopentadienyl)zirconium dichloride,
(1,3-dimethylcyclopentadienyl)(1,3-diethylcyclopentadienyl)zirconium dichloride,
Bis(indenyl)zirconium dichloride,
Bis(1-methylindenyl)zirconium dichloride, Bis(2-methylindenyl)zirconium dichloride,
Bis(4-methylindenyl)zirconium dichloride,
Bis(4,7-dimethylindenyl)zirconium dichloride,
Bis(4,5,6,7-tetrahydroindenyl)zirconium dichloride,
Bis(4,5,6,7-tetrahydro-2-methylindenyl)zirconium dichloride,
Bis(4,5,6,7-tetrahydro-4,7-dimethylindenyl)zirconium dichloride,
(Cyclopentadienyl)(4,5,6,7-tetrahydroindenyl)zirconium dichloride,
Bis(1,2-dimethylcyclopentadienyl)zirconium dimethyl,
Bis(1,3-dimethylcyclopentadienyl)zirconium dimethyl,
Bis(1,2,3-trimethylcyclopentadienyl)zirconium dimethyl,
Bis(1,2,4-trimethylcyclopentadienyl)zirconium dimethyl,
Bis(1,2,3,4-tetramethylcyclopentadienyl)zirconium dimethyl,
Bis(1,2,3,4,5-pentamethylcyclopentadienyl)zirconium dimethyl,
Bis(1-methyl-2-ethylcyclopentadienyl)zirconium dimethyl,
Bis(1-methyl-2-n-propylcyclopentadienyl)zirconium dimethyl,
Bis(1-methyl-2-n-butyllcyclopentadienyl)zirconium dimethyl,
Bis(1-methyl-3-ethylcyclopentadienyl)zirconium dimethyl,
Bis(1-methyl-3-n-propylcyclopentadienyl)zirconium dimethyl,
Bis(1-methyl-3-n-butylcyclopentadienyl)zirconium dimethyl,
Bis(1-methyl-3-n-pentylcyclopentadienyl)zirconium dimethyl,
Bis(1,2-dimethyl-4-ethylcyclopentadienyl)zirconium dimethyl,
Bis(1,2-dimethyl-4-n-propylcyclopentadienyl)zirconium dimethyl,
Bis(1,2-dimethyl-4-n-butylcyclopentadienyl)zirconium dimethyl,
Bis(1,2-diethylcyclopentadienyl)zirconium dimethyl,
Bis(1,3-diethylcyclopentadienyl)zirconium dimethyl,
Bis(1,2-di-n-propylcyclopentadienyl)zirconium dimethyl,
Bis(1,2-di-n-butylcyclopentadienyl)zirconium dimethyl,
Bis(1-methyl-2,4-diethylcyclopentadienyl)zirconium dimethyl,
Bis(1,2-diethyl-4-n-propylcyclopentadienyl)zirconium dimethyl,
Bis(1,2-diethyl-4-n-butylcyclopentadienyl)zirconium dimethyl,
Bis(1-methyl-3-i-propylcyclopentadienyl)zirconium dimethyl,
Bis(1-ethyl-3-i-propylcyclopentadienyl)zirconium dimethyl,
(1,2-dimethylcyclopentadienyl)(cyclopentadienyl)zirconium dimethyl,
(1,3-dimethylcyclopentadienyl)(cyclopentadienyl)zirconium dimethyl,
(1,2-dimethylcyclopentadienyl)(methylcyclopentadienyl)zirconium dimethyl,
(1,2-dimethylcyclopentadienyl)(ethylcyclopentadienyl)zirconium dimethyl,
(1,2-dimethylcyclopentadienyl)(1,2-di-n-butylcyclopentadienyl)zirconium dimethyl,
(1,3-dimethylcyclopentadienyl)(cyclopentadienyl)zirconium dimethyl,
(1,3-dimethylcyclopentadienyl)(1,2-dimethylcyclopentadienyl)zirconium dimethyl,
(1,3-dimethylcyclopentadienyl)(1,3-diethylcyclopentadienyl)zirconium dimethyl,
Bis(indenyl)zirconium dimethyl,
Bis(1-methylindenyl)zirconium dimethyl,
Bis(2-methylindenyl)zirconium dimethyl,
Bis(4-methylindenyl)zirconium dimethyl,
Bis(4,7-dimethylindenyl)zirconium dimethyl,
Bis(4,5,6,7-tetrahydroindenyl)zirconium dimethyl,
Bis(4,5,6,7-tetrahydro-2-methylindenyl)zirconium dimethyl,
Bis(4,5,6,7-tetrahydro-4,7-dimethylindenyl)zirconium dimethyl, or
(Cyclopentadienyl)(4,5,6,7-tetrahydroindenyl)zirconium dimethyl.

36. The process of any of paragraphs 1 to 34 wherein the transition metal compound comprises one or more of:
Bis(1,2-dimethylcyclopentadienyl)hafnium dichloride,
Bis(1,3-dimethylcyclopentadienyl)hafnium dichloride,
Bis(1,2,3-trimethylcyclopentadienyl)hafnium dichloride,
Bis(1,2,4-trimethylcyclopentadienyl)hafnium dichloride,
Bis(1,2,3,4-tetramethylcyclopentadienyl)hafnium dichloride,
Bis(1,2,3,4,5-pentamethylcyclopentadienyl)hafnium dichloride,
Bis(1-methyl-2-ethylcyclopentadienyl)hafnium dichloride,
Bis(1-methyl-2-n-propylcyclopentadienyl)zirconium dichloride,
Bis(1-methyl-2-n-butyllcyclopentadienyl)hafnium dichloride,
Bis(1-methyl-3-ethylcyclopentadienyl)hafnium dichloride,
Bis(1-methyl-3-n-propylcyclopentadienyl)hafnium dichloride,
Bis(1-methyl-3-n-butylcyclopentadienyl)hafnium dichloride,
Bis(1-methyl-3-n-pentylcyclopentadienyl)hafnium dichloride,
Bis(1,2-dimethyl-4-ethylcyclopentadienyl)hafnium dichloride,
Bis(1,2-dimethyl-4-n-propylcyclopentadienyl)hafnium dichloride,
Bis(1,2-dimethyl-4-n-butylcyclopentadienyl)hafnium dichloride,
Bis(1,2-diethylcyclopentadienyl)hafnium dichloride,
Bis(1,3-diethylcyclopentadienyl)hafnium dichloride,
Bis(1,2-di-n-propylcyclopentadienyl)hafnium dichloride,
Bis(1,2-di-n-butylcyclopentadienyl)hafnium dichloride,
Bis(1-methyl-2,4-diethylcyclopentadienyl)hafnium dichloride,
Bis(1,2-diethyl-4-n-propylcyclopentadienyl)hafnium dichloride,
Bis(1,2-diethyl-4-n-butylcyclopentadienyl)hafnium dichloride,
Bis(1-methyl-3-i-propylcyclopentadienyl)hafnium dichloride,
Bis(1-ethyl-3-i-propylcyclopentadienyl)hafnium dichloride,
(1,2-dimethylcyclopentadienyl)(cyclopentadienyl)hafnium dichloride,
(1,3-dimethylcyclopentadienyl)(cyclopentadienyl)hafnium dichloride,
(1,2-dimethylcyclopentadienyl)(methylcyclopentadienyl) hafnium dichloride,
(1,2-dimethylcyclopentadienyl)(ethylcyclopentadienyl) hafnium dichloride,
(1,2-dimethylcyclopentadienyl)(1,2-di-n-butylcyclopentadienyl)hafnium dichloride,
(1,3-dimethylcyclopentadienyl)(cyclopentadienyl)hafnium dichloride,
(1,3-dimethylcyclopentadienyl)(1,2-dimethylcyclopentadienyl)hafnium dichloride, (1,3-dimethylcyclopentadienyl)(1,3-diethylcyclopentadienyl)hafnium dichloride,
Bis(indenyl)hafnium dichloride,
Bis(1-methylindenyl)hafnium dichloride,
Bis(2-methylindenyl)hafnium dichloride,
Bis(4-methylindenyl)hafnium dichloride,
Bis(4,7-dimethylindenyl)hafnium dichloride,
Bis(4,5,6,7-tetrahydroindenyl)hafnium dichloride,
Bis(4,5,6,7-tetrahydro-2-methylindenyl)hafnium dichloride,
Bis(4,5,6,7-tetrahydro-4,7-dimethylindenyl)hafnium dichloride,
(Cyclopentadienyl)(4,5,6,7-tetrahydroindenyl)hafnium dichloride,
Bis(1,2-dimethylcyclopentadienyl)hafnium dimethyl,
Bis(1,3-dimethylcyclopentadienyl)hafnium dimethyl,
Bis(1,2,3-trimethylcyclopentadienyl)hafnium dimethyl,
Bis(1,2,4-trimethylcyclopentadienyl)hafnium dimethyl,
Bis(1,2,3,4-tetramethylcyclopentadienyl)hafnium dimethyl,
Bis(1,2,3,4,5-pentamethylcyclopentadienyl)hafnium dimethyl,
Bis(1-methyl-2-ethylcyclopentadienyl)hafnium dimethyl,
Bis(1-methyl-2-n-propylcyclopentadienyl)hafnium dimethyl,
Bis(1-methyl-2-n-butyllcyclopentadienyl)hafnium dimethyl,
Bis(1-methyl-3-ethylcyclopentadienyl)hafnium dimethyl,
Bis(1-methyl-3-n-propylcyclopentadienyl)hafnium dimethyl,
Bis(1-methyl-3-n-butylcyclopentadienyl)hafnium dimethyl,
Bis(1-methyl-3-n-pentylcyclopentadienyl)hafnium dimethyl,
Bis(1,2-dimethyl-4-ethylcyclopentadienyl)hafnium dimethyl,
Bis(1,2-dimethyl-4-n-propylcyclopentadienyl)hafnium dimethyl,
Bis(1,2-dimethyl-4-n-butylcyclopentadienyl)hafnium dimethyl,
Bis(1,2-diethylcyclopentadienyl)hafnium dimethyl,
Bis(1,3-diethylcyclopentadienyl)hafnium dimethyl,
Bis(1,2-di-n-propylcyclopentadienyl)hafnium dimethyl,
Bis(1,2-di-n-butylcyclopentadienyl)hafnium dimethyl,
Bis(1-methyl-2,4-diethylcyclopentadienyl)hafnium dimethyl,
Bis(1,2-diethyl-4-n-propylcyclopentadienyl)hafnium dimethyl,
Bis(1,2-diethyl-4-n-butylcyclopentadienyl)hafnium dimethyl,
Bis(1-methyl-3-i-propylcyclopentadienyl)hafnium dimethyl,
Bis(1-ethyl-3-i-propylcyclopentadienyl)hafnium dimethyl,
(1,2-dimethylcyclopentadienyl)(cyclopentadienyl)hafnium dimethyl,
(1,3-dimethylcyclopentadienyl)(cyclopentadienyl)hafnium dimethyl,
(1,2-dimethylcyclopentadienyl)(methylcyclopentadienyl)hafnium dimethyl,
(1,2-dimethylcyclopentadienyl)(ethylcyclopentadienyl)hafnium dimethyl,
(1,2-dimethylcyclopentadienyl)(1,2-di-n-butylcyclopentadienyl)hafnium dimethyl,
(1,3-dimethylcyclopentadienyl)(cyclopentadienyl)hafnium dimethyl,
(1,3-dimethylcyclopentadienyl)(1,2-dimethylcyclopentadienyl)hafnium dimethyl,
(1,3-dimethylcyclopentadienyl)(1,3-diethylcyclopentadienyl)hafnium dimethyl,
Bis(indenyl)hafnium dimethyl,
Bis(1-methylindenyl)hafnium dimethyl,
Bis(2-methylindenyl)hafnium dimethyl,
Bis(4-methylindenyl)hafnium dimethyl,
Bis(4,7-dimethylindenyl)hafnium dimethyl,
Bis(4,5,6,7-tetrahydroindenyl)hafnium dimethyl,
Bis(4,5,6,7-tetrahydro-2-methylindenyl)hafnium dimethyl,
Bis(4,5,6,7-tetrahydro-4,7-dimethylindenyl)hafnium dimethyl, or
(Cyclopentadienyl)(4,5,6,7-tetrahydroindenyl)hafnium dimethyl.

37. The process of any of paragraphs 1 to 34 wherein the transition metal compound comprises one or more of: bis(1,2-dimethylcyclopentadienyl)zirconium dichloride, bis(1,3-dimethylcyclopentadienyl)zirconium dichloride, bis(1,2,4-trimethylcyclopentadienyl)zirconium dichloride and bis(tetramethylcyclopentadienyl)zirconium dichloride, bis(1-methyl-2-ethylcyclopentadienyl)zirconium dichloride, bis(1-methyl-3-ethylcyclopentadienyl)zirconium dichloride, bis(1-methyl-3-n-propylcyclopentadienyl)zirconium dichloride, bis(1-methyl-3-n-butylclopentadienyl)zirconium dichloride, bis(4,5,6,7-tetrahydro indenyl)zirconium dichloride, bis(indenyl)zirconium dichloride, bis(1,2-dimethylcyclopentadienyl)zirconium dimethyl, bis(1,3-dimethylcyclopentadienyl)zirconium dimethyl, bis(1,2,4-trimethylcyclopentadienyl)zirconium dimethyl, bis(tetramethylcyclopentadienyl)zirconium dimethyl, bis(1-methyl-2-ethylcyclopentadienyl)zirconium dimethyl, bis(1-methyl-3-ethylcyclopentadienyl)zirconium dimethyl, bis(1-methyl-3-n-propylcyclopentadienyl)zirconium dimethyl, bis(1-methyl-3-n-butylclopentadienyl)zirconium dimethyl, bis(4,5,6,7-tetrahydro indenyl)zirconium dichloride, or bis(indenyl)zirconium dimethyl.

38. The process of any of paragraphs 1 to 37 wherein an alkylaluminum compound is present and the alkylaluminum compound is represented by the formula: $R_3Al$, where each R is, independently, selected from the group consisting of methyl, ethyle, n-propyl, iso-propyl, iso-butyl, n-butyl, t-butyl, n-pentyl, iso-pentyl, neopentyl, n-hexyl, iso-hexyl, n-heptyl, iso-heptyl, n-octyl, iso-octyl, n-nonyl, n-decyl, n-undecyl, n-dodecyl, n-tridecyl, n-tetradecyl, n-pentadecy, n-hexadecyl, n-heptadecyl, n-octadecyl, and their iso-analogs.

39. The process of any of paragraphs 1 to 38 wherein the process is a continuous process.

40. The process of paragraph 39 wherein the process is a continuous process comprising:
 a) continuously introducing a feed stream comprising at least 10 mole % of the one or more C3 to C24 alpha-olefins into a reactor,
 b) continuously introducing the transition metal compound and the activator into the reactor,
 c) optionally continuously introducing co-activator into the reactor, and
 d) continuously withdrawing the polyalpha-olefin from the reactor.

41. The process of paragraph 40 further comprising maintaining a concentration of hydrogen in the reactor of 10,000 ppm or less by weight.

42. The process of paragraph 40 or 41 wherein the process further comprises:
 1) optionally, continuously treating the polyalpha-olefin to reduce heteroatom containing compounds to less than 600 ppm,
 2) optionally, continuously fractionating the polyalpha-olefin to separate the light and heavy fractions, where the heavy fractions have 20 or more carbons,
 3) continuously contacting the polyalpha-olefin with hydrogen and a hydrogenation catalyst, 4) continuously obtaining a polyalpha-olefin having a bromine number less than 1.8.

43. The process of any of paragraphs 1 to 42 wherein the temperature in the reactor is from −10° C. to 250° C.

44. The process of paragraph 43 wherein the temperature is from 30° C. to 220° C.

45. The process of paragraph 43 wherein the temperature is from 50° C. to 180° C.

46. The process of paragraph 43 wherein the temperature is from 70° C. to 150° C.

47. The process of any of paragraphs 1 to 46 wherein the monomers, metallocene and activator are contacted for a residence time of 5 minutes to 100 hours.

48. The process of any of paragraphs 1 to 47 wherein solvent or diluent is present.

49. The process of paragraph 48 wherein the solvent or diluent is selected from the group consisting of butanes, pentanes, hexanes, heptanes, octanes, nonanes, decanes, undecanes, dodecanes, tridecanes, tetradecanes, pentadecanes, hexadecanes, benzene, toluene, o-xylene, m-xylene, p-xylene, mixed xylenes, ethylbenzene, isopropylbenzene, and n-butylbenzene.

50. The process of any of paragraphs 1 to 49 wherein the monomers are contacted with the transition metal compound and the activator in a reactor and the reactor is a continuous stirred tank reactor.

51. The process of any of paragraphs 1 to 50 wherein catalyst residual is removed from the product by contacting with a solid sorbent.

52. The process of any of paragraphs 1 to 51 where the monomers are contacted with the transition metal compound and the activator in the solution phase.

53. The process of any of paragraphs 1 to 52 where the monomers are contacted with the transition metal compound and the activator in the slurry phase.

54. The process of any of paragraphs 1 to 53 wherein the monomers are contacted with an alkylaluminum compound prior to being introduced into the reactor 55. The process of any of paragraphs 1 to 53 where the metallocene and or activator are combined with an alkylaluminum compound prior to entering the reactor.

56. The process of paragraph 54 where the alkylaluminum compound is selected from tri-isobutylaluminum, tri-n-octylaluminum, tri-n-hexylaluminum, and tri-n-dodecylaluminum.

57. The process of paragraph 54 where an alkylaluminum compound is present and the compound is selected from tri-isobutylaluminum, tri-n-octylaluminum, tri-n-hexylaluminum, and tri-n-dodecylaluminum.

58. The process of any of paragraphs 1 to 57 where in the polyalpha-olefin is contacted with hydrogen and a hydrogenation catalyst selected from the group consisting of supported Group 7, 8, 9, and 10 metals.

59. The process of any of paragraphs 1 to 57 wherein the polyalpha-olefin is contacted with hydrogen and a hydrogenation catalyst selected from the group consisting of one or more of Ni, Pd, Pt, Co, Rh, Fe, Ru, Os, Cr, Mo, and W, supported on silica, alumina, clay, titania, zirconia, or mixed metal oxide supports.

60. The process of paragraph 59 wherein where the hydrogenation catalyst is nickel supported on keisleghur, silica, alumina, clay or silica-alumina.

61. The process of any of paragraphs 1 to 60 wherein the polyalpha-olefin is contacted with hydrogen and a hydrogenation catalyst at a temperature from 25 to 350° C.

62. The process of any of paragraphs 1 to 61 wherein the product produced has 60 wt % or less C10 dimer.

63. The process of any of paragraphs 1 to 62 wherein the product produced has 40 wt % or less C10 dimer.

64. The process of any of paragraphs 1 to 63 wherein the process further comprises:

1) catalyst residual is removed from the polyalpha-olefin by contacting the polyalpha-olefin with a solid sorbent, 2) optionally, treating the polyalpha-olefin to reduce heteroatom containing compounds to less than 600 ppm, 3) optionally, fractionating the polyalpha-olefin to separate the light and heavy fractions, where the heavy fractions have 20 or more carbons, 4) contacting the polyalpha-olefin with hydrogen and a hydrogenation catalyst, and 5) obtaining a polyalpha-olefin having a bromine number less than 1.8.

EXAMPLES

Fluid properties were measured by following standard methods, except when described otherwise: kinematic viscosity at 40 and 100° C. in cSt by ASTM 445 method; pour point by ASTM D97 method; and viscosity index (VI) according to ASTM D2270.

The following examples are for purposes of illustration only and are non-limiting examples.

The 1-decene used for all of the experiments was purified by mixing 1 liter of untreated raw material with 20 grams of activated 13X molecular sieve, (which was activated by calcining at 200° C. for at least four hours under a stream of purging dry nitrogen gas), and 10 grams of Oxi-Clear catalyst (purchased from Altech Associates, Inc of Deerfield, Ill. 60115) for at least two days inside a glove box under a dry, inert atmosphere of nitrogen. The molecular sieve and de-oxygenation catalyst were then removed by filtration in the glove box to provide purified 1-decene. Alternatively, the feeds were purified by passing through a bed of activated 13X molecular sieve alone under nitrogen atmosphere.

The Data in Table 3 were generated as follows. The polymerization/oligomerization reaction was generally carried out under nitrogen ($N_2$) inert atmosphere or argon inert atmosphere. In a small scale screening experiment, 2.96 grams of purified 1-decene was added into a small stainless steel reactor fitted with glass liner with a total reactor volume of 5.5 ml, an agitator and a temperature controller, followed by addition of 2 micromole of tri-n-octylcluminium and 0.04 micromole of N,N-dimethylanilinium tetrakis(perfluorophenyl)borate solution of 1 micromole/liter. The reactor was then heated to the desired reaction temperature and the desired amount of metallocene catalyst in toluene (0.04 micromole of metallocene catalyst solution of 1 micromole/liter), was added to initiate the polymerization reaction. After 3 hours, the reaction was quenched by addition of carbon dioxide ($CO_2$) gas of equal moles as the metallocene catalyst. The polymerization/oligomerization product was isolated by stripping the reactor contents, from about room temperature to 50° C., under high vacuum for at least 2 hours to remove solvent, unreacted starting material and dimer, i.e., any component having less than thirty carbon atoms. The product properties, including molecular weight and Mw/Mn, were analyzed by gel permeation chromatography using tetrahydrofuran as the solvent and polystyrene as the calibration standard. The residual fluid viscosity was calculated by a correlation equation, which correlated the Mw by GPC to fluid viscosity as described in Table 3.

Experiments PD-1 to PD-103 In the experiments below in Table 3, 40 mmol of catalyst, 40 nmol of activator (N,N-dimethylanilinium tetrakis(perfluorophenyl)borate), 2 micromol of TNOAl (tri-n-octylaluminum), 4.00 mL of 1-decene, and 1.00 mL of toluene were used. Each experiment was run for 90 minutes.

TABLE 3

1-Decene Batch Oligomerizations

| Ex # | Catalyst[a] | Temp (° C.) | H$_2$ pressure (psia)[b] | C20+ Yield (g) | Conversion (%) to C20+ | GPC Mw | GPC Mn | PDI Mw/Mn | Viscosity[c] at 100° C. (cS) |
|---|---|---|---|---|---|---|---|---|---|
| PD-1 | 1 | 80 | 0 | 0.3646 | 12.3 | 2,024 | 1,757 | 1.2 | 5.9 |
| PD-2 | 1 | 100 | 0 | 0.5614 | 18.9 | 1,503 | 1,394 | 1.1 | 4.1 |
| PD-3 | 1 | 120 | 0 | 0.5624 | 19.0 | 1,257 | 1,194 | 1.1 | 3.3 |
| PD-4 | 1 | 80 | 0 | 0.3751 | 12.7 | 2,174 | 1,873 | 1.2 | 6.4 |
| PD-5 | 1 | 100 | 0 | 0.6060 | 20.4 | 1,457 | 1,359 | 1.1 | 3.9 |
| PD-6 | 1 | 120 | 0 | 0.8420 | 28.4 | 1,302 | 1,224 | 1.1 | 3.4 |
| PD-7 | 1 | 100 | 44.7 | 1.9434 | 65.6 | 1,267 | 1,203 | 1.1 | 3.3 |
| PD-8 | 1 | 120 | 44.7 | 2.0314 | 68.5 | — | — | — | — |
| PD-9 | 1 | 120 | 54.7 | 2.0621 | 69.6 | — | — | — | — |
| PD-10 | 1 | 100 | 54.7 | 2.1813 | 73.6 | 1,295 | 1,231 | 1.1 | 3.4 |
| PD-11 | 2 | 100 | 0 | 0.1413 | 4.8 | 3,258 | 2,569 | 1.3 | 10.1 |
| PD-12 | 2 | 120 | 0 | 0.1984 | 6.7 | 1,777 | 1,593 | 1.1 | 5.0 |
| PD-13 | 2 | 100 | 0 | 0.1914 | 6.5 | 3,462 | 2,695 | 1.3 | 10.8 |
| PD-14 | 2 | 120 | 0 | 0.2129 | 7.2 | 1,743 | 1,568 | 1.1 | 4.9 |
| PD-15 | 2 | 120 | 44.7 | 0.9971 | 33.6 | 1,620 | 1,489 | 1.1 | 4.5 |
| PD-16 | 2 | 120 | 54.7 | 0.9083 | 30.6 | 1,547 | 1,432 | 1.1 | 4.2 |
| PD-17 | 3 | 100 | 0 | 0.1225 | 4.1 | 1,511 | 1,402 | 1.1 | 4.1 |
| PD-18 | 3 | 120 | 0 | 0.2995 | 10.1 | 1,224 | 1,170 | 1.0 | 3.1 |
| PD-19 | 3 | 100 | 0 | 0.3620 | 12.2 | 1,480 | 1,383 | 1.1 | 4.0 |
| PD-20 | 3 | 120 | 0 | 0.1434 | 4.8 | 1,231 | 1,163 | 1.1 | 3.2 |
| PD-21 | 3 | 100 | 54.7 | 1.2840 | 43.3 | 1,345 | 1,278 | 1.1 | 3.6 |
| PD-22 | 3 | 100 | 44.7 | 1.8752 | 63.3 | 1,372 | 1,303 | 1.1 | 3.6 |
| PD-23 | 3 | 100 | 54.7 | 1.5646 | 52.8 | 1,357 | 1,284 | 1.1 | 3.6 |
| PD-24 | 3 | 120 | 44.7 | 0.5144 | 17.4 | 1,175 | 1,125 | 1.0 | 3.0 |
| PD-25 | 4 | 100 | 0 | 0.0179 | 0.6 | 5,305 | 3,804 | 1.4 | 103.4 |
| PD-26 | 4 | 120 | 0 | 0.0565 | 1.9 | 2,437 | 2,037 | 1.2 | 7.3 |
| PD-27 | 4 | 100 | 0 | 0.0221 | 0.7 | 5,729 | 3,995 | 1.4 | 117.1 |
| PD-28 | 4 | 120 | 0 | 0.0462 | 1.6 | 2,495 | 2,059 | 1.2 | 7.5 |
| PD-29 | 4 | 100 | 34.7 | 0.6167 | 20.8 | 4,274 | 3,190 | 1.3 | 73.1 |
| PD-30 | 4 | 100 | 54.7 | 0.0643 | 2.2 | 3,614 | 2,759 | 1.3 | 11.3 |
| PD-31 | 4 | 120 | 34.7 | 0.0992 | 3.3 | 2,114 | 1,820 | 1.2 | 6.2 |
| PD-32 | 4 | 120 | 44.7 | 0.0935 | 3.2 | 2,585 | 2,140 | 1.2 | 7.8 |
| PD-33 | 4 | 100 | 34.7 | 0.0630 | 2.1 | 3,922 | 2,932 | 1.3 | 12.3 |
| PD-34 | 4 | 100 | 54.7 | 0.0653 | 2.2 | 3,645 | 2,785 | 1.3 | 11.4 |
| PD-35 | 5 | 80 | 0 | 0.5352 | 18.1 | 2,438 | 2,034 | 1.2 | 7.3 |
| PD-36 | 5 | 100 | 0 | 0.8795 | 29.7 | 1,609 | 1,480 | 1.1 | 4.5 |
| PD-37 | 5 | 120 | 0 | 0.5211 | 17.6 | 1,308 | 1,232 | 1.1 | 3.4 |
| PD-38 | 5 | 80 | 0 | 0.4908 | 16.6 | 2,642 | 2,184 | 1.2 | 8.0 |
| PD-39 | 5 | 100 | 0 | 0.8901 | 30.0 | 1,583 | 1,448 | 1.1 | 4.4 |
| PD-40 | 5 | 120 | 0 | 0.7976 | 26.9 | 1,354 | 1,281 | 1.1 | 3.6 |
| PD-41 | 5 | 100 | 54.7 | 1.3083 | 44.1 | 1,401 | 1,327 | 1.1 | 3.7 |
| PD-42 | 5 | 120 | 34.7 | 1.4062 | 47.4 | 1,211 | 1,145 | 1.1 | 3.1 |
| PD-43 | 5 | 120 | 44.7 | 1.3556 | 45.7 | 1,212 | 1,159 | 1.0 | 3.1 |
| PD-44 | 5 | 100 | 34.7 | 1.3702 | 46.2 | 1,433 | 1,343 | 1.1 | 3.9 |
| PD-45 | 5 | 100 | 54.7 | 1.5293 | 51.6 | 1,430 | 1,342 | 1.1 | 3.8 |
| PD-46 | 6 | 100 | 54.7 | 2.2348 | 75.4 | — | — | — | — |
| PD-47 | 6 | 120 | 54.7 | 1.8615 | 62.8 | — | — | — | — |
| PD-48 | 7 | 100 | 54.7 | 1.4172 | 47.8 | — | — | — | — |
| PD-49 | 7 | 100 | 54.7 | 1.2324 | 41.6 | 1,551 | 1,446 | 1.1 | 4.3 |
| PD-50 | 7 | 100 | 54.7 | 1.2878 | 43.4 | — | — | — | — |
| PD-51 | 7 | 120 | 54.7 | 1.0333 | 34.9 | — | — | — | — |
| PD-52 | 8 | 100 | 44.7 | 0.3415 | 11.5 | 1,137 | 1,061 | 1.1 | 2.8 |
| PD-53 | 8 | 100 | 54.7 | 0.3734 | 12.6 | 1,119 | 1,051 | 1.1 | 2.8 |
| PD-54 | 8 | 120 | 44.7 | 0.2420 | 8.2 | 1,239 | 1,112 | 1.1 | 3.2 |
| PD-55 | 8 | 120 | 54.7 | 0.2318 | 7.8 | 1,229 | 1,094 | 1.1 | 3.2 |
| PD-56 | 8 | 100 | 54.7 | 0.3621 | 12.2 | 1,135 | 1,064 | 1.1 | 2.8 |
| PD-57 | 8 | 100 | 44.7 | 0.2421 | 8.2 | 1,189 | 1,074 | 1.1 | 3.0 |
| PD-58 | 8 | 120 | 44.7 | 0.1473 | 5.0 | 1,289 | 1,127 | 1.1 | 3.4 |
| PD-59 | 9 | 100 | 54.7 | 1.6228 | 54.8 | — | — | — | — |
| PD-60 | 9 | 120 | 54.7 | 0.3539 | 11.9 | — | — | — | — |
| PD-61 | 9 | 120 | 54.7 | 0.6742 | 22.7 | — | — | — | — |
| PD-62 | 10 | 100 | 44.7 | 1.4583 | 49.2 | 1,194 | 1,105 | 1.1 | 3.0 |
| PD-63 | 10 | 100 | 44.7 | 1.6585 | 56.0 | 1,234 | 1,142 | 1.1 | 3.2 |
| PD-64 | 10 | 120 | 44.7 | 1.4781 | 49.9 | 1,110 | 1,048 | 1.1 | 2.8 |
| PD-65 | 10 | 120 | 44.7 | 0.2079 | 7.0 | 1,141 | 1,058 | 1.1 | 2.9 |
| PD-66 | 10 | 120 | 54.7 | 1.3328 | 45.0 | 1,076 | 1,017 | 1.1 | 2.6 |
| PD-67 | 10 | 100 | 44.7 | 1.4456 | 48.8 | 1,212 | 1,123 | 1.1 | 3.1 |
| PD-68 | 10 | 100 | 54.7 | 1.7571 | 59.3 | 1,185 | 1,101 | 1.1 | 3.0 |
| PD-69 | 10 | 100 | 44.7 | 0.9474 | 32.0 | 1,097 | 1,040 | 1.1 | 2.7 |
| PD-70 | 10 | 120 | 44.7 | 0.8823 | 29.8 | 1,066 | 1,010 | 1.1 | 2.6 |
| PD-71 | 10 | 120 | 54.7 | 0.0495 | 1.7 | 1,225 | 1,128 | 1.1 | 3.1 |
| PD-72 | 11 | 100 | 0 | 0.7898 | 26.6 | 1,318 | 1,193 | 1.1 | 3.5 |
| PD-73 | 11 | 100 | 44.7 | 1.2999 | 43.9 | 1,271 | 1,156 | 1.1 | 3.3 |
| PD-74 | 11 | 100 | 54.7 | 1.7127 | 57.8 | 1,276 | 1,160 | 1.1 | 3.3 |

TABLE 3-continued

1-Decene Batch Oligomerizations

| Ex # | Catalyst[a] | Temp (° C.) | H$_2$ pressure (psia)[b] | C20+ Yield (g) | Conversion (%) to C20+ | GPC Mw | GPC Mn | PDI Mw/Mn | Viscosity[c] at 100° C. (cS) |
|---|---|---|---|---|---|---|---|---|---|
| PD-75 | 11 | 120 | 0 | 0.6013 | 20.3 | 1,129 | 1,042 | 1.1 | 2.8 |
| PD-76 | 11 | 120 | 44.7 | 1.9060 | 64.3 | 1,135 | 1,056 | 1.1 | 2.8 |
| PD-77 | 11 | 120 | 54.7 | 1.8636 | 62.9 | 1,117 | 1,034 | 1.1 | 2.8 |
| PD-78 | 11 | 100 | 0 | 0.8842 | 29.8 | 1,330 | 1,201 | 1.1 | 3.5 |
| PD-79 | 11 | 100 | 44.7 | 1.6737 | 56.5 | 1,290 | 1,169 | 1.1 | 3.4 |
| PD-80 | 11 | 100 | 54.7 | 1.9463 | 65.7 | 1,296 | 1,177 | 1.1 | 3.4 |
| PD-81 | 11 | 120 | 0 | 0.6646 | 22.4 | 1,139 | 1,059 | 1.1 | 2.9 |
| PD-82 | 11 | 120 | 44.7 | 1.9115 | 64.5 | 1,152 | 1,058 | 1.1 | 2.9 |
| PD-83 | 11 | 120 | 54.7 | 1.8410 | 62.1 | 1,131 | 1,045 | 1.1 | 2.8 |
| PD-84 | 11 | 100 | 0 | 0.6138 | 20.7 | 1,349 | 1,216 | 1.1 | 3.6 |
| PD-85 | 11 | 100 | 44.7 | 1.4443 | 48.7 | 1,296 | 1,172 | 1.1 | 3.4 |
| PD-86 | 11 | 100 | 54.7 | 1.5584 | 52.6 | 1,310 | 1,188 | 1.1 | 3.4 |
| PD-87 | 11 | 120 | 0 | 0.7822 | 26.4 | 1,157 | 1,068 | 1.1 | 2.9 |
| PD-88 | 11 | 120 | 44.7 | 1.8857 | 63.6 | 1,140 | 1,028 | 1.1 | 2.9 |
| PD-89 | 12 | 100 | 0 | 1.0660 | 36.0 | 1,485 | 1,311 | 1.1 | 4.0 |
| PD-90 | 12 | 100 | 44.7 | 1.2387 | 41.8 | 1,411 | 1,256 | 1.1 | 3.8 |
| PD-91 | 12 | 100 | 54.7 | 1.1749 | 39.6 | 1,445 | 1,285 | 1.1 | 3.9 |
| PD-92 | 12 | 120 | 0 | 0.6507 | 22.0 | 1,216 | 1,109 | 1.1 | 3.1 |
| PD-93 | 12 | 120 | 44.7 | 1.4787 | 49.9 | 1,202 | 1,104 | 1.1 | 3.1 |
| PD-94 | 12 | 120 | 54.7 | 1.8587 | 62.7 | 1,167 | 1,075 | 1.1 | 2.9 |
| PD-95 | 12 | 100 | 0 | 1.1199 | 37.8 | 1,476 | 1,304 | 1.1 | 4.0 |
| PD-96 | 12 | 100 | 54.7 | 1.1552 | 39.0 | 1,422 | 1,267 | 1.1 | 3.8 |
| PD-97 | 12 | 120 | 0 | 0.4124 | 13.9 | 1,210 | 1,110 | 1.1 | 3.1 |
| PD-98 | 12 | 100 | 0 | 1.0271 | 34.7 | 1,503 | 1,323 | 1.1 | 4.1 |
| PD-99 | 12 | 100 | 44.7 | 1.4780 | 49.9 | 1,420 | 1,259 | 1.1 | 3.8 |
| PD-100 | 12 | 100 | 54.7 | 1.2133 | 40.9 | 1,416 | 1,263 | 1.1 | 3.8 |
| PD-101 | 12 | 120 | 0 | 0.8040 | 27.1 | 1,206 | 1,104 | 1.1 | 3.1 |
| PD-102 | 12 | 120 | 44.7 | 0.5413 | 18.3 | 1,197 | 1,102 | 1.1 | 3.1 |
| PD-103 | 12 | 120 | 54.7 | 1.0399 | 35.1 | 1,161 | 1,067 | 1.1 | 2.9 |

[a]1 is (1,3-Me,n-Bu-Cp)$_2$ZrMe$_2$, 2 is (n-Pr-Cp)$_2$HfMe$_2$, 3 is (Me$_4$Cp)$_2$HfMe$_2$, 4 is Cp$_2$HfMe$_2$, 5 is (n-Pr-Cp)$_2$ZrMe$_2$, 6 is (Me$_4$Cp)$_2$ZrMe$_2$, 7 is (MeCp)$_2$ZrMe$_2$, 8 is (Me$_5$Cp)$_2$ZrMe$_2$, 9 is (n-Pr-Cp)(Me$_4$-Cp)ZrMe$_2$, 10 is (1,3-diMe-Cp)$_2$ZrMe$_2$, 11 js (EtCp)$_2$ZrMe$_2$, 12 is (n-BuCp)$_2$ZrMe$_2$.
[b]Pressure is given for the mixture of 95% N$_2$/5% hydrogen.
[c]Viscosity of fluid at 100° C. was estimated based on a correlation developed between GPC Mw and measured viscosity. For Mw < 4000, viscosity at 100° C. in cS = 0.0034(Mw) − 1.0174. For Mw > 4000, viscosity at 100° C. in cS = 0.000002(Mw)$^2$ + 0.0102(Mw) − 7.0186.

Examples 1A to 8A. In a 600 ml autoclave, a solution containing 90 gram of purified 1-decene and 4 gram of tri-n-octylaluminum (TNOAL) solution containing 20 mg TNOAL per gram of solution in toluene solvent were added. The reactor was pressurized with hydrogen to appropriate pressure indicated in Table 1A. The mixture was heated to reaction temperature with slow agitation. Under this condition, a catalyst solution, containing 20 gram toluene, 0.5 gram TNOAL solution and 1.60 mg catalyst A (1-Me-3-n-BuCp)$_2$ZrMe$_2$) and 3.84 mg of activator (dimethylaniliniumperfluorotetraphenylborate), was added slowly over a period of 15 minutes to 30 minutes while maintaining reaction temperature within 10° C. of the set temperature. The reaction mixture was stirred for 4 hours. The reactor was cooled down to room temperature and then 10 grams of activated alumina were added to the reaction mixture to deactivate the catalyst and to absorb the catalyst. The alumina was then filtered to remove the solid and any catalyst residual. The residual organic layer was analyzed by Gas Chromatography to obtain conversion and product selectivity. The organic layer was further fractionated to remove solvent, unreacted olefins, and light fraction, usually C20 olefins and smaller, to give a residual fraction. If indicated, the residual fraction was further hydrogenated with hydrogen with 2 wt % of a 50% Nickle on Kieselguhr catalyst at 200° C. and 800 psi hydrogen pressure for 4 hours. The viscometric properties of the hydrogenated product were similar to the unhydrogenated products. For convenience, the viscometric properties of this unhydrogenated residual fraction were reported in Table 1A. The catalyst productivity was calculated as the grams of total product made from feed olefins per gram of metallocene metal.

In comparison, Table 2A shows the examples of U.S. Pat. No. 6,548,724 using metallocene and NCA activator to produce fluids. The catalyst productivities were calculated on the same basis as Example 1 to 9. As the data show, Examples 1 to 8 have high catalyst productivity in grams of product per gram of metallocene. The highest catalyst productivity Table 2A appears to be 41.6 kg/g metallocene.

Examples 1 through 8 were conducted generally as described above, with additional experimental details provided in Table 1 below. Table 2 presents selected data taken from Examples 14 to 18 of U.S. Pat. No. 6,548,724.

TABLE 1A

| | Example | | | | | | | |
|---|---|---|---|---|---|---|---|---|
| | 1 | 2 | 3 | 4 | 5 | 6 | 7 | 8 |
| Catalyst | A | A | A | A | A | B | B | B |
| Rxn Temp, ° C. | 120 | 100 | 121 | 120 | 120 | 120 | 100 | 60 |
| H2 pressure psi | 0 | 10 | 10 | 30 | 60 | 30 | 30 | 30 |

TABLE 1A-continued

| | Example | | | | | | | |
|---|---|---|---|---|---|---|---|---|
| | 1 | 2 | 3 | 4 | 5 | 6 | 7 | 8 |
| Decene*, g | 90 | 90 | 90 | 90 | 90 | 90 | 90 | 90 |
| Catalyst*, mg | 1.6 | 1.6 | 1.6 | 1.6 | 1.6 | 1.6 | 1.6 | 1.6 |
| Activator*, mg | 3.84 | 3.84 | 3.84 | 3.84 | 3.84 | 3.84 | 3.84 | 3.84 |
| TNOAL, mg | 90 | 90 | 90 | 90 | 90 | | | |
| Wt % Conversion of feed olefins | 61.5 | 82.9 | 89.1 | 89 | 85.4 | 78.8 | 75.7 | 83.6 |
| Wt % Selectivity to C20 | 49.3 | 32.7 | 53.3 | 53.7 | 55.2 | 79.8 | 64.4 | 16.7 |
| Product Property | | | | | | | | |
| KV100° C., cSt | 4.65 | 5.02 | 4.42 | 4.38 | 4.39 | 3.94 | 4.29 | 11.06 |
| KV40° C., cSt | 20.3 | 22.01 | 18.86 | 18.87 | 18.68 | 16.25 | 18.19 | 65.46 |
| Viscosity Index | 153 | 164 | 152 | 147 | 151 | 143 | 149 | 162 |
| Productivity | | | | | | | | |
| g product/g metallocene | 34,594 | 46,623 | 50,105 | 50,063 | 48,038 | 44,332 | 42,638 | 47,000 |

A = (1-Me-3-n-BuCp)$_2$ZrMe$_2$,
B = (Me$_4$Cp)$_2$ZrCl$_2$,
Activator = dimethylaniliniumperfluorotetraphenylborate,
TNOAL = tri-n-octyl-aluminum,
*= Solution weight, grams in reaction flask

TABLE 2A

| | U.S. Pat. No. 6,548,724 example no | | | | |
|---|---|---|---|---|---|
| | 14 | 15 | 16 | 17 | 18 |
| Catalyst | Cp$_2$ZrMe$_2$ | Cp$_2$ZrMe$_2$ | Cp$_2$ZrMe$_2$ | (iPrCp)$_2$ZrCl$_2$ | (iPrCp)$_2$ZrCl$_2$ |
| Mole wt, g/mole | 251.5 | 251.5 | 251.5 | 376.1 | 376.1 |
| Catalyst wt., mg | 8.8025 | 8.8025 | 8.8025 | 13.1635 | 13.1635 |
| Activator Z, mg | 11.1 | 28.035 | 28.035 | 28.035 | 28.035 |
| TIBA, gram | 0.1572 | 0.1572 | 0.1572 | 0.1572 | 0.1572 |
| H2 pressure, psi | 0 | 0 | 50 | 0 | 50 |
| 1-decene feed, gram | 882 | 1096 | 1049 | 1072 | 1047 |
| Temp. ° C. | 100 | 110 | 110 | 110 | 110 |
| % dimer selectivity | 24.9 | 35.7 | 40.7 | 35.9 | 41.6 |
| 100° C. Kv, cSt | 11.4 | 6.7 | 6.7 | 5.4 | 5.3 |
| Pour point, ° C. | −57 | −59 | −59 | −66 | −69 |
| Viscosity Index | 160 | | | | |
| Catalyst Productivity | | | | | |
| g product/g catalyst metallocene | 12,178 | 17,870 | 41,636 | 18,437 | 40,392 |

TIBA = tri-isobutylaluminum,
Activator Z = N,Ndimethylanilinium tetra(perfluorophenyl)borate,

Example 9

Batch Runs—In these runs, a catalyst solution containing 10 mg TNOAL, 1.6 mg catalyst 1 and 3.84 mg of dimethylaniliniumperfluorotetraphenylborate in 20 gram toluene solution was added to an autoclave containing 90 gram of 1-decene and 80 mg of TNOAL heated to reaction temperature under hydrogen pressure. The reaction was then discontinued after 4 hours by injecting 10 gram of solid alumina. The product was isolated by filtration to remove any solid residual, distilled at 100° C. under vacuum to remove toluene or unreacted olefins followed by distillation at 160° C./<1 milli-torr vacuum to remove light ends. The reaction conditions and residual olefinic polymer properties and compositions are summarized in Table 4. In all of the following experiments the molar ratio of TNOAl scavenger to catalyst was 60, and the molar ratio of activator to catalyst was 1.0. The residual fraction of some runs was further hydrogenated with hydrogen with 2 wt % of a 50% Nickle on Kieselguhr catalyst at 200° C. and 800 psi hydrogen pressure for 4 hours.

TABLE 4

| | 1-Decene Oligomerization in Batch Reactor | | | | | |
|---|---|---|---|---|---|---|
| | Run | | | | | |
| | A | B | C | D | E | F |
| Catalyst | 1 | 1 | 1 | 1 | 1 | 1 |
| Temp (° C.) | 120 | 80 | 100 | 121 | 120 | 120 |
| H$_2$ pressure (psi) | 0 | 10 | 10 | 10 | 30 | 60 |
| Wt % Conversion of starting olefin | 61.5 | 72.4 | 82.9 | 89.1 | 89 | 85.4 |

TABLE 4-continued

1-Decene Oligomerization in Batch Reactor

| | Run | | | | | |
|---|---|---|---|---|---|---|
| | A | B | C | D | E | F |
| Wt % Lube selectivity | 50.7 | 92.3 | 63.3 | 46.7 | 46.3 | 44.8 |
| Viscosity at 100° C., cS | 4.65 | 10.11 | 5.02 | 4.42 | 4.38 | 4.39 |
| Viscosity at 40° C., cS | 20.3 | 56.67 | 22.01 | 18.86 | 18.87 | 18.68 |
| VI | 140 | 156 | 130 | 139 | 135 | 139 |
| Pour point, ° C. | <−60 | nm | nm | nm | <−61 | <−61 |
| g lube/g Zr | 17,539 | 37,589 | 29,505 | 23,410 | 23,179 | 21,521 |
| g total product/g Zr | 34,594 | 40,725 | 46,623 | 50,105 | 50,063 | 48,038 |
| % 1-decene hydrogenated | 0.0 | | | 0.8 | 3.1 | 6.4 |
| Olefin Content by H-NMR analysis | | | | | | |
| Total olefins/1000 C | 27.5 | | | | 27.4 | 26.3 |
| Mole % olefin type distribution | | | | | | |
| 1,2-disubstituted olefins | 4.3 | | | | 4.0 | 3.5 |
| Tri-substituted olefins | 19.2 | | | | 24.0 | 26.7 |
| Vinylidene olefins | 76.5 | | | | 72.0 | 69.8 | nm = not measured

Example 10

Continuous Runs

This set of experiments was carried out in a continuous reactor process. 1-decene and toluene used in the runs were sparged with nitrogen and then purified through a 5-Angstrom molecular sieve. The metallocene catalyst used was Catalyst 1, preactivated with N,N-dimethylanilinium tetra(pentafluorophenyl)borate with equal molar amounts of metallocene and activator in toluene solution. The experiments were conducted in a series dual-reactor continuous process. Both of the reactors were 1-liter autoclave reactors. All feeds were introduced into the first reactor and products were continuously withdrawn from the second reactor. Both of the reactors were controlled at the same reaction temperature. The product isolation and hydrogenation were similar to that of Example 9. The polymerization conditions and product properties after hydrogenation are summarized in Table 5.

TABLE 5

1-Decene Oligomerization in Continuous Process

| | Metallocene | | | |
|---|---|---|---|---|
| | 1 | 1 | 1 | 1 |
| Temp (° C.) | 100 | 100 | 120 | 120 |
| 1-decene, mL/min | 40 | 40 | 40 | 40 |
| H2, scc/min | 5 | 20 | 5 | 20 |
| Catalyst, mol/min | $2.48 \times 10^{-6}$ | $2.48 \times 10^{-6}$ | $2.48 \times 10^{-6}$ | $2.48 \times 10^{-6}$ |
| Wt % Olefin Conversion | 59.8 | 76.4 | 73.2 | 83.8 |
| Wt % Lube selectivity (C30+) | 87.2 | 81.7 | 59.2 | 52.3 |
| Wt % C20 selectivity | 12.8 | 18.3 | 40.8 | 47.7 |
| Viscosity at 100° C., cS | 8.05 | 6.53 | 4.58 | 4.36 |
| Viscosity at 40° C., cS | 43.43 | 32.50 | 20.00 | 18.54 |
| VI | 161 | 160 | 151 | 150 |
| Pour point, ° C. | −60.9 | −60.3 | −51 | −45 |
| g lube/g metallocene | 15,924 | 19,049 | 13,220 | 13,378 |

Catalyst 1 is (1,3-Me,n-Bu-Cp)$_2$ZrMe$_2$

Example 11

Experimental procedures: 100 grams of pure 1-butene or propylene were charged into a 600-ml autoclave at room temperature, followed by the proper amount of hydrogen if hydrogen was added (see Table 6 below). The reactor was then heated to reaction temperature. At reaction temperature, catalyst solution containing all catalyst components were added in three stages to reactors, so that reaction temperature was maintained as constant as possible. The reaction was quenched after 16 hours and lube product (C20 and above) was isolated in similar manner as in Example 9 above. The results and certain reaction conditions of propylene and 1-butene oligomerizations are summarized in following Table 6. The product fluids have low viscosities and were produced with productivity of more than 43,000 g total product/g of metallocene catalyst. Furthermore, the lube product produced from propylene or 1-butene has good VI and low pour points, suitable for high performance liquids.

| | Example No. | |
|---|---|---|
| | 11A | 11B |
| Reaction Temperature, ° C. | 110 | 80 |
| hydrogen pressure, psi | 30 | 30 |
| Feed Olefins | propylene | 1-butene |
| Wt, grams | 100 | 100 |
| Catalyst solution in addition funnel | | |
| Toluene, grams | 40 | 20 |
| TIBA, mg | 26 | 12.7 |
| Metallocene, mg | 1.47 | 1.824 |

| | Example No. | |
|---|---|---|
| | 11A | 11B |
| Activator, mg | 3.205 | 3.2048 |
| Wt % Conversion by GC | 67.52 | 87.52 |
| Product Selectivity | | |
| light ends (<C24), wt % | 78.4 | 54.12565 |
| lube, (C25 and above)wt % | 21.6 | 45.87435 |
| Lube Properties | | |
| V 100° C., cS | 10.02 | 9.68 |
| V 40° C., cS | 102.77 | 94.39 |
| VI | 70 | 75 |
| Pour Point, ° C. | −30 | −32 |
| Bromine Number | | 25.6 |
| GPC | | |
| Mw | 1000 | 782 |
| Mn | 868 | 710 |
| Mw/Mn | 1.152 | 1.101 |
| g total pdt/g metallocene | 45,932 | 47,982 |

TIBA is triisobutylaluminum,
Activator = N,N-dimethylanilinium tetra(perfluorophenyl)borate,
Catalyst A = bis(1-methyl-3-n-butylcyclopentadienyl)zirconium dimethyl All documents described herein are incorporated by reference herein, including any priority documents and/or testing procedures, except to the extent they are inconsistent with this specification. As is apparent from the foregoing general description and the specific embodiments, while forms of the invention have been illustrated and described, various modifications can be made without departing from the spirit and scope of the invention. Accordingly, it is not intended that the invention be limited thereby.

The invention claimed is:

1. A process to produce a polyalpha-olefin comprising:
1) contacting one or more alpha-olefin monomers having 3 to 24 carbon atoms with an unbridged, mono-substituted bis cyclopentadienyl transition metal compound, wherein the substitution is a non-isoolefin substitution on both cyclopentadienyl rings, a non-coordinating anion activator, and an alkyl-aluminum compound, where the molar ratio of transition metal compound to activator is 2:1 to 0.5:1, the molar ratio of alkyl aluminum compound to transition metal compound is 2:1 to 500:1, and the milligram amount of transition metal compound per gram of alpha-olefin monomer is in the range of 0.001 to 1, under polymerization conditions wherein:
i) hydrogen is present at a partial pressure of 0.1 psi to less than 50 psi, based upon the total pressure of the reactor;
ii) wherein the alpha-olefin monomer(s) having 3 to 24 carbon atoms are present at 10 volume % or more based upon the total volume of the catalyst/activator/alkylaluminum compound solutions, monomers, and any diluents or solvents present in the reaction;
iii) the residence time of the reaction is at least 5 minutes;
iv) the productivity of the process is at least 43,000 grams of total product per gram of transition metal compound;
v) the process is continuous or semi-continuous, and
vi) ethylene is not present at more than 30 volume % of the monomers entering the reaction zone; and
2) obtaining a polyalpha-olefin (PAO) wherein the PAO has a Mw/Mn of at least 1 and no greater than 1.4, optionally hydrogenating the PAO, wherein the PAO comprises at least 50 mole % of a C3 to C24 alpha-olefin monomer, and wherein the PAO has a kinematic viscosity at 100° C. of 20 cSt or less.

2. The process of claim 1 wherein the transition metal compound is represented by the formula:

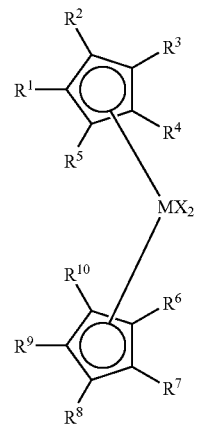

where M is a Group 4 metal;
each X is a hydrogen, halogen, hydride radicals, hydrocarbyl radicals, substituted hydrocarbyl radicals, halocarbyl radicals, substituted halocarbyl radicals, silylcarbyl radicals, substituted silylcarbyl radicals, germylcarbyl radicals, or substituted germylcarbyl radicals, or both X are joined and bound to the metal atom to form a metallacycle ring containing from about 3 to about 20 carbon atoms, or both together can be an olefin, diolefin or aryne ligand; and
$R^1$ to $R^{10}$ are independently, a radical group which is a hydrogen, a heteroatom, hydrocarbyl, substituted hydrocarbyl, halocarbyl, substituted halocarbyl, silylcarbyl or germylcarbyl, provided that: one of $R^1$ to $R^5$ is not hydrogen or an isoolefin and one of $R^6$ to $R^{10}$ is not hydrogen or an isoolefin.

3. The process of claim 1 wherein the PAO has a pour point of 0° C. or less.

4. The process of claim 1 wherein the PAO has a pour point of −40° C. or less and a kinematic viscosity at 100° C. of 15 cSt or less.

5. The process of claim 1 wherein the PAO has a pour point of −55° C. or less and a kinematic viscosity at 100° C. of 10 cSt or less.

6. The process of claim 1 wherein the polyalpha-olefin is polydecene having an Mw/Mn of between 1 and 1.4.

7. The process of claim 1 wherein the polyalpha-olefin has a Bromine number of 1.8 or more.

8. The process of claim 1 wherein the polyalpha-olefin has a Kinematic viscosity at 100° C. of from 1.5 to 15 cSt.

9. The process of claim 1 wherein the polyalpha-olefin has a Kinematic viscosity at 40° C. of from 3 to 1,000 cSt.

10. The process of claim 1 wherein the polyalpha-olefin has a Viscosity Index of 90 or more.

11. The process of claim 1 wherein the polyalpha-olefin has a Viscosity Index of 90 to 200.

12. The process of claim 1 wherein the polyalpha-olefin has a weight average molecular weight of 100 to 50,000 g/mol.

13. The process of claim 1 wherein the polyalpha-olefin(s) are selected from the group consisting of 1-butene, 1-pentene, 1-hexene, 1-heptene, 1-octene, 1-nonene, 1-decene, 1-undecene, 1-dodecene, 1-tridecene, 1-tetradecene, 1-pentadecene, 1-hexadecene, 1-heptadecene, 1-octadecene, 1-nonadecene, 1-eicosene, 1-uneicosene, 1-docosene, 1-tricosene, 1-tetracosene, 1-pentacosene, 1-hexacosene, 4-methyl-1-pentene, 4-phenyl-1-butene, and 5-phenyl-1-pentene.

14. The process of claim 1 wherein the polyalpha-olefin(s) are selected from the group consisting of 1-pentene, 1-hexene, 1-heptene, 1-octene, 1-nonene, 1-decene, 1-undecene, 1-dodecene, 1-tridecene, 1-tetradecene, 1-pentadecene and 1-hexadecene.

15. The process of claim 1 wherein the polyalpha-olefin comprises octene, decene, and dodecene.

16. The process of claim 1 wherein the polyalpha-olefin has a dielectric constant of 2.5 or less (1 kHz at 23° C.).

17. The process of claim 1 wherein the polyalpha-olefin has a flash point of 150° C. or more.

18. The process of claim 1 wherein the polyalpha-olefin has a specific gravity of 0.75 to 0.96 g/cm$^3$.

19. The process of claim 1 wherein ethylene, propylene and butene monomers are present at less than 1 weight %.

20. The process of claim 1 wherein the monomers having 5 to 24 carbon atoms are present at 70 mole % or more.

21. The process of claim 1 further comprising
1) optionally treating the polyalpha-olefin to reduce heteroatom containing compounds to less than 600 ppm,
2) optionally separating the polyalpha-olefins from solvents or diluents;
3) contacting the polyalpha-olefin with hydrogen and a hydrogenation catalyst; and
4) obtaining a polyalpha-olefin having a bromine number less than 1.8.

22. The process of claim 21 wherein the polyalpha-olefin is treated to remove heteroatom containing compounds prior to contacting with the hydrogen and or the hydrogenation catalyst.

23. The process of claim 22 wherein the treated polyalpha-olefin comprises 100 ppm of heteroatom containing compounds or less.

24. The process of claim 22 wherein the treated polyalpha-olefin comprises 10 ppm of heteroatom containing compounds or less.

25. The process of claim 21 where in the polyalpha-olefin is contacted with hydrogen and a hydrogenation catalyst selected from the group consisting of supported Group 7, 8, 9, and 10 metals.

26. The process of claim 21 wherein the polyalpha-olefin is contacted with hydrogen and a hydrogenation catalyst selected from the group consisting of one or more of Ni, Pd, Pt, Co, Rh, Fe, Ru, Os, Cr, Mo, and W, supported on kieselguhr, silica, alumina, clay, titania, zirconia, or mixed metal oxide supports.

27. The process of claim 1 wherein the activator comprises one or more of N,N-dimethylanilinium tetra(pentafluorophenyl)borate, N,N-dialkylphenylanilinium tetra(pentafluorophenyl)borate (where the alkyl is a C1 to C18 alkyl group), trityl tetra(pentafluorophenyl)borate, tris(pentafluorophenyl)boron, tri-alkylammonium tetra(pentafluorophenyl)borate (where the alkyl is a C1 to C18 alkyl group), tetra-alkylammonium tetra(pentafluorophenyl)borate (where the alkyl is a C1 to C18 alkyl group).

28. The process of claim 1 wherein the transition metal compound comprises one or more of:
Bis(methylcyclopentadienyl)hafnium dimethyl,
Bis(methylcyclopentadienyl)zirconium dimethyl,
Bis(ethylcyclopentadienyl)zirconium dimethyl,
Bis(n-butylcyclopentadienyl)zirconium dimethyl,
Bis(n-propylcyclopentadienyl)hafnium dimethyl, or
Bis(n-propylcyclopentadienyl)zirconium dimethyl.

29. The process of claim 1 wherein the alkylaluminum compound is represented by the formula: $R_3Al$, where each R is, independently, selected from the group consisting of methyl, ethyl, n-propyl, iso-propyl, iso-butyl, n-butyl, t-butyl, n-pentyl, iso-pentyl, neopentyl, n-hexyl, iso-hexyl, n-heptyl, iso-heptyl, n-octyl, iso-octyl, n-nonyl, n-decyl, n-undecyl, n-dodecyl, n-tridecyl, n-tetradecyl, n-pentadecyl, n-hexadecyl, n-heptadecyl, n-octadecyl, and their iso-analogs.

30. The process of claim 1 wherein the process is a continuous process comprising:
a) continuously introducing a feed stream comprising at least 10 mole % of the one or more C3 to C24 alpha-olefins into a reactor,
b) continuously introducing the transition metal compound and the activator into the reactor,
c) optionally continuously introducing co-activator into the reactor, and
d) continuously withdrawing the polyalpha-olefin from the reactor.

31. The process of claim 30 further comprising maintaining a concentration of hydrogen in the reactor of 10,000 ppm or less by weight.

32. The process of claim 30 wherein the process further comprises:
1) optionally, continuously treating the polyalpha-olefin to reduce heteroatom containing compounds to less than 600 ppm,
2) optionally, continuously fractionating the polyalpha-olefin to separate the light and heavy fractions, where the heavy fractions have 20 or more carbons,
3) continuously contacting the polyalpha-olefin with hydrogen and a hydrogenation catalyst,
4) continuously obtaining a polyalpha-olefin having a bromine number less than 1.8.

33. The process of claim 1 wherein the temperature in the reactor is from −10° C. to 250° C.

34. The process of claim 1 wherein the temperature is from 30° C. to 220° C.

35. The process of claim 1 wherein the temperature is from 50° C. to 180° C.

36. The process of claim 1 wherein the monomers, transition metal compound and activator are contacted for a residence time of 5 minutes to 100 hours.

37. The process of claim 1 wherein solvent or diluent is present.

38. The process of claim 37 wherein the solvent or diluent is selected from the group consisting of butanes, pentanes, hexanes, heptanes, octanes, nonanes, decanes, undecanes, dodecanes, tridecanes, tetradecanes, pentadecanes, hexadecanes, benzene, toluene, o-xylene, m-xylene, p-xylene, mixed xylenes, ethylbenzene, isopropylbenzene, and n-butylbenzene.

39. The process of claim 1 wherein the monomers are contacted with the transition metal compound and the activator in a reactor and the reactor is a continuous stirred tank reactor.

40. The process of claim 1 wherein catalyst residual is removed from the product by contacting with a solid sorbent.

41. The process of claim 1 where the monomers are contacted with the transition metal compound and the activator in the solution phase.

42. The process of claim 1 where the monomers are contacted with the transition metal compound and the activator in the slurry phase.

43. The process of claim 1 wherein the monomers are contacted with an alkylaluminum compound prior to being introduced into the reactor.

44. The process of claim 43 where an alkylaluminum compound is present and the compound is selected from tri-isobutylaluminum, tri-n-octylaluminum, tri-n-hexylaluminum, and tri-n-dodecylaluminum.

45. The process of claim 1 where the transition metal compound and or activator are combined with an alkylaluminum compound prior to entering the reactor.

46. The process of claim 45 where an alkylaluminum compound is present and the compound is selected from tri-isobutylaluminum, tri-n-octylaluminum, tri-n-hexylaluminum, and tri-n-dodecylaluminum.

47. The process of claim 1 where in the polyalpha-olefin is contacted with hydrogen and a hydrogenation catalyst selected from the group consisting of supported Group 7, 8, 9, and 10 metals.

48. The process of claim 1 wherein the polyalpha-olefin is contacted with hydrogen and a hydrogenation catalyst selected from the group consisting of one or more of Ni, Pd, Pt, Co, Rh, Fe, Ru, Os, Cr, Mo, and W, supported on kieselguhr, silica, alumina, clay, titania, zirconia, or mixed metal oxide supports.

49. The process of claim 1 wherein the polyalpha-olefin is contacted with hydrogen and a hydrogenation catalyst at a temperature from 25 to 350° C.

50. The process of claim 1 wherein the product produced has 60 wt % or less C10 dimer.

51. The process of claim 1 wherein the product produced has 40 wt % or less C10 dimer.

52. The process of claim 1 wherein the process further comprises:
1) catalyst residual is removed from the polyalpha-olefin by contacting the polyalpha-olefin with a solid sorbent,
2) optionally, treating the polyalpha-olefin to reduce heteroatom containing compounds to less than 600 ppm,
3) optionally, fractionating the polyalpha-olefin to separate the light and heavy fractions, where the heavy fractions have 20 or more carbons,
4) contacting the polyalpha-olefin with hydrogen and a hydrogenation catalyst, and
5) obtaining a polyalpha-olefin having a bromine number less than 1.8.

53. A process to produce a polyalpha-olefin comprising:
1) contacting one or more alpha-olefin monomers having 3 to 24 carbon atoms with an unbridged substituted bis cyclopentadienyl transition metal compound having at least two substitutions on at least one cyclopentadienyl ring, a non-coordinating anion activator, and an alkylaluminum compound, where the molar ratio of transition metal compound to activator is 10:1 to 0.1:1, the molar ratio of alkyl aluminum compound to transition metal compound is 1:4 to 4000:1, and the milligram amount of transition metal compound per gram of alpha-olefin monomer is in the range of 0.001 to 1, under polymerization conditions wherein:
i) hydrogen is present at a partial pressure of 0.1 psi to less than 50 psi, based upon the total pressure of the reactor or the concentration of the hydrogen is from 1 to 10,000 ppm by weight;
ii) wherein the alpha-olefin monomer(s) having 3 to 24 carbon atoms are present at 10 volume % or more based upon the total volume of the catalyst/activator/alkylaluminum compound solutions, monomers, and any diluents or solvents present in the reaction;
iii) the residence time of the reaction is at least 5 minutes;
iv) the productivity of the process is at least 43,000 grams of total product per gram of transition metal compound;
v) the process is continuous or semi-continuous, and
vi) ethylene is not present at more than 30 volume % of the monomers entering the reaction zone; and
2) obtaining a polyalpha-olefin (PAO) wherein the PAO has a Mw/Mn of at least 1 and no greater than 1.4, optionally hydrogenating the PAO, wherein the PAO comprises at least 50 mole % of a C3 to C24 alpha-olefin monomer, and wherein the PAO has a kinematic viscosity at 100° C. of 20 cSt or less.

54. The process of claim 53 wherein the transition metal compound is represented by the formula:

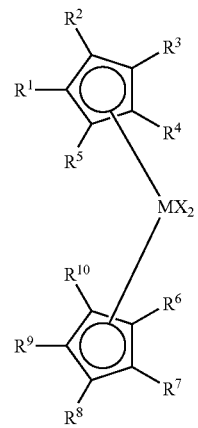

where M is a Group 4 metal;

each X is a hydrogen, halogen, hydride radicals, hydrocarbyl radicals, substituted hydrocarbyl radicals, halocarbyl radicals, substituted halocarbyl radicals, silylcarbyl radicals, substituted silylcarbyl radicals, germylcarbyl radicals, or substituted germylcarbyl radicals, or both X are joined and bound to the metal atom to form a metallacycle ring containing from about 3 to about 20 carbon atoms, or both together can be an olefin, diolefin or aryne ligand; and $R^1$ to $R^{10}$ are independently, a radical group which is a hydrogen, a heteroatom, hydrocarbyl, substituted hydrocarbyl, halocarbyl, substituted halocarbyl, silylcarbyl or germylcarbyl, provided that: 1) at least two of $R^1$ to $R^5$ are not hydrogen, or 2) at least two of $R^1$ to $R^5$ are not hydrogen and at least two of $R^6$ to $R^{10}$ are not hydrogen, and where any two adjacent $R^1$ to $R^5$ groups may form a C4 to C20 cyclic or poly cyclic moiety, and where any two adjacent $R^6$ to $R^{10}$ groups may form a C4 to C20 cyclic or poly cyclic moiety.

55. The process of claim 53 wherein the PAO has a pour point of 0° C. or less.

56. The process of claim 53 wherein the polyalpha-olefin has a Viscosity Index of 90 or more.

57. The process of claim 53 wherein the polyalpha-olefin has a weight average molecular weight of 100 to 50,000 g/mol.

58. The process of claim 53 wherein the polyalpha-olefin(s) are selected from the group consisting of 1-pentene, 1-hexene, 1-heptene, 1-octene, 1-nonene, 1-decene, 1-undecene, 1-dodecene, 1-tridecene, 1-tetradecene, 1-pentadecene and 1-hexadecene.

59. The process of claim 53 further comprising:
1) optionally treating the polyalpha-olefin to reduce heteroatom containing compounds to less than 600 ppm,
2) optionally separating the polyalpha-olefins from solvents or diluents;
3) contacting the polyalpha-olefin with hydrogen and a hydrogenation catalyst; and
4) obtaining a polyalpha-olefin having a bromine number less than 1.8.

60. The process of claim 53 wherein the activator comprises one or more of N,N-dimethylanilinium tetra(pentafluorophenyl)borate, N,N-dialkylphenylanilinium tetra(pentafluorophenyl)borate (where the alkyl is a C1 to C18 alkyl group), trityl tetra(pentafluorophenyl)borate, tris(pentafluorophenyl)boron, tri-alkylammonium tetra(pentafluorophenyl)borate (where the alkyl is a C1 to C18 alkyl group), tetra-alkylammonium tetra(pentafluorophenyl)borate (where the alkyl is a C1 to C18 alkyl group).

61. The process of claim 53 wherein the transition metal compound comprises one or more of:
Bis(1,2-dimethylcyclopentadienyl)zirconium dichloride,
Bis(1,3-dimethylcyclopentadienyl)zirconium dichloride,
Bis(1,2,3-trimethylcyclopentadienyl)zirconium dichloride,
Bis(1,2,4-trimethylcyclopentadienyl)zirconium dichloride,
Bis(1,2,3,4-tetramethylcyclopentadienyl)zirconium dichloride,
Bis(1,2,3,4,5-pentamethylcyclopentadienyl)zirconium dichloride,
Bis(1-methyl-2-ethylcyclopentadienyl)zirconium dichloride,
Bis(1-methyl-2-n-propylcyclopentadienyl)zirconium dichloride,
Bis(1-methyl-2-n-butylcyclopentadienyl)zirconium dichloride,
Bis(1-methyl-3-ethylcyclopentadienyl)zirconium dichloride,
Bis(1-methyl-3-n-propylcyclopentadienyl)zirconium dichloride,
Bis(1-methyl-3-n-butylcyclopentadienyl)zirconium dichloride,
Bis(1-methyl-3-n-pentylcyclopentadienyl)zirconium dichloride,
Bis(1,2-dimethyl-4-ethylcyclopentadienyl)zirconium dichloride,
Bis(1,2-dimethyl-4-n-propylcyclopentadienyl)zirconium dichloride,
Bis(1,2-dimethyl-4-n-butylcyclopentadienyl)zirconium dichloride,
Bis(1,2-diethylcyclopentadienyl)zirconium dichloride,
Bis(1,3-diethylcyclopentadienyl)zirconium dichloride,
Bis(1,2-di-n-propylcyclopentadienyl)zirconium dichloride,
Bis(1,2-di-n-butylcyclopentadienyl)zirconium dichloride,
Bis(1-methyl-2,4-diethylcyclopentadienyl)zirconium dichloride,
Bis(1,2-diethyl-4-n-propylcyclopentadienyl)zirconium dichloride,
Bis(1,2-diethyl-4-n-butylcyclopentadienyl)zirconium dichloride,
Bis(1-methyl-3-i-propylcyclopentadienyl)zirconium dichloride,
Bis(1-ethyl-3-i-propylcyclopentadienyl)zirconium dichloride,
(1,2-dimethylcyclopentadienyl)(cyclopentadienyl)zirconium dichloride,
(1,3-dimethylcyclopentadienyl)(cyclopentadienyl)zirconium dichloride,
(1,2-dimethylcyclopentadienyl)(methylcyclopentadienyl)zirconium dichloride,
(1,2-dimethylcyclopentadienyl)(ethylcyclopentadienyl)zirconium dichloride,
(1,2-dimethylcyclopentadienyl)(1,2-di-n-butylcyclopentadienyl)zirconium dichloride,
(1,3-dimethylcyclopentadienyl)(cyclopentadienyl)zirconium dichloride,
(1,3-dimethylcyclopentadienyl)(1,2-dimethylcyclopentadienyl)zirconium dichloride,
(1,3-dimethylcyclopentadienyl)(1,3-diethylcyclopentadienyl)zirconium dichloride,
Bis(1-methylindenyl)zirconium dichloride,
Bis(2-methylindenyl)zirconium dichloride,
Bis(4-methylindenyl)zirconium dichloride,
Bis(4,7-dimethylindenyl)zirconium dichloride,
Bis(4,5,6,7-tetrahydroindenyl)zirconium dichloride,
Bis(4,5,6,7-tetrahydro-2-methylindenyl)zirconium dichloride,
Bis(4,5,6,7-tetrahydro-4,7-dimethylindenyl)zirconium dichloride,
(Cyclopentadienyl)(4,5,6,7-tetrahydroindenyl)zirconium dichloride,
Bis(1,2-dimethylcyclopentadienyl)zirconium dimethyl,
Bis(1,3-dimethylcyclopentadienyl)zirconium dimethyl,
Bis(1,2,3-trimethylcyclopentadienyl)zirconium dimethyl,
Bis(1,2,4-trimethylcyclopentadienyl)zirconium dimethyl,
Bis(1,2,3,4-tetramethylcyclopentadienyl)zirconium dimethyl,
Bis(1,2,3,4,5-pentamethylcyclopentadienyl)zirconium dimethyl,
Bis(1-methyl-2-ethylcyclopentadienyl)zirconium dimethyl,
Bis(1-methyl-2-n-propylcyclopentadienyl)zirconium dimethyl,
Bis(1-methyl-2-n-butylcyclopentadienyl)zirconium dimethyl,
Bis(1-methyl-3-ethylcyclopentadienyl)zirconium dimethyl,
Bis(1-methyl-3-n-propylcyclopentadienyl)zirconium dimethyl,
Bis(1-methyl-3-n-butylcyclopentadienyl)zirconium dimethyl,
Bis(1-methyl-3-n-pentylcyclopentadienyl)zirconium dimethyl,
Bis(1,2-dimethyl-4-ethylcyclopentadienyl)zirconium dimethyl,
Bis(1,2-dimethyl-4-n-propylcyclopentadienyl)zirconium dimethyl,
Bis(1,2-dimethyl-4-n-butylcyclopentadienyl)zirconium dimethyl,
Bis(1,2-diethylcyclopentadienyl)zirconium dimethyl,
Bis(1,3-diethylcyclopentadienyl)zirconium dimethyl,
Bis(1,2-di-n-propylcyclopentadienyl)zirconium dimethyl,
Bis(1,2-di-n-butylcyclopentadienyl)zirconium dimethyl,
Bis(1-methyl-2,4-diethylcyclopentadienyl)zirconium dimethyl,
Bis(1,2-diethyl-4-n-propylcyclopentadienyl)zirconium dimethyl,
Bis(1,2-diethyl-4-n-butylcyclopentadienyl)zirconium dimethyl,
Bis(1-methyl-3-i-propylcyclopentadienyl)zirconium dimethyl,
Bis(1-ethyl-3-i-propylcyclopentadienyl)zirconium dimethyl, (1,2-dimethylcyclopentadienyl)(cyclopentadienyl)zirconium dimethyl,
(1,3-dimethylcyclopentadienyl)(cyclopentadienyl)zirconium dimethyl,
(1,2-dimethylcyclopentadienyl)(methylcyclopentadienyl)zirconium dimethyl,
(1,2-dimethylcyclopentadienyl)(ethylcyclopentadienyl)zirconium dimethyl,
(1,2-dimethylcyclopentadienyl)(1,2-di-n-butylcyclopentadienyl)zirconium dimethyl,
(1,3-dimethylcyclopentadienyl)(cyclopentadienyl)zirconium dimethyl,
(1,3-dimethylcyclopentadienyl)(1,2-dimethylcyclopentadienyl)zirconium dimethyl,
(1,3-dimethylcyclopentadienyl)(1,3-diethylcyclopentadienyl)zirconium dimethyl,
(tetramethylcyclopentadienyl)(n-propylcyclopentadienyl)zirconium dimethyl,
Bis(1-methylindenyl)zirconium dimethyl,
Bis(2-methylindenyl)zirconium dimethyl,
Bis(4-methylindenyl)zirconium dimethyl,
Bis(4,7-dimethylindenyl)zirconium dimethyl,
Bis(4,5,6,7-tetrahydroindenyl)zirconium dimethyl,
Bis(4,5,6,7-tetrahydro-2-methylindenyl)zirconium dimethyl,
Bis(4,5,6,7-tetrahydro-4,7-dimethylindenyl)zirconium dimethyl,
(Cyclopentadienyl)(4,5,6,7-tetrahydroindenyl)zirconium dimethyl,
Bis(1,2-dimethylcyclopentadienyl)hafnium dichloride,
Bis(1,3-dimethylcyclopentadienyl)hafnium dichloride,
Bis(1,2,3-trimethylcyclopentadienyl)hafnium dichloride,
Bis(1,2,4-trimethylcyclopentadienyl)hafnium dichloride,
Bis(1,2,3,4-tetramethylcyclopentadienyl)hafnium dichloride,
Bis(1,2,3,4,5-pentamethylcyclopentadienyl)hafnium dichloride,
Bis(1-methyl-2-ethylcyclopentadienyl)hafnium dichloride,
Bis(1-methyl-2-n-propylcyclopentadienyl)zirconium dichloride,
Bis(1-methyl-2-n-butyllcyclopentadienyl)hafnium dichloride,
Bis(1-methyl-3-ethylcyclopentadienyl)hafnium dichloride,
Bis(1-methyl-3-n-propylcyclopentadienyl)hafnium dichloride,
Bis(1-methyl-3-n-butylcyclopentadienyl)hafnium dichloride,
Bis(1-methyl-3-n-pentylcyclopentadienyl)hafnium dichloride,
Bis(1,2-dimethyl-4-ethylcyclopentadienyl)hafnium dichloride,
Bis(1,2-dimethyl-4-n-propylcyclopentadienyl)hafnium dichloride,
Bis(1,2-dimethyl-4-n-butylcyclopentadienyl)hafnium dichloride,
Bis(1,2-diethylcyclopentadienyl)hafnium dichloride,
Bis(1,3-diethylcyclopentadienyl)hafnium dichloride,
Bis(1,2-di-n-propylcyclopentadienyl)hafnium dichloride,
Bis(1,2-di-n-butylcyclopentadienyl)hafnium dichloride,
Bis(1-methyl-2,4-diethylcyclopentadienyl)hafnium dichloride,
Bis(1,2-diethyl-4-n-propylcyclopentadienyl)hafnium dichloride,
Bis(1,2-diethyl-4-n-butylcyclopentadienyl)hafnium dichloride,
Bis(1-methyl-3-i-propylcyclopentadienyl)hafnium dichloride,
Bis(1-ethyl-3-i-propylcyclopentadienyl)hafnium dichloride,
(1,2-dimethylcyclopentadienyl)(cyclopentadienyl)hafnium dichloride,
(1,3-dimethylcyclopentadienyl)(cyclopentadienyl)hafnium dichloride,
(1,2-dimethylcyclopentadienyl)(methylcyclopentadienyl)hafnium dichloride,
(1,2-dimethylcyclopentadienyl)(ethylcyclopentadienyl)hafnium dichloride,
(1,2-dimethylcyclopentadienyl)(1,2-di-n-butylcyclopentadienyl)hafnium dichloride,
(1,3-dimethylcyclopentadienyl)(cyclopentadienyl)hafnium dichloride,
(1,3-dimethylcyclopentadienyl)(1,2-dimethylcyclopentadienyl)hafnium dichloride,
(1,3-dimethylcyclopentadienyl)(1,3-diethylcyclopentadienyl)hafnium dichloride,
Bis(1-methylindenyl)hafnium dichloride,
Bis(2-methylindenyl)hafnium dichloride,
Bis(4-methylindenyl)hafnium dichloride,
Bis(4,7-dimethylindenyl)hafnium dichloride,
Bis(4,5,6,7-tetrahydroindenyl)hafnium dichloride,
Bis(4,5,6,7-tetrahydro-2-methylindenyl)hafnium dichloride,
Bis(4,5,6,7-tetrahydro-4,7-dimethylindenyl)hafnium dichloride,
(Cyclopentadienyl)(4,5,6,7-tetrahydroindenyl)hafnium dichloride,
Bis(1,2-dimethylcyclopentadienyl)hafnium dimethyl,
Bis(1,3-dimethylcyclopentadienyl)hafnium dimethyl,
Bis(1,2,3-trimethylcyclopentadienyl)hafnium dimethyl,
Bis(1,2,4-trimethylcyclopentadienyl)hafnium dimethyl,
Bis(1,2,3,4-tetramethylcyclopentadienyl)hafnium dimethyl,
Bis(1,2,3,4,5-pentamethylcyclopentadienyl)hafnium dimethyl,
Bis(1-methyl-2-ethylcyclopentadienyl)hafnium dimethyl,
Bis(1-methyl-2-n-propylcyclopentadienyl)hafnium dimethyl,
Bis(1-methyl-2-n-butyllcyclopentadienyl)hafnium dimethyl,
Bis(1-methyl-3-ethylcyclopentadienyl)hafnium dimethyl,
Bis(1-methyl-3-n-propylcyclopentadienyl)hafnium dimethyl,
Bis(1-methyl-3-n-butylcyclopentadienyl)hafnium dimethyl,
Bis(1-methyl-3-n-pentylcyclopentadienyl)hafnium dimethyl,
Bis(1,2-dimethyl-4-ethylcyclopentadienyl)hafnium dimethyl,
Bis(1,2-dimethyl-4-n-propylcyclopentadienyl)hafnium dimethyl,
Bis(1,2-dimethyl-4-n-butylcyclopentadienyl)hafnium dimethyl,
Bis(1,2-diethylcyclopentadienyl)hafnium dimethyl,
Bis(1,3-diethylcyclopentadienyl)hafnium dimethyl,
Bis(1,2-di-n-propylcyclopentadienyl)hafnium dimethyl,
Bis(1,2-di-n-butylcyclopentadienyl)hafnium dimethyl,
Bis(1-methyl-2,4-diethylcyclopentadienyl)hafnium dimethyl,
Bis(1,2-diethyl-4-n-propylcyclopentadienyl)hafnium dimethyl,
Bis(1,2-diethyl-4-n-butylcyclopentadienyl)hafnium dimethyl, Bis(1-methyl-3-i-propylcyclopentadienyl)hafnium dimethyl,
Bis(1-ethyl-3-i-propylcyclopentadienyl)hafnium dimethyl,
(1,2-dimethylcyclopentadienyl)(cyclopentadienyl) hafnium dimethyl,
(1,3-dimethylcyclopentadienyl)(cyclopentadienyl) hafnium dimethyl,
(1,2-dimethylcyclopentadienyl)(methylcyclopentadienyl) hafnium dimethyl,
(1,2-dimethylcyclopentadienyl)(ethylcyclopentadienyl) hafnium dimethyl,
(1,2-dimethylcyclopentadienyl)(1,2-di-n-butylcyclopentadienyl)hafnium dimethyl,
(1,3-dimethylcyclopentadienyl)(cyclopentadienyl) hafnium dimethyl,
(1,3-dimethylcyclopentadienyl)(1,2-dimethylcyclopentadienyl)hafnium dimethyl,
(1,3-dimethylcyclopentadienyl)(1,3-diethylcyclopentadienyl)hafnium dimethyl,
Bis(1-methylindenyl)hafnium dimethyl,
Bis(2-methylindenyl)hafnium dimethyl,
Bis(4-methylindenyl)hafnium dimethyl,
Bis(4,7-dimethylindenyl)hafnium dimethyl,
Bis(4,5,6,7-tetrahydroindenyl)hafnium dimethyl,
Bis(4,5,6,7-tetrahydro-2-methylindenyl)hafnium dimethyl,
Bis(4,5,6,7-tetrahydro-4,7-dimethylindenyl)hafnium dimethyl, or
(Cyclopentadienyl)(4,5,6,7-tetrahydroindenyl)hafnium dimethyl.

62. The process of claim 53 wherein the alkylaluminum compound is represented by the formula: $R_3Al$, where each R is, independently, selected from the group consisting of methyl, ethyl, n-propyl, iso-propyl, iso-butyl, n-butyl, t-butyl, n-pentyl, iso-pentyl, neopentyl, n-hexyl, iso-hexyl, n-heptyl, iso-heptyl, n-octyl, iso-octyl, n-nonyl, n-decyl, n-undecyl, n-dodecyl, n-tridecyl, n-tetradecyl, n-pentadecyl, n-hexadecyl, n-heptadecyl, n-octadecyl, and their iso-analogs.

63. The process of claim 53 wherein the temperature in the reactor is from −10° C. to 250° C.

64. The process of claim 53 wherein solvent or diluent is present.

65. The process of claim 53 wherein the monomers are contacted with the alkylaluminum compound prior to being introduced into the reactor.

66. The process of claim 53 where the transition metal compound and or activator are combined with the alkylaluminum compound prior to entering the reactor.

67. The process of claim 53 wherein the product produced has 40 wt % or less C10 dimer.

* * * * *